US010048272B2

(12) United States Patent
Edwards et al.

(10) Patent No.: US 10,048,272 B2
(45) Date of Patent: *Aug. 14, 2018

(54) HIGH-AFFINITY SMALL MOLECULE FORMYLPEPTIDE RECEPTOR LIGANDS FROM SCREENING OF COMBINATORIAL MIXTURE-BASED LIBRARIES

(71) Applicants: STC.UNM, Albuquerque, NM (US); TORREY PINES INSTITUTE FOR MOLECULAR STUDIES, Port St Lucie, FL (US)

(72) Inventors: Bruce S. Edwards, Albuquerque, NM (US); Larry A. Sklar, Albuquerque, NM (US); Clemencia Pinilla, Cardiff, CA (US); Richard A. Houghten, Vero Beach, FL (US); Jon R. Appel, Cardiff, CA (US); Marc A. Giulianotti, Vero Beach, FL (US); Jose Medina-Franco, Port St Lucie, FL (US)

(73) Assignees: STC.UNM, Albuquerque, NM (US); Torrey Pines Institute for Molecular Studies, Port St. Lucie, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/013,102

(22) Filed: Feb. 2, 2016

(65) Prior Publication Data

US 2016/0320402 A1  Nov. 3, 2016

Related U.S. Application Data

(63) Continuation of application No. 14/174,564, filed on Feb. 6, 2014, now Pat. No. 9,310,364.

(60) Provisional application No. 61/762,083, filed on Feb. 7, 2013.

(51) Int. Cl.

| | | |
|---|---|---|
| A61K 31/497 | (2006.01) | |
| A61K 31/517 | (2006.01) | |
| A61K 31/17 | (2006.01) | |
| G01N 33/68 | (2006.01) | |
| C07D 403/14 | (2006.01) | |
| A61K 31/496 | (2006.01) | |
| A61K 45/06 | (2006.01) | |
| C07C 275/28 | (2006.01) | |
| C40B 30/02 | (2006.01) | |
| G01N 33/74 | (2006.01) | |
| A61K 38/00 | (2006.01) | |
| C07D 241/08 | (2006.01) | |
| C07K 1/04 | (2006.01) | |

(52) U.S. Cl.
CPC ......... *G01N 33/6845* (2013.01); *A61K 31/17* (2013.01); *A61K 31/496* (2013.01); *A61K 45/06* (2013.01); *C07C 275/28* (2013.01); *C07D 403/14* (2013.01); *C40B 30/02* (2013.01); *G01N 33/74* (2013.01); *A61K 38/00* (2013.01); *B01J 2219/00585* (2013.01); *C07D 241/08* (2013.01); *C07K 1/047* (2013.01); *G01N 2333/726* (2013.01)

(58) Field of Classification Search
CPC ..... A61K 31/495; A61K 31/17; C07D 401/12
USPC ................................ 514/252.12, 258.1, 596
See application file for complete search history.

(56) References Cited

U.S. PATENT DOCUMENTS 9,310,364 B1* 4/2016 Edwards .............. C07D 403/14

OTHER PUBLICATIONS

Santos RG, et al. Use and Implications of the Harmonic Mean Model on Mixtures for Basic Research and Drug Discovery. ACS Comb Sci, 2011;13:337-344.
Schimmer AD, et al. Small-molecule antagonists of apoptosis suppressor XIAP exhibit broad antitumor activity. Cancer Cell, 2004;5:25-35.
Singh N, et al. Chemoinformatic analysis of combinatorial libraries, drugs, natural products, and molecular libraries small molecule repository. J Chem Inf Model, 2009;49:1010-1024.
Zhang JH, Chung TD, Oldenburg KR. A simple statistical parameter for use in evaluation and validation of high throughput screening assays. J Biomol Screen, 1999;4:67-73.
Zhou C, et al. Pharmacological characterization of a novel nonpeptide antagonist for formyl peptide receptor-like 1. Mol Pharmacol, 2007;72:976-983.
Zhou Y, et al. Formalpeptide receptor FPR and the rapid growth of malignant human gliomas. J Natl Cancer Inst, 2005;97:823-835.
Stumpfe D, Bajorath J. Exploring Activity Cliffs in Medicinal Chemistry. Journal of Medicinal Chemistry, 2012;55:2932-2942.
Bajorath J. Modeling of activity landscapes for drug discovery. Expert Opin Drug Discov, 2012;7:463-473.
Medina-Franco JL. Scanning Structure-Activity Relationships with SAS and Related Maps: From Consensus Activity Cliffs to Selectivity Switches. J Chem Inf Model, 2012;52:2485-2493.
Hu X, Hu Y, Vogt M, Stumpfe D, Bajorath J. MMP-Cliffs: Systematic Identification of Activity Cliffs on the Basis of Matched Molecular Pairs. J Chem Inf Model, 2012;52:1138-1145.

(Continued)

*Primary Examiner* — Raymond J Henley, III
(74) *Attorney, Agent, or Firm* — Henry D. Coleman; R. Neil Sudol

(57) ABSTRACT

The present invention provides novel methods and assays for high-throughput screening of combinatorial libraries to identify FPR1 and/or FPR2 ligands (e.g., agonists and/or antagonists), preferably FPR1 agonists and/or FPR2 antagonists, by positional scanning deconvolution.

The invention also provides novel FPR1 and FPR2 ligands (e.g, agonists and antagonists), related pharmaceutical compositions and methods of treating FPR1 and FPR2-related disorders.

10 Claims, 43 Drawing Sheets

(56) References Cited

OTHER PUBLICATIONS

Houghten RA, et al. Strategies for the use of mixture-bases synthetic combinatorial libraries: Scaffold ranking, direct testing, in vivo, and enhanced deconvolution by computational methods. J Comb Chem, 2008;10:3-19.
Medina-Franco JL, Giulianotti MA, Welmaker GS, Houghten RA. Shifting from the single to the multitarget paradigm in drug discovery. Drug Discovery Today, 2013, in press. DOI: 10.1016/j.drudis.2013.01.008.
Kolpak J, Connolly PJ, Lobanov VS, Agrafiotis DK. Enhanced SAR Maps: Expanding the Data Rendering Capabilities of a Popular Medicinal Chemistry Tool. J Chem Inf Model, 2009;49:2221-2230.
Wassermann AM, Haebel P, Weskamp N, Bajorath J. SAR Matrices: Automated Extraction of Information-Rich SAR Tables from Large Compound Data Sets. J Chem Inf Model, 2012;52:1769-1776.
Agrafiotis DK, Wiener JJM, Skalkin A, Kolpak J. Single R-Group Polymorphisms (SRPs) and R-Cliffs: An Intuitive Framework for Analyzing and Visualizing Activity Cliffs in a Single Analog Series. J Chem Inf Model, 2011;51:1122-1131.
Duffy BC, Zhu L, Decornez H, Kitchen DB. Single R-Group Polymorphisms (SRPs) and R-Cliffs: An Intuitive Framework for Analyzing and Visualizing Activity Cliffs in a Single Analog Series Bioorg Med Chem, 2012;20:5324-5342.
Perez-Villanueva J, et al. Structure-activity relationships of benzimidazole derivatives as antiparasitic agents: Dual activity-difference (DAD) maps. Med Chem Comm, 2011;2:44-49.
Medina-Franco JL, et al. Multitarget Structure-Activity Relationships Characterized by Activity-Difference Maps and Consensus Similarity Measure. J Chem Inf Model, 2011;51:2427-2439.
Yongye A, et al. Consensus Models of Activity Landscapes with Multiple Chemical, Conformer and Propert Representations. J Chem Inf Model, 2011;51:1259-1270.
Pinilla C, et al. Selective agonists and antagonists of formylpeptide receptors: duplex flow cytometry and mixture-based positional scanning libraries. Submitted.
Le Y, et al. The Neurotoxic Prion Peptide Fragment PrP106-126 Is a Chemotactic Agonist for the G Protein-Coupled Receptor Formyl Peptide Receptor-Like 1. J Immunol, 2001;166:1448-1451.
Perez-Villanueva J, et al. Case Plots for the Chemotype-Based Activity and Selectivity Analysis: A Case Study of Cyclooxygenase Inhibitors. Chem Biol Drug Des, 2012;80:752-762.
Mendez-Lucio O, Perez-Villanueva J, Castillo R, Medina-Franco JL. Activity Landscape Modeling of PPAR ligands with Dual-Activity Difference Maps. Bioorg Med Chem, 2012;20:3523-3532.
Medina-Franco JL. Activity Cliffs: Facts or Artifacts? Submitted.
Rogers D, Hahn M, Extended-Connectivity Fingerprints. J Chem in Model, 2010;50:742-754.
Sastry M, Lowrie JF, Dixon SL, Sherman W. Large-Scale Systematic Analysis of 2D Fingerprint Methods and Parameters to Improve Virtual Screening Enrichments. J Chem Inf Model, 2010;50:771-784.
Perez-Villanueva J, et al. Towards a systematic characterization of the antiprotozoal activity landscape of benzimidazole derivatives. Bioorg Med Chem, 2010;18:7380-7391.
Bender A. How similar are those molecules after all? Use two descriptors and you will have three different answers. Expert Opin Drug Discv, 2010;5:1141-1151.
Ranjit DK, et al. Small molecule functional analogs of peptides that inhibit lambda site-specific recombination and bind Holliday junctions. Bioorg Med Chem Lett, 2010;20;4531-4534.
Rideout MC, et al. Potent antimicrobial small molecules screened as inhibitors of tyrosine recombinases and Holliday junction-resolving enzymes. Mol Divers, 2011;15:989-1005.
Minond D, et al. Discovery of novel inhibitors of a disintegrin and metalloprotease 17 (ADAM17) using glycosylated and non-glycosylated substrates. J Biol Chem, 2012;287:36473-36487.
Pinilla C, et al. Selective agonist and antagonist of formylpeptide receptors:duplex flow cytometry and mixture-bases positional scanning libraries. Mol Pharmacol, 2013, submitted.
Medina-Franco JL, et al. Scanning structure-activity relationships in combiatorial data sets: Rapid identification of activity-switches. J Chemical Information and Modeling, 2013; submitted.
Ye RD, et al. International Union of Basic and Clinical Pharmacology. LXXIII. Nomenclature for the formyl peptide receptor (FPR) family. Pharmacol Rev, 2009;61:119-161.
Kirpotina LN, et al. Identification of novel small-molecule agonists for human formyl peptide receptors and pharmacophore models of their recognition. Mol Pharmacol, 2010;77:159-170.
Le Y, Murphy PM, Wang JM. Formyl-peptide receptors revisited. Trends Immunol, 2002;23:541-548.
Yao XH, et al. Chemoattractant receptors as pharmacological targets for elimination of glioma stem-like cells. Int Immunopharmacol, 2011;11:1961-1966.
Yao XH, et al. Production of angiogenic factors by human glioblastoma cells following activation of the G-protein couples formylpeptide receptor FPR. J Neurooncol, 2008;86:47-53.
Zhou Y, et al. Formylpeptide receptor FPR and the rapid growth of malignant human gliomas. J natl Cancer Inst, 2005;97;823-835.
Le Y, et al. Amyloid (beta)42 activates a G-protein-coupled chemoattractant receptor, FPR-like-1. J Neurosci, 2001;21: RC123.
Le Y, et al. The neurotoxic prion peptide fragment PrP(106-126) is a chemotactic agonist for the G protein-couples receptor formyl peptide receptor-like 1. J Immunol, 2001;166:1448-1451.
Su SB, et al. A seven-transmembrane, G protein-coupled receptor, FPRL1, mediates the chemotactic activity of serum amyloid A for human phagocytic cells. J Exp Med, 1999;189:395-402.
He R, Sang H, Ye RD. Serum amyloid A induces IL-8 secretion through a G protein-couples receptor, FPRL1/LXA4R. Blood, 2003;101:1572-1581.
Gavins, FN. Are formyl peptide receptors novel targets for therapeutic intervention in ischaemia-reperfusion injury? Trends Pharmacol Sci, 2010;31:266-276.
Gavins FN, et al. Leukocyte recruitment in the brain in sepsis: involvement of the annexin 1-FPR2/ALX anti-inflammatory system. FASEB J, 2012;26:4977-4989.
Riviere S, Challet L, Fluegge D, Spehr M, Rodriquez I. Formyl peptide receptor-like proteins are a novel family of vomeronasal chemosensors. Nature, 2009;459:574-577.
Dufton N, Perretti M. Therapeutic anti-inflammatory potential of formyl-peptide receptor agonists. Pharmacol Ther, 2010;127:175-188.
Young SM, et al. High-throughput screening with HyperCyt flow cytometry to detect small molecule formylpeptide receptor ligands. J Biomol Screen, 2005;10:374-382.
Young SM, et al. Duplex high-throughput flow cytometry screen identifies two novel formylpeptide receptor family probes. Cytometry A, 2009;75:253-263.
Edwards BS, et al. Integration of virtual screening with high-throughput flow cytometry to identify novel small molecule formylpeptide receptor antagonists. Mol Pharmacol, 2005;68:1301-1310.
Unitt J, et al. Discovery of small molecule human FPR1 receptor antagonists. Bioorg Med Chem Lett, 2011;21:2991-2997.
Morley AD, et al. Lead Optimisation of pyrazoles as novel FPR1 antagonists. Bioorg Med Chem Lett, 2012;22:532-536.
Khlebnikov AI, et al. Molecular docking of 2-benzimidazol-2-ylthio-N-phenylacetamide-derived small-molecule agonists of human formyl peptide receptor 1. J Mol Model, 2012;18:2831-2843.
Schepetkin IA, Kirpotina LN, Khlebnikov AI, Quinn MT. High-throughput screening for small-molecule activators of neutrophils: identification of novel N-formyl peptide receptor agonists. Mol Pharmacol, 2007;71:1061-1074.
Schepetkin IA, Kirpotina LN, Tian J, Khlebnikov AI, Ye RD, Quinn MT. Identification of novel formyl peptide receptor-like 1 agonists that induce macrophage tumor necrosis factor alpha production. Mol Pharmacol, 2008;74:392-402.

(56) References Cited

OTHER PUBLICATIONS

Cilibrizzi A, et al. 6-methyl-2,4-disubstituted pyridazin-3(2H)-ones: a novel class of small-molecule agonists for formyl peptide receptors. J Med Chem, 2009;52:5044-5057.
Burli RW, et al. Potent hFPRL1 (ALXR) agonists as potential anti-inflammatory agents. Bioorg Med Chem Lett, 2006;16:3713-3718.
Pinilla C, Appel JR, Blanc P, Houghten RA. Rapid identification of high affinity peptide ligands using positional scanning synthetic peptide combinatorial libraries. Biotechniques, 1992;13:901-905.
Dooley CT, Houghten RA. The use of positional scanning synthetic peptide combinatorial libraries for the rapid determination of opioid receptor ligands. Life Sci, 1993;52:1509-1517.
Lopez-Vallejo F, Giulianotti MA, Houghten RA, Medina-Franco JL. Expanding the medicinally relevant chemical space with compound libraries. Drug Discov Today, 2012;17:718-726.
Medina-Franco JL, et al. Characterization of activity landscapes using 2D and 3D similarity methods: consensus activity cliffs. J Chem Inf Model, 2009;49:477-491.
Maggiora GM. On outliers and activity cliffs—why QSAR often disappoints. J Chem Inf Model, 2006;46:1535.
Pinilla C, Appel JR, Borras E, Houghten RA. Advances in the use of synthetic combinatorial chemistry: mixture-based libraries. Nat Med, 2003;9:118-122.
Acharya AN, Ostresh JM, Houghten RA. Determination of isokinetic ratios necessary for equimolar incorporation of carboxylic acids in the solid-phase synthesis of mixture-based combinatorial libraries. Biopolymers, 2002;65:32-39.
Clark AM, Labute P. Detection and assignment of common scaffolds in project databases of lead molecules. J Med Chem, 2009;52:469-483.
Frohn M, et al. New 'chemical probes' to examine the role of the hFPRL1 (or ALXR) receptor in inflammation. Bioorg Med Chem Lett, 2007;17:6633-6637.
Giulianotti MA, et al. A novel method for the determination of isokinetic ratios and its application in the synthesis of two new positional scanning libraries. ACS Comb Sci, 2012;14:503-512.
Hensler ME, Bernstein G, Nizet V, Nefzi A. Pyrrolidine bis-cyclic guanidines with antimicrobial activity against drug-resistant Gram-positive pathogens identified from a mixture-based combinatorial library. Bioorg Med Chem Lett, 2006;16:5073-5079.
Houghten RA. General method for the rapid solid-phase synthesis of large number of peptides: Specificity of antigen-antibody interaction at the level of individual amino acids. Proc Natl Acad Sci USA, 1985;82:5131-5135.
Houghten RA, et al. Mixture-based synthetic combinatorial libraries. J Med Chem, 1999;42:3743-3778.
Houghten RA, et al. Generation and use of synthetic peptide combinatorial libraries for basic research and drug discovery. Nature, 1991;354:84-86.
Houghten RA, et al. Strategies for the use of mixture-based synthetic combinatorial libraries: Scaffold ranking, direct testing in vivo, and enhanced deconvolution by computational methods. J Comb Chem, 2008;10:3-19.
Kuckuck FW, Edwards BS, Sklar LA. High throughput flow cytometry. Cytometry, 2001;44:83-90.
Le Y, et al. The neurotoxic prion peptide fragment PrP(106-126) is a chemotactic agonist for the G protein-coupled receptor formyl peptide receptor-like 1. J Immunol, 2001;166:1448-1451.
Levesque L, Gaudreault RC, Marceau F. The interaction of 3,5-pyrazolidinedione drugs with receptors for f-Met-Leu-Phe on human neutrophil leukocytes: a study of the structure-activity relationship. Can J Physiol Pharmacol, 1991;69:419-425.
Munson PJ, Rodbard D. An exact correction to the "Cheng-Prusoff" correction. J Recept Res, 1988;8:533-546.
Nefzi A, Ong N, Houghten RA. An efficient two-step synthesis of mono-, di- and triureas from resin-bound amides. Tetrahedron Letters, 2000;41:5441-5446.
Nefzi A, Ostresh JM, Yu Y, Houghten RA. Combinatorial chemistry: libraries from libraries, the art of the diversity-oriented transformation of resin-bound peptides and chiral polyamides to low molecular weight acyclic and heterocyclic compounds. J Org Chem, 2004;69;3603-3609.
Ostresh JM, et al. "Libraries from libraries": Chemical transformation of combinatorial libraries to extend the range and repertoire of chemical diversity. Proc Natl Acad Sci USA, 1994;91:11138-11142.
Ostresh JM, Winkle JH, Hamashin VT, Houghten RA. Peptide libraries: Determination of relative reaction rates of protected amino acids in competitive couplings. Biopolymers, 1994;34:1681-1689.
Ramirez S, et al. High-throughput flow cytometry: validation in microvolume bioassays. Cytometry A, 2003;53:55-65.
Reilley KJ, et al. Identification of two novel, potent, low-liability antinociceptive compounds from the direct in vivo screening of a large mixture-based combinatorial library. AAPS J, 2010;12:318-329.
Santos RG, et al. The mathematics of a successful deconvolution: A quantitative assessment of mixture-based combinatorial libraries screened against two formypeptide receptors. Molecules, 2013;18:6408-6424.

* cited by examiner

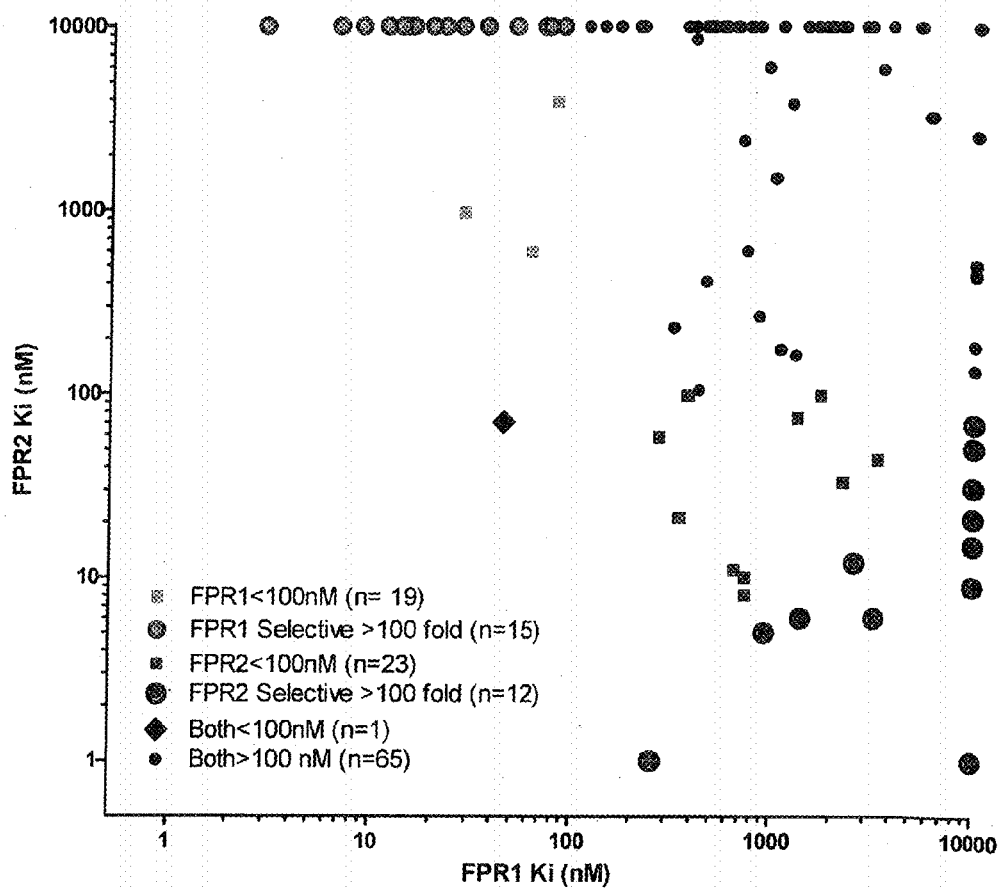

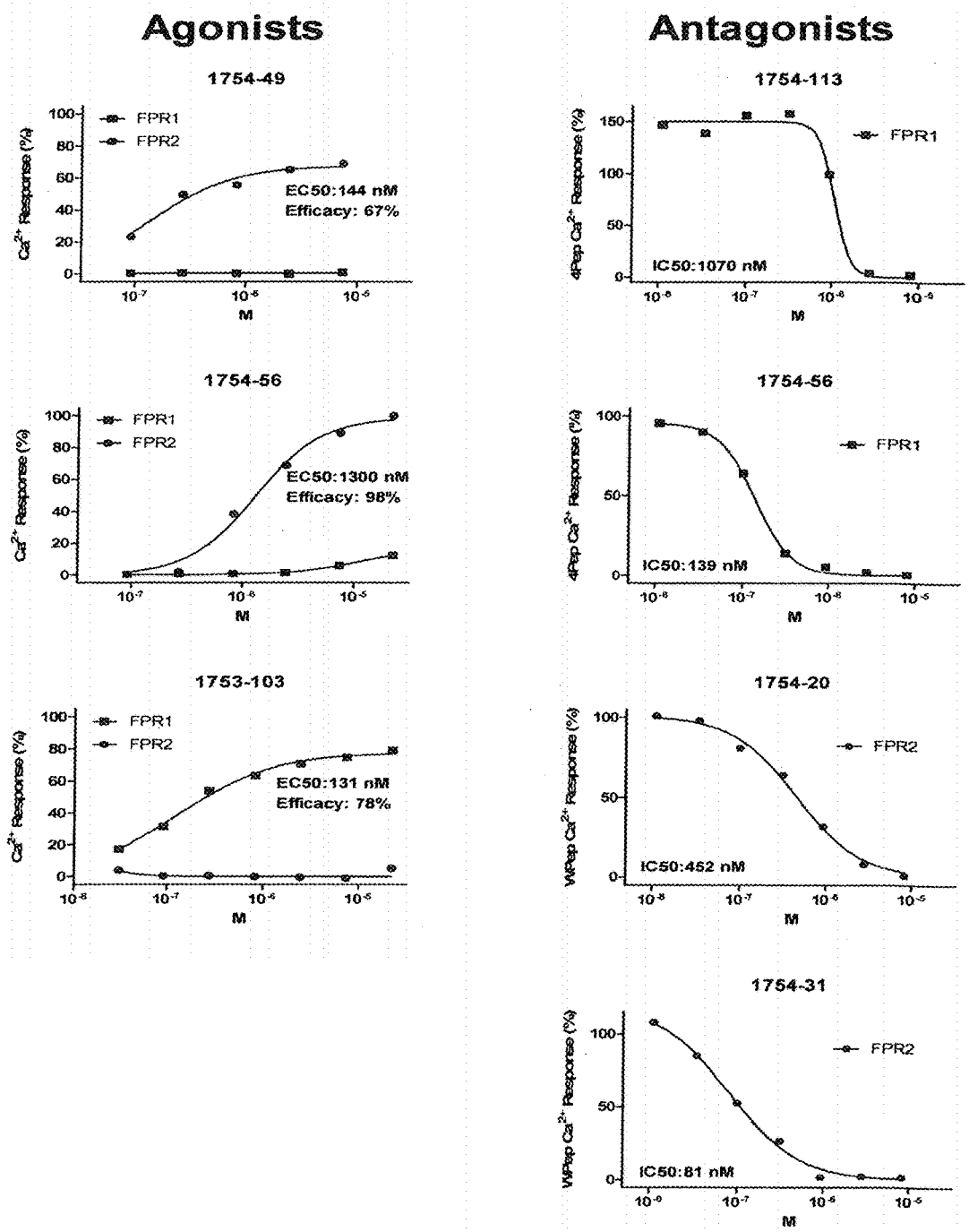
FIGURE 1EX2

Figure 1EX3 (Table 2)

Table 1. Structure and activity information for individual compounds derived from library 1344 (n = 107) and 1481 (n = 4).

| Library | Compound | R1 Functionality | R2 Functionality | R3 Functionality | R4 Functionality | FPR1 Ki; nM | FPR2 Ki; nM |
|---|---|---|---|---|---|---|---|
| 1344 | 1754-1 | R-2-naphthylmethyl | R-4-hydroxybenzyl | R-benzyl | 4-methyl-1-cyclohexyl-methyl | >10000 | >10000 |
| | 1754-2 | R-2-naphthylmethyl | R-4-hydroxybenzyl | R-4-hydroxybenzyl | cyclohexyl-propyl | >10000 | >10000 |
| | 1754-3 | R-2-naphthylmethyl | R-4-hydroxybenzyl | R-butyl | 4-methyl-1-cyclohexyl-methyl | 4078 | >10000 |
| | 1754-4 | R-2-naphthylmethyl | R-2-naphthylmethyl | R-benzyl | cyclohexyl-methyl | >10000 | >10000 |
| | 1754-5 | R-2-naphthylmethyl | R-2-naphthylmethyl | R-benzyl | 4-methyl-1-cyclohexyl-methyl | >10000 | >10000 |
| | 1754-6 | R-2-naphthylmethyl | R-2-naphthylmethyl | R-4-hydroxybenzyl | cyclohexyl-methyl | >10000 | >10000 |
| | 1754-7 | R-2-naphthylmethyl | R-2-naphthylmethyl | R-4-hydroxybenzyl | cyclohexyl-propyl | >10000 | >10000 |
| | 1754-8 | R-2-naphthylmethyl | R-2-naphthylmethyl | R-butyl | cyclohexyl-methyl | >10000 | >10000 |
| | 1754-10 | S-propyl | R-2-naphthylmethyl | R-butyl | 4-methyl-1-cyclohexyl-methyl | >10000 | 135 |
| | 1754-11 | S-isopropyl | R-2-naphthylmethyl | R-propyl | cyclopentyl-methyl | >10000 | 9 |
| | 1754-12 | S-isopropyl | R-2-naphthylmethyl | R-butyl | cycloheptyl-methyl | 2667 | 12 |
| | 1754-13 | S-isopropyl | R-2-naphthylmethyl | R-butyl | cyclobutyl-methyl | 1438 | 6 |
| | 1754-14 | S-isopropyl | R-cyclohexyl | R-4-hydroxybenzyl | 3-methylpentyl | >10000 | 505 |
| | 1754-15 | S-isopropyl | R-cyclohexyl | R-4-hydroxybenzyl | cyclopentyl-methyl | >10000 | 183 |
| | 1754-16 | S-isopropyl | R-cyclohexyl | R-4-hydroxybenzyl | cyclohexyl-methyl | >10000 | 69 |
| | 1754-17 | S-isopropyl | R-4-hydroxybenzyl | R-benzyl | cyclohexyl-methyl | 753 | 10 |
| | 1754-18 | S-isopropyl | R-4-hydroxybenzyl | R-benzyl | 2-Biphenyl-4-yl-ethyl | 355 | 21 |
| | 1754-19 | S-isopropyl | R-4-hydroxybenzyl | R-4-hydroxybenzyl | cyclohexyl-methyl | 3368 | 6 |
| | 1754-20 | S-isopropyl | R-4-hydroxybenzyl | R-4-hydroxybenzyl | 2-Biphenyl-4-yl-ethyl | >10000 | 15 |
| | 1754-21 | S-isopropyl | R-4-hydroxybenzyl | R-butyl | cyclohexyl-methyl | 951 | 5 |
| | 1754-22 | S-isopropyl | R-4-hydroxybenzyl | R-butyl | 2-Biphenyl-4-yl-ethyl | >10000 | 31 |
| | 1754-23 | S-isopropyl | R-propyl | R-benzyl | 2-Biphenyl-4-yl-ethyl | 1053 | 1500 |
| | 1754-24 | S-isopropyl | R-propyl | R-benzyl | 2-Biphenyl-4-yl-ethyl | 330 | 229 |
| | 1754-25 | S-isopropyl | R-propyl | R-4-hydroxybenzyl | cyclohexyl-methyl | 721 | 2400 |
| | 1754-26 | S-isopropyl | R-propyl | R-4-hydroxybenzyl | 2-Biphenyl-4-yl-ethyl | 46 | 70 |
| | 1754-27 | S-isopropyl | R-propyl | R-butyl | cyclohexyl-methyl | 758 | 602 |
| | 1754-28 | S-isopropyl | R-propyl | R-butyl | 2-Biphenyl-4-yl-ethyl | 279 | 58 |

Figure 1EX3 (Table 2) (CONT'D)

| | | | | | |
|---|---|---|---|---|---|
| 1754-29 | S-isopropyl | R-2-naphthylmethyl | R-benzyl | cyclohexyl-methyl | 754 | 8 |
| 1754-30 | S-isopropyl | R-2-naphthylmethyl | R-benzyl | 2-Biphenyl-4-yl-ethyl | >10000 | 51 |
| 1754-31 | S-isopropyl | R-2-naphthylmethyl | R-4-hydroxybenzyl | cyclohexyl-methyl | >10000 | 1 |
| 1754-32 | S-isopropyl | R-2-naphthylmethyl | R-4-hydroxybenzyl | 2-Biphenyl-4-yl-ethyl | >10000 | 21 |
| 1754-33 | S-isopropyl | R-2-naphthylmethyl | R-butyl | cyclohexyl-methyl | 260 | 1 |
| 1754-34 | S-isopropyl | R-2-naphthylmethyl | R-butyl | 2-Biphenyl-4-yl-ethyl | 664 | 11 |
| 1754-35 | S-propyl | R-4-hydroxybenzyl | R-benzyl | cyclohexyl-methyl | 385 | 98 |
| 1754-36 | S-propyl | R-4-hydroxybenzyl | R-benzyl | 2-Biphenyl-4-yl-ethyl | 1123 | 175 |
| 1754-37 | S-propyl | R-4-hydroxybenzyl | R-4-hydroxybenzyl | cyclohexyl-methyl | 436 | 105 |
| 1754-38 | S-propyl | R-4-hydroxybenzyl | R-4-hydroxybenzyl | 2-Biphenyl-4-yl-ethyl | 1792 | 98 |
| 1754-39 | S-propyl | R-4-hydroxybenzyl | R-butyl | cyclohexyl-methyl | 1336 | 163 |
| 1754-40 | S-propyl | R-4-hydroxybenzyl | R-butyl | 2-Biphenyl-4-yl-ethyl | 877 | 265 |
| 1754-41 | S-propyl | R-propyl | R-benzyl | cyclohexyl-methyl | 228 | >10000 |
| 1754-42 | S-propyl | R-propyl | R-benzyl | 2-Biphenyl-4-yl-ethyl | 63 | 591 |
| 1754-43 | S-propyl | R-propyl | R-4-hydroxybenzyl | cyclohexyl-methyl | 90 | >10000 |
| 1754-44 | S-propyl | R-propyl | R-4-hydroxybenzyl | 2-Biphenyl-4-yl-ethyl | 29 | 967 |
| 1754-45 | S-propyl | R-propyl | R-butyl | cyclohexyl-methyl | 966 | 5997 |
| 1754-46 | S-propyl | R-propyl | R-butyl | 2-Biphenyl-4-yl-ethyl | 473 | 410 |
| 1754-47 | S-propyl | R-2-naphthylmethyl | R-benzyl | cyclohexyl-methyl | 1373 | 74 |
| 1754-48 | S-propyl | R-2-naphthylmethyl | R-benzyl | 2-Biphenyl-4-yl-ethyl | >10000 | 512 |
| 1754-49 | S-propyl | R-2-naphthylmethyl | R-4-hydroxybenzyl | cyclohexyl-methyl | 2322 | 33 |
| 1754-50 | S-propyl | R-2-naphthylmethyl | R-4-hydroxybenzyl | 2-Biphenyl-4-yl-ethyl | >10000 | 445 |
| 1754-51 | S-propyl | R-2-naphthylmethyl | R-butyl | cyclohexyl-methyl | 3492 | 44 |
| 1754-52 | S-propyl | R-2-naphthylmethyl | R-butyl | 2-Biphenyl-4-yl-ethyl | >10000 | 454 |
| 1754-56 | S-butyl | R-propyl | R-4-hydroxybenzyl | 2-Biphenyl-4-yl-ethyl | 2 | 1321 |
| 1754-57 | S-benzyl | S-hydroxymethyl | R,S-phenyl | 4-methyl-1-cyclohexyl-methyl | 2964 | >10000 |
| 1754-59 | S-butyl | S-hydroxymethyl | S-2-butyl | 4-methyl-1-cyclohexyl-methyl | >10000 | >10000 |
| 1754-60 | S-butyl | S-hydroxymethyl | S-cyclohexyl | 4-methyl-1-cyclohexyl-methyl | >10000 | >10000 |
| 1754-61 | S-butyl | R-propyl | S-cyclohexyl | 4-methyl-1-cyclohexyl-methyl | 411 | 8519 |
| 1754-64 | S-butyl | S-hydroxymethyl | S-2-butyl | cyclohexyl-methyl | >10000 | >10000 |
| 1754-65 | S-butyl | S-hydroxymethyl | S-2-butyl | 4-tert-butyl-cyclohexyl-methyl | 1847 | >10000 |
| 1754-67 | S-butyl | R-propyl | S-cyclohexyl | cyclobutyl-methyl | 773 | >10000 |

Figure 1EX3 (Table 2) (CONT'D)

| | | | | | |
|---|---|---|---|---|---|
| 1754-68 | S-butyl | R-butyl | S-cyclohexyl | cyclohexyl-methyl | 2336 | >10000 |
| 1754-69 | S-propyl | S-hydroxymethyl | R,S-phenyl | cyclohexyl-methyl | 1953 | >10000 |
| 1754-70 | S-propyl | S-hydroxymethyl | R,S-phenyl | 4-methyl-1-cyclohexyl-methyl | 2232 | >10000 |
| 1754-71 | S-propyl | S-hydroxymethyl | R,S-phenyl | 2-Biphenyl-4-yl-ethyl | 1265 | 3799 |
| 1754-75 | S-butyl | S-hydroxymethyl | R,S-phenyl | cyclohexyl-methyl | 5493 | >10000 |
| 1754-76 | S-butyl | S-hydroxymethyl | R,S-phenyl | 4-methyl-1-cyclohexyl-methyl | 3192 | >10000 |
| 1754-77 | S-butyl | S-hydroxymethyl | R,S-phenyl | 2-Biphenyl-4-yl-ethyl | 1504 | >10000 |
| 1754-78 | S-butyl | S-hydroxymethyl | S-cyclohexyl | 2-Biphenyl-4-yl-ethyl | 797 | >10000 |
| 1754-79 | S-propyl | S-benzyl | R,S-phenyl | cyclohexyl-methyl | 872 | >10000 |
| 1754-80 | S-propyl | S-benzyl | R,S-phenyl | 4-methyl-1-cyclohexyl-methyl | 583 | >10000 |
| 1754-81 | S-propyl | S-benzyl | R,S-phenyl | 2-Biphenyl-4-yl-ethyl | 121 | >10000 |
| 1754-82 | S-propyl | S-benzyl | S-cyclohexyl | cyclohexyl-methyl | 560 | >10000 |
| 1754-83 | S-propyl | S-benzyl | S-cyclohexyl | 4-methyl-1-cyclohexyl-methyl | 410 | >10000 |
| 1754-84 | S-propyl | S-benzyl | S-cyclohexyl | 2-Biphenyl-4-yl-ethyl | 2019 | >10000 |
| 1754-85 | S-propyl | S-isobutyl | R,S-phenyl | cyclohexyl-methyl | 6139 | 3262 |
| 1754-86 | S-propyl | S-isobutyl | R,S-phenyl | 4-methyl-1-cyclohexyl-methyl | 3641 | 5861 |
| 1754-87 | S-propyl | S-isobutyl | R,S-phenyl | 2-Biphenyl-4-yl-ethyl | 663 | >10000 |
| 1754-88 | S-propyl | S-isobutyl | S-cyclohexyl | cyclohexyl-methyl | 145 | >10000 |
| 1754-89 | S-propyl | S-isobutyl | S-cyclohexyl | 4-methyl-1-cyclohexyl-methyl | 463 | >10000 |
| 1754-90 | S-propyl | S-isobutyl | S-cyclohexyl | 2-Biphenyl-4-yl-ethyl | 1133 | >10000 |
| 1754-91 | S-butyl | S-benzyl | R,S-phenyl | cyclohexyl-methyl | 470 | >10000 |
| 1754-93 | S-butyl | S-benzyl | R,S-phenyl | 2-Biphenyl-4-yl-ethyl | 52 | >10000 |
| 1754-94 | S-butyl | S-benzyl | S-cyclohexyl | cyclohexyl-methyl | 375 | >10000 |
| 1754-95 | S-butyl | S-benzyl | S-cyclohexyl | 4-methyl-1-cyclohexyl-methyl | 217 | >10000 |
| 1754-96 | S-butyl | S-benzyl | S-cyclohexyl | 2-Biphenyl-4-yl-ethyl | 595 | >10000 |
| 1754-97 | S-butyl | S-isobutyl | R,S-phenyl | cyclohexyl-methyl | >10000 | 2569 |
| 1754-98 | S-butyl | S-isobutyl | R,S-phenyl | 4-methyl-1-cyclohexyl-methyl | 1684 | >10000 |
| 1754-99 | S-butyl | S-isobutyl | R,S-phenyl | 2-Biphenyl-4-yl-ethyl | 592 | >10000 |
| 1754-100 | S-butyl | S-isobutyl | S-cyclohexyl | cyclohexyl-methyl | 375 | >10000 |
| 1754-101 | S-butyl | S-isobutyl | S-cyclohexyl | 4-methyl-1-cyclohexyl-methyl | 511 | >10000 |
| 1754-102 | S-butyl | S-isobutyl | S-cyclohexyl | 2-Biphenyl-4-yl-ethyl | 677 | >10000 |
| 1754-103 | S-benzyl | S-benzyl | R,S-phenyl | 2-(3-methoxy-phenyl)-ethyl | 15 | >10000 |

Figure 1EX3 (Table 2) (CONT'D)

| | | | | |
|---|---|---|---|---|
| 1754-104 | S-benzyl | S-benzyl | R,S-phenyl | 2-(4-isobutyl-phenyl)-propyl | 7 | >10000 |
| 1754-105 | S-benzyl | S-benzyl | R,S-phenyl | 2-Biphenyl-4-yl-ethyl | 12 | >10000 |
| 1754-106 | S-butyl | S-benzyl | S-2-butyl | 2-(3-methoxy-phenyl)-ethyl | 84 | 3863 |
| 1754-107 | S-butyl | S-benzyl | R,S-phenyl | m-tolylethyl | 20 | >10000 |
| 1754-108 | S-butyl | S-benzyl | R,S-phenyl | p-tolylethyl | 37 | >10000 |
| 1754-109 | S-butyl | S-benzyl | R,S-phenyl | 2-(3-methoxy-phenyl)-ethyl | 16 | >10000 |
| 1754-110 | S-butyl | S-benzyl | R,S-phenyl | 2-(4-methoxy-phenyl)-ethyl | 14 | >10000 |
| 1754-111 | S-butyl | S-benzyl | R,S-phenyl | 2-(4-ethoxy-phenyl)-ethyl | 73 | >10000 |
| 1754-113 | S-benzyl | S-benzyl | R,S-phenyl | phenethyl | 3 | >10000 |
| 1754-114 | S-benzyl | S-benzyl | S-benzyl | 3-(3 4-dimethoxy-phenyl)-propyl | 491 | >10000 |
| 1754-115 | S-benzyl | S-benzyl | S-propyl | phenethyl | 9 | >10000 |
| 1754-116 | S-benzyl | S-benzyl | S-2-butyl | phenethyl | 77 | >10000 |
| 1858-480 | S-butyl | R-propyl | R-4-hydroxybenzyl | 4-methyl-1-cyclohexyl-methyl | >10000 | >10000 |
| 1858-482 | S-butyl | R-propyl | R-4-hydroxybenzyl | cyclohexyl-methyl | 28 | >10000 |
| 1858-483 | S-propyl | R-propyl | R-4-hydroxybenzyl | 4-methyl-1-cyclohexyl-methyl | >10000 | >10000 |
| 1481 1753-101 | S-methyl | R-4-(1-methyl-3-phenyl urea) butyl | 4-phenylbutyl | | 1 | >10000 |
| 1753-102 | S-methyl | R-4-(1-methyl-3-phenyl urea) butyl | 4-methyl-1-cyclohexylmethyl | | 6 | >10000 |
| 1753-103 | S-methyl | R-butyl | 4-phenylbutyl | | 4 | >10000 |
| 1753-104 | S-methyl | R-butyl | 4-methyl-1-cyclohexylmethyl | | 21 | >10000 |

Figure 1EX4 (Table 2)

Table 2. Examples of active compounds for FPR1 and FPR2

| TPI # | Compound | | | | FPR1 | | | FPR2 | | |
|---|---|---|---|---|---|---|---|---|---|---|
| | R1 Functionality | R2 Functionality | R3 Functionality | R4 Functionality | Binding Ki (nM) | Agonist EC50 (nM) | Antagonist IC50 (nM) | Binding Ki (nM) | Agonist EC50 (nM) | Antagonist IC50 (nM) |
| Pyrrolidine bis-diketopiperazine Scaffold | | | | | | | | | | |
| a: 1754-113 | S-benzyl | S-benzyl | R,S-phenyl | phenethyl | 3 | ** | 1070 | * | ** | *** |
| b: 1754-56 | S-butyl | R-propyl | R-4-hydroxy-benzyl | 2-Biphenyl-4-yl-ethyl | 2 | ** | 138 | 1,320 | 1,300 | N.A. |
| c: 1754-26 | S-iso-propyl | R-propyl | R-4-hydroxy-benzyl | 2-Biphenyl-4-yl-ethyl | 46 | ** | 2,680 | 70 | ** | 3,480 |
| d: 1754-20 | S-iso-propyl | R-4-hydroxy-benzyl | R-4-hydroxy-benzyl | 2-Biphenyl-4-yl-ethyl | * | ** | *** | 15 | ** | 466 |
| e: 1754-19 | S-iso-propyl | R-4-hydroxy-benzyl | R-4-hydroxy-benzyl | cyclohexyl-methyl | 3,370 | ** | *** | 6 | ** | 1,410 |
| f: 1754-31 | S-iso-propyl | R-2-naphthyl-methyl | R-4-hydroxy-benzyl | cyclohexyl-methyl | * | ** | *** | 1 | ** | 81 |
| g: 1754-49 | S-propyl | R-2-naphthyl-methyl | R-4-hydroxy-benzyl | cyclohexyl-methyl | 2,320 | ** | *** | 33 | 144 | N.A. |

Figure 1EX4 (Table 2) (CONT'D)

| Polyphenylurea Scaffold | | | | | | |
|---|---|---|---|---|---|---|
| h: | | R₁ | R₂ | R₃ | | |
| 1753-103 | S-methyl | R-butyl | 4-phenyl-butyl | 4 | 131 | N.A. * ** *** |

* Ki greater than 10,000 nM;  No agonistic activity at up to 12 µM; * No antagonistic activity at up to 10 µM; N.A. Not applicable

FIGURE 2EX1
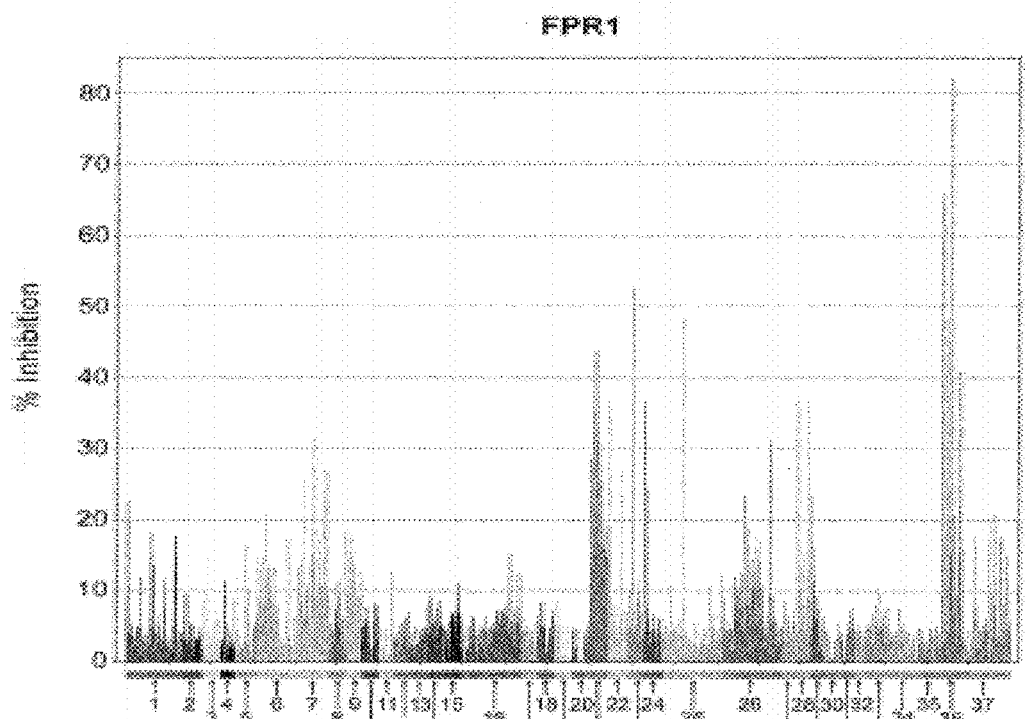
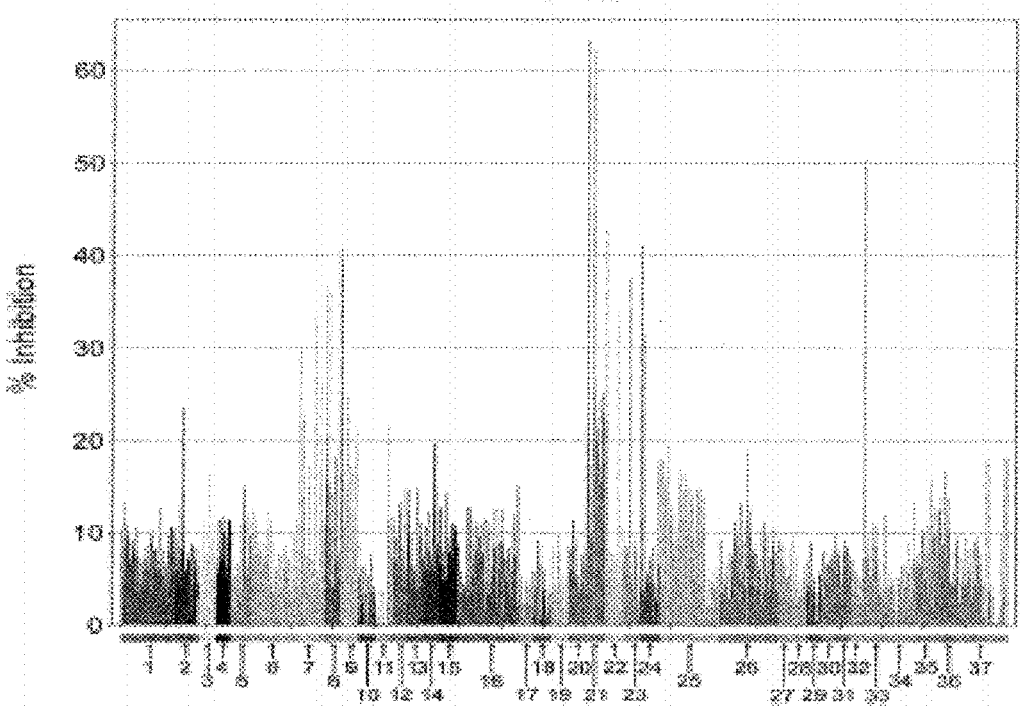

FIGURE 2EX2
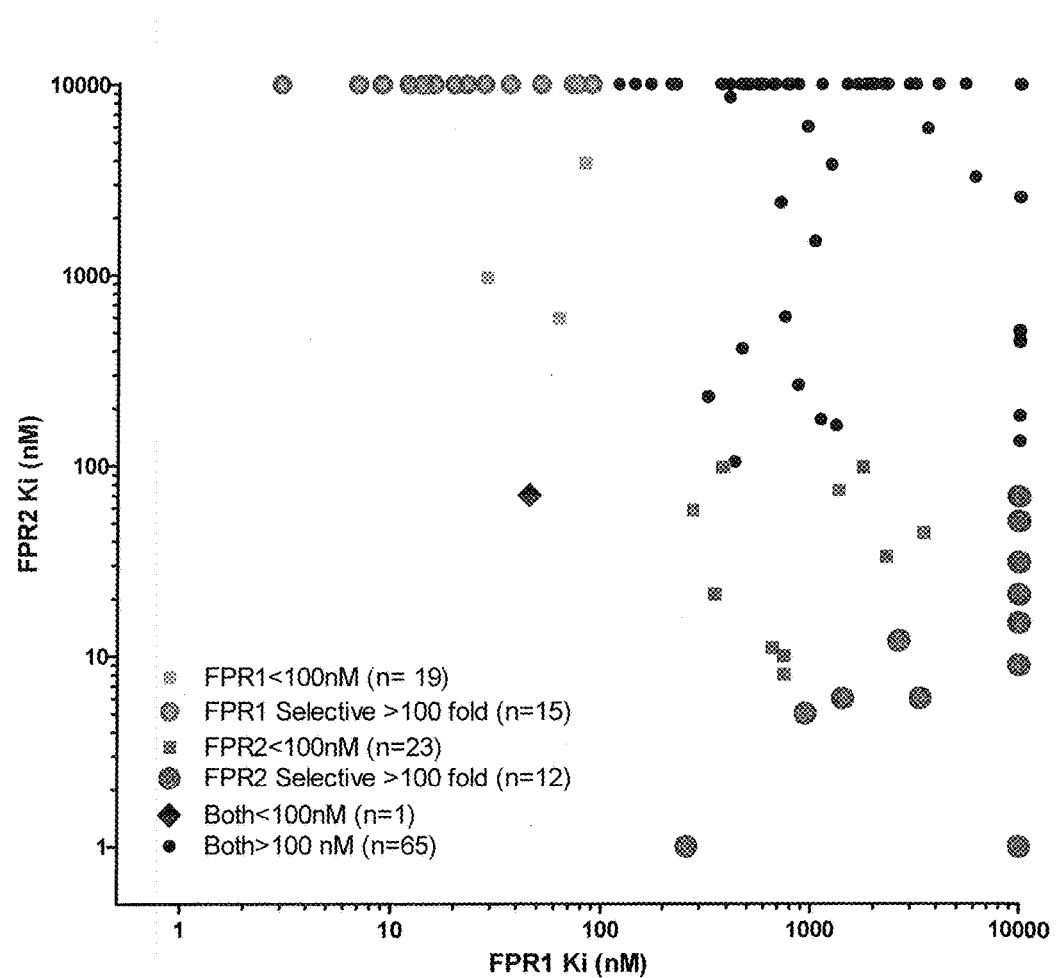

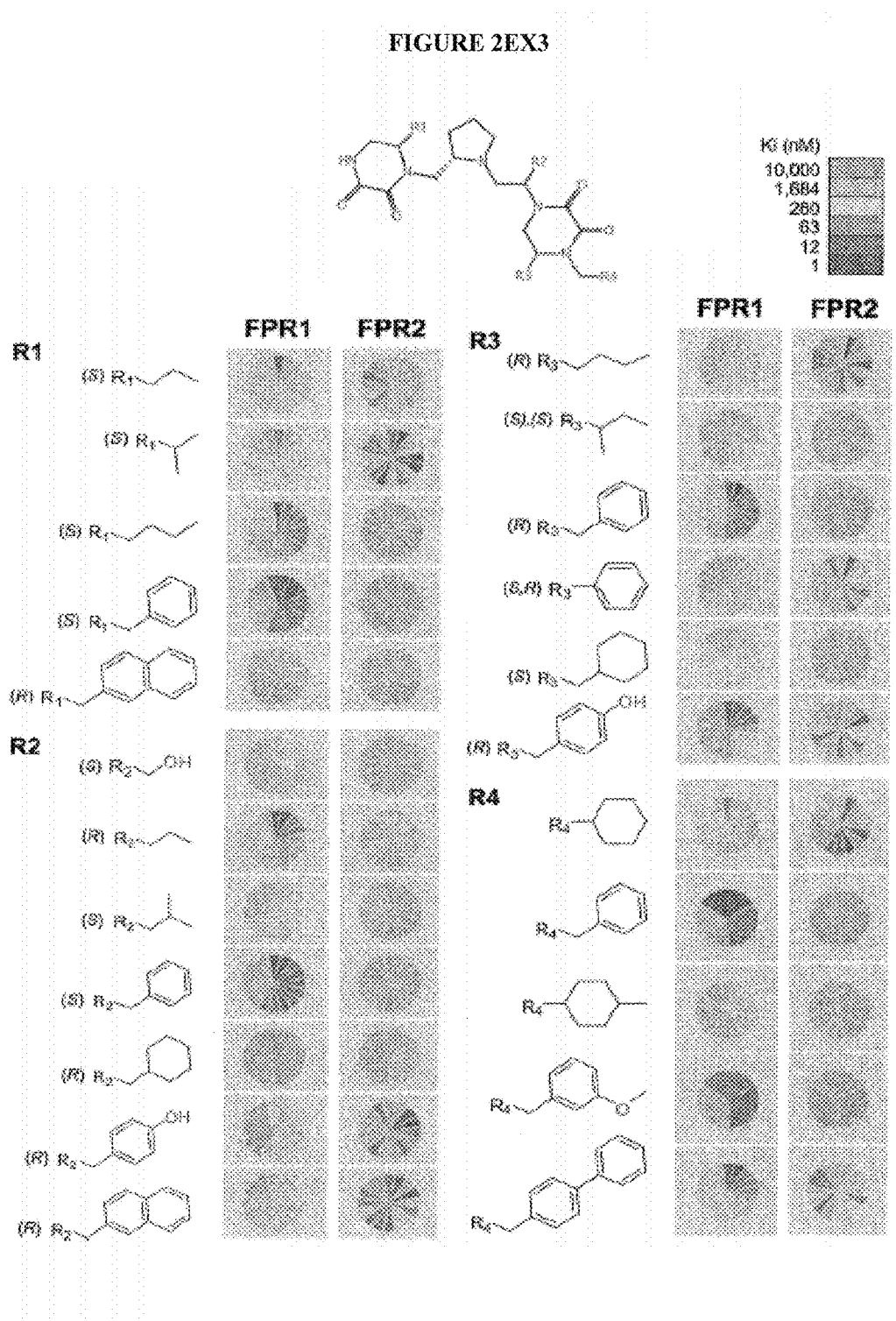
FIGURE 2EX3

FIGURE 2EX4

Table 1. Comparison of FPR1 and FPR2 ligands identified by 4 different screening programs.

| Library | # Samples Tested | # Cmpnds Evaluated | FPR1 # Cmpnds Ki < 1 µM | FPR1 Best ID | FPR1 Best Ki (nM) | FPR1 Best Selectivity | FPR2 # Cmpnds Ki < 1 µM | FPR2 Best ID | FPR2 Best Ki (nM) | FPR2 Best Selectivity | Ref. |
|---|---|---|---|---|---|---|---|---|---|---|---|
| PCL (1) | 880 | 880 | 0 | Sulfinpyrazone | 14,000 | ND | ND | ND | ND | ND | Young, et al., 2005 |
| Focused (2) | 4,324 | 4,324 | 1 | 1910-5441 | 1,000 | ND | ND | ND | ND | ND | Edwards, et al. 2005 |
| MLSM (3) | 24,304 | 24,304 | 7 | 3570-0208 | 95 | >187 | 1 | BB-V-115 | 270 | >20 | Young, et al., 2009 |
| TPIMS (4) | 5,261 | 5 million | 55 | 1754-113 | 3 | >3,333 | 38 | 1754-31 | 1 | >10,000 | Herein |
| 1754 | 806 | 106 | | | | | | | | | |
| 1753 | | 8 | 7 | 1753-101 | 1 | >10,000 | 0 | | | | |

1 Prestwick Chemical Library, a commercial collection of 880 off-patent drugs and alkaloids.
2 FPR-focused, small molecule library based on a computational screen.
3 Small molecule diversity library (NIH Molecular Libraries Small Molecule Repository).
4 TPIMS small molecule mixture based combinatorial libraries. 1754 and 1753 are two sets of individual compounds derived from the deconvolution of selected mixture based libraries.
ND not determined.

FIGURE 2EX5

Table 2. Examples of active compounds for FPR1 and FPR2.

| Compound # | FPR1 | | | FPR2 | | |
|---|---|---|---|---|---|---|
| | Binding Ki (nM) | Agonist EC50 (nM) | Antagonist IC50 (nM) | Binding Ki (nM) | Agonist EC50 (nM) | Antagonist IC50 (nM) |
| Pyrrolidine bis-diketopiperazine scaffold | | | | | | |
| 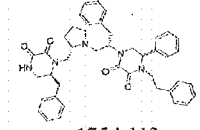 a: 1754-113 | 3 | ** | 1,070 | * |  | * |
| 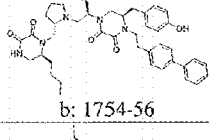 b: 1754-56 | 2 | ** | 139 | 1,320 | 1,300 | N.A. |
| 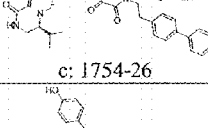 c: 1754-26 | 46 |  | 2,680 | 70 |  | 3,480 |
| 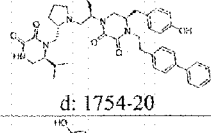 d: 1754-20 | * |  | * | 15 | ** | 452 |
| 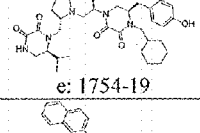 e: 1754-19 | 3,370 |  | * | 6 | ** | 1,410 |
| 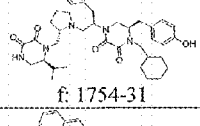 f: 1754-31 | * |  | * | 1 | ** | 81 |
| 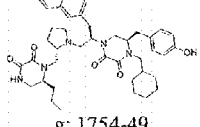 g: 1754-49 | 2,320 |  | * | 33 | 144 | N.A. |
| Polyphenylurea scaffold | | | | | | |
| 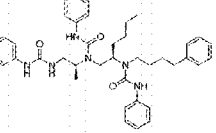 h: 1753-103 | 4 | 131 | N.A. | * |  | * |

\* Ki greater than 10,000 nM; \*\*No agonistic activity at up to 12 μM; \*\*\* No antagonistic activity at up to 10 μM; N.A. not applicable.

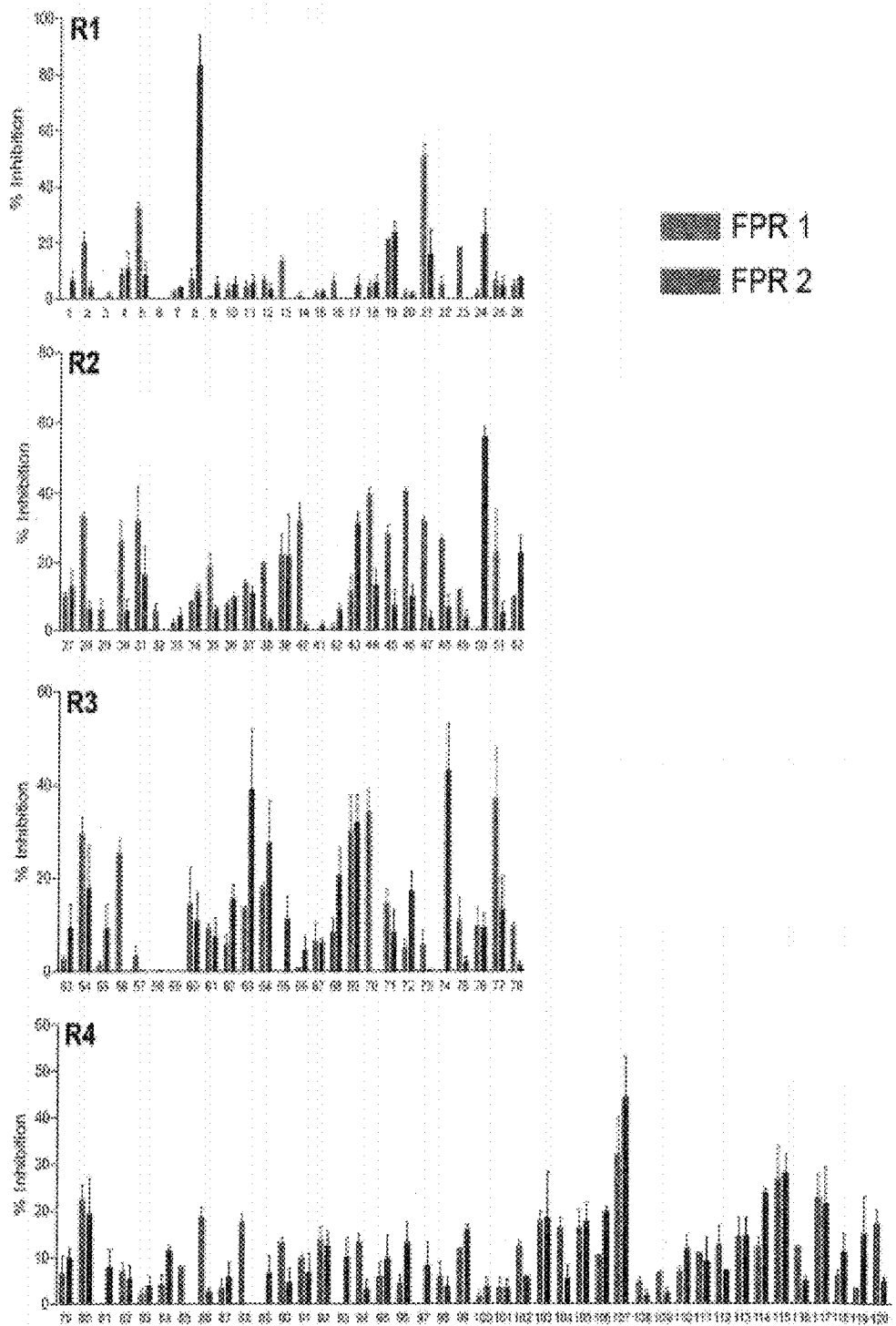
FIGURE 2EX6

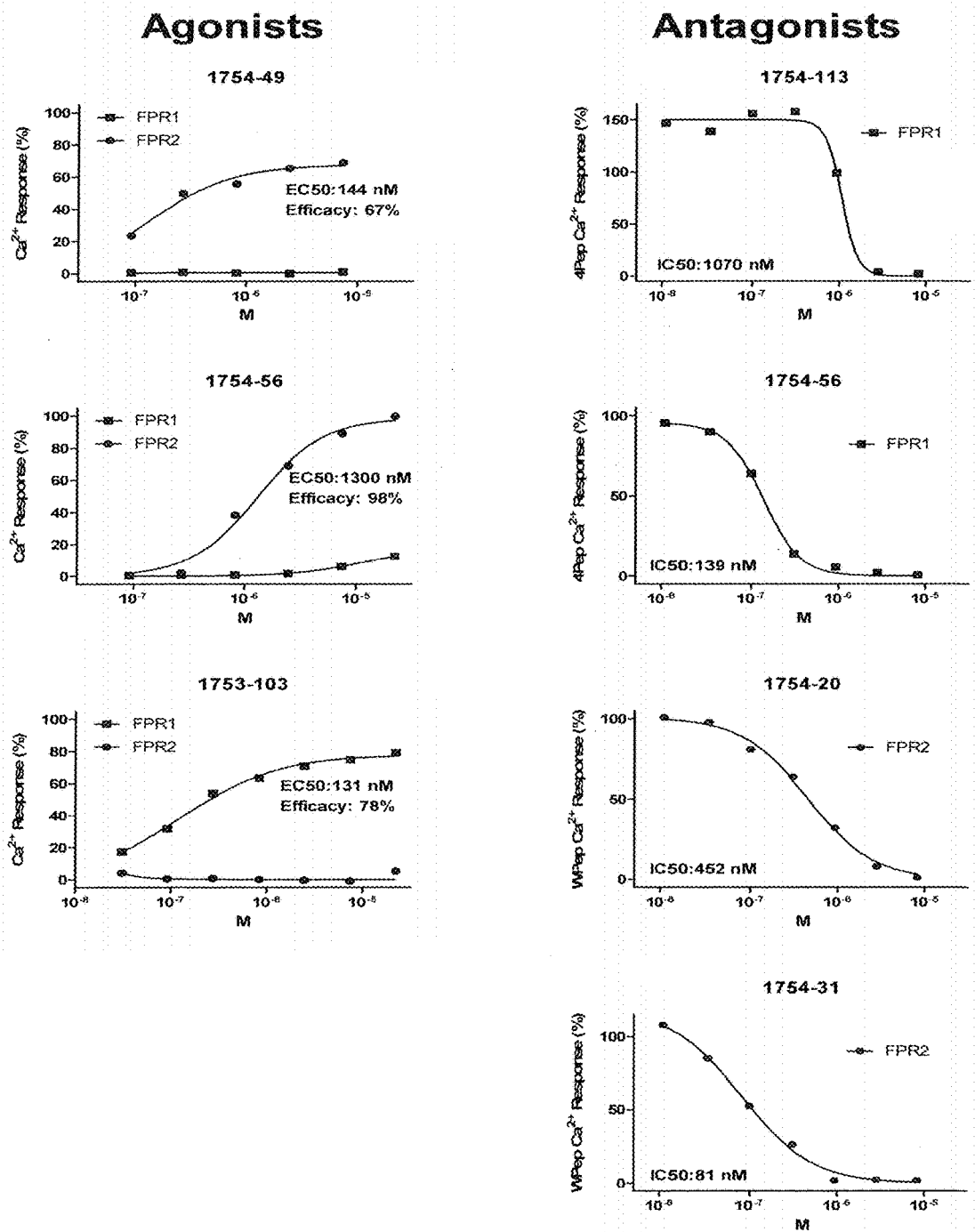
FIGURE 2EX7

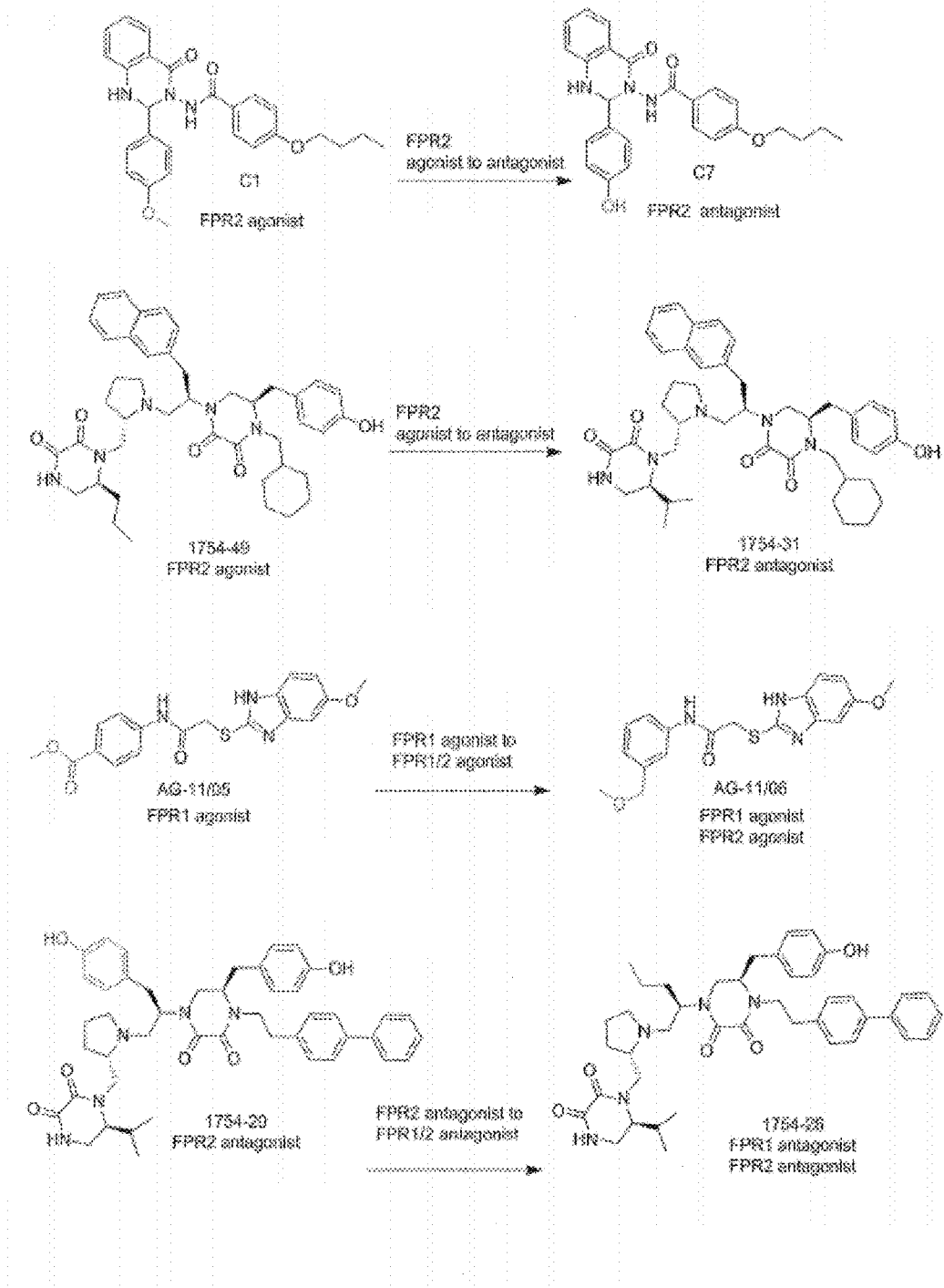
FIGURE 2EX8

FIGURE 2EX9

Table S1. 37 Small Molecule Libraries Tested Against FPR1 and FPR2

| Number | Library | Samples | Compounds/mix | Total | Name | Structure |
|---|---|---|---|---|---|---|
| 1 | 506 | 364 | 230 | 42,320 | Alkylated triamine | 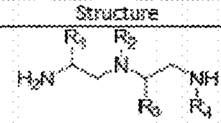 |
| 2 | 531 | 141 | 2,009-2,499 | 102,459 | Bicyclic guanidine | 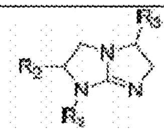 |
| 3 | 882 | 125 | 1,681-1,763 | 72,283 | C-6-acylamino bicyclic guanidine | 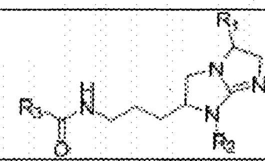 |
| 4 | 886 | 95 | 48 | 4,560 | Benzothiazepene | 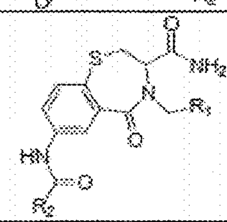 |
| 5 | 914 | 150 | 2,500 | 125,000 | N-acyl triamine | 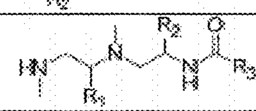 |
| 6 | 923 | 240 | 216,000 | 12,960,000 | L-, D-, unnatural Tetrapeptide | 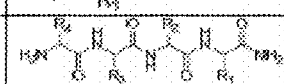 |
| 7 | 924 | 240 | 216,000 | 12,960,000 | L-, D-, unnatural Tetrapeptide | 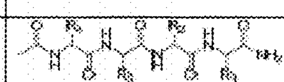 |
| 8 | 1002 | 109 | 1,190-1,400 | 47,600 | Urea-linked bicyclic guanidine | 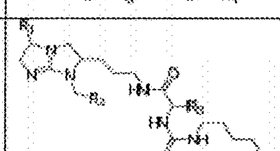 |

FIGURE 2EX9 (CONT'D)
Table S1. 37 Small Molecule Libraries Tested Against FPR1 and FPR2
| 9 | 1169 | 110 | 1,092 – 1,764 | 45,864 | Bis-cyclic guanidine | 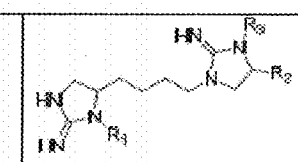 |
| 10 | 1170 | 110 | 1,092 – 1,764 | 45,864 | Bis-diketopiperazine | 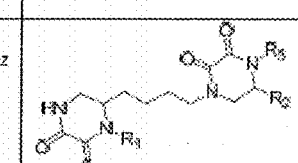 |
| 11 | 1171 | 110 | 1,092 – 1,764 | 45,864 | Bis-cyclic thiourea | 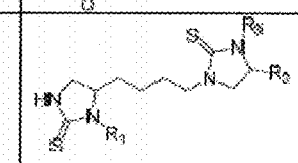 |
| 12 | 1173 | 110 | 1,092 – 1,764 | 45,864 | Bis-piperazine | 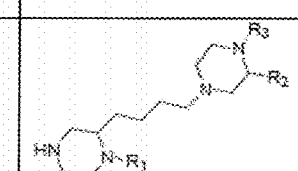 |
| 13 | 1174 | 110 | 1,092 – 1,764 | 45,864 | N-acylated Bis-piperazine |  |
| 14 | 1275 | 116 | 1,258 – 1,865 | 56,610 | Dihydroimidazolyl-butyl-diketopiperazine | 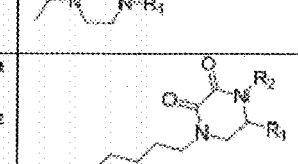 |

FIGURE 2EX9 (CONT'D)

Table S1. 37 Small Molecule Libraries Tested Against FPR1 and FPR2

| 15 | 1276 | 116 | 1,258 – 1,665 | 56,610 | Dihydroimidazolyl-butyl-cyclic thiourea | |
| --- | --- | --- | --- | --- | --- | --- |
| 16 | 1277 | 400 | 41 | 16,400 | Guanidino hydantoin | |
| 17 | 1295 | 107 | 1,224 – 1,332 | 45,288 | Acylated cyclic guanidine | |
| 18 | 1319 | 116 | 1,258 – 1,665 | 56,610 | Dihydroimidazolyl-butyl-cyclic urea | |
| 19 | 1324 | 116 | 1,258 – 1,665 | 56,610 | Dihydroimidazolyl-methyl-diketopiperazine | |
| 20 | 1343 | 120 | 17,576 – 28,392 | 738,192 | Pyrrolidine pentamine | |
| 21 | 1344 | 120 | 17,576 – 28,392 | 738,192 | Pyrrolidine Bis-diketopiperazine | |
| 22 | 1345 | 120 | 17,576 – 28,392 | 738,192 | Pyrrolidine Bis-piperazine | |

FIGURE 2EX9 (CONT'D)

Table S1. 37 Small Molecule Libraries Tested Against FPR1 and FPR2

| 23 | 1346 | 120 | 17,576 - 28,392 | 738,192 | Pyrrolidine Bis-cyclic guanidine | 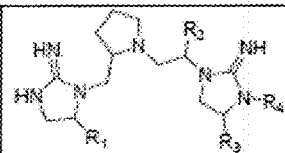 |
| 24 | 1347 | 120 | 17,576 - 28,392 | 738,192 | Pyrrolidine Bis-cyclic thiourea | 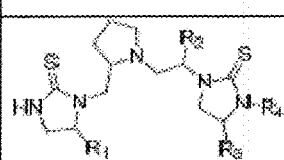 |
| 25 | 1387 | 400 | 40 | 16,000 | Trisubstituted triazinobenzimidazolediones | 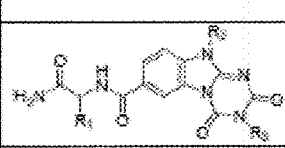 |
| 26 | 1409 | 400 | 27 | 10,800 | Triazinetrione | 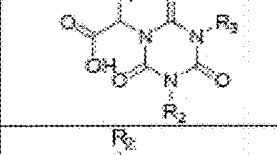 |
| 27 | 1418 | 96 | 783 -1,160 | 31,320 | N-Methyl-1,4,5-trisubstituted-2,3-diketopiperazine | 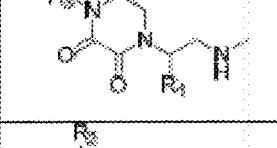 |
| 28 | 1419 | 96 | 783 -1,160 | 31,320 | N-Benzyl-1,4,5-trisubstited-2,3-diketopiperazine | 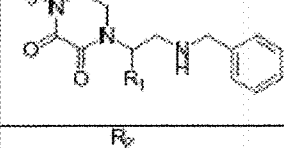 |
| 29 | 1420 | 96 | 783 -1,160 | 31,320 | N-methylated 1,3,4-trisubstituted piperazine | 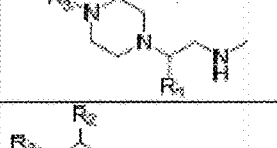 |
| 30 | 1421 | 96 | 783 -1,160 | 31,320 | N-benzylated 1,3,4-trisubstituted piperazine |  |

FIGURE 2EX9 (CONT'D)

Table S1. 37 Small Molecule Libraries Tested Against FPR1 and FPR2

| 31 | 1423 | 36 | 783 - 1,160 | 31,320 | N-Methyltriamine | |
| 32 | 1433 | 74 | 361 - 684 | 12,936 | Nitrosamine | |
| 33 | 1455 | 174 | 3,364 | 195,112 | L-, D-, unnatural Tripeptide | |
| 34 | 1456 | 174 | 3,364 | 195,112 | Tetramine | |
| 35 | 1477 | 174 | 3,364 | 195,112 | Platinum tetramine | |
| 36 | 1481 | 135 | 1,872 - 2,304 | 89,856 | Poly-phenylurea | |
| 37 | 1509 | 319 | 42 | 13,398 | 2-imino-1,3,5-triazino[1,2-a]benzimidazoles | |

FIGURE 2EX10

Table S2. Pyrrolidine bis-diketopiperazine positional scanning library (1344, library 21 in Figure 1) and resulting functionalities at the four positions of diversity.

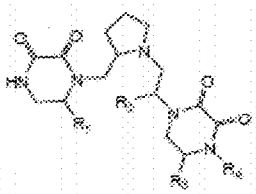

| Number | | Building block | Functionality |
|---|---|---|---|
| 1 | 27 53 | Boc-L-Ala | S-methyl |
| 2 | 28 54 | Boc-L-Phe | S-benzyl |
| 3 | 29 55 | Boc-Gly | Hydrogen |
| 4 | 30 56 | Boc-L-Ile | S-2-butyl |
| 5 | 31 57 | Boc-L-Leu | S-isobutyl |
| 6 | 32 58 | Boc-L-Ser(Bzl) | R-hydroxymethyl |
| 7 | 33 59 | Boc-L-Thr(Bzl) | (R,R)-1-hydroxyethyl |
| 8 | 34 60 | Boc-L-Val | S-isopropyl |
| 9 | 35 61 | Boc-L-Tyr(BrZ) | S-4-hydroxybenzyl |
| 10 | 36 62 | Boc-D-Ala | R-methyl |
| 11 | 37 63 | Boc-D-Phe | R-benzyl |
| 12 | 38 64 | Boc-D-Ile | R-2-butyl |
| 13 | 39 65 | Boc-D-Leu | R-isobutyl |
| 14 | 40 66 | Boc-D-Ser(Bzl) | S-hydroxymethyl |
| 15 | 41 67 | Boc-D-Thr(Bzl) | (S,S)-1-hydroxyethyl |
| 16 | 42 68 | Boc-D-Val | R-isopropyl |
| 17 | 43 69 | Boc-D-Tyr(BrZ) | R-4-hydroxybenzyl |
| 18 | 44 70 | Boc-L-Phenylglycine | S-phenyl |
| 19 | 45 71 | Boc-L-Norvaline | S-propyl |
| 20 | 46 72 | Boc-D-Norvaline | R-propyl |
| 21 | 47 73 | Boc-L-Norleucine | S-butyl |
| 22 | 48 74 | Boc-D-Norleucine | R-butyl |
| 23 | 49 75 | Boc-L-Naphthylalanine | S-2-naphthylmethyl |
| 24 | 50 76 | Boc-D-Naphthylalanine | R-2-naphthylmethyl |
| 25 | 51 77 | Boc-L-Cyclohexylalanine | S-cyclohexyl |
| 26 | 52 78 | Boc-D-Cyclohexylalanine | R-cyclohexyl |
| | 79 | 1-Phenyl-1-cyclopropanecarboxylic acid | (1-Phenyl-cyclopropyl)-methyl |
| | 80 | 2-Phenylbutyric acid | 2-Phenylbutyl |
| | 81 | 3-Phenylbutyric acid | 3-Phenylbutyl |
| | 82 | m-Tolylacetic acid | m-tolylethyl |
| | 83 | 3-Fluorophenylacetic acid | 2-(3-Fluoro-phenyl)-ethyl |
| | 84 | 3-Bromophenylacetic acid | 2-(3-Bromo-phenyl)-ethyl |
| | 85 | α,α,α-Trifluoro-m-Tolyl) acetic acid | 2-(3-Trifluoromethyl-phenyl)-ethyl |
| | 86 | p-Tolylacetic acid | p-tolylethyl |
| | 87 | 4-Fluorophenylacetic acid | 2-(4-Fluoro-phenyl)-ethyl |

FIGURE 2EX10 (CONT'D)

Table S2. Pyrrolidine bis-diketopiperazine positional scanning library (1344, library 21 in Figure 1) and resulting functionalities at the four positions of diversity.

| # | Acid | Functionality |
|---|---|---|
| 88 | 3-Methoxyphenylacetic acid | 2-(3-Methoxy-phenyl)-ethyl |
| 89 | 4-Bromophenylacetic acid | 2-(4-Bromo-phenyl)-ethyl |
| 90 | 4-Methoxyphenylacetic acid | 2-(4-Methoxy-phenyl)-ethyl |
| 91 | 4-Ethoxyphenylacetic acid | 2-(4-Ethoxy-phenyl)-ethyl |
| 92 | 4-Isobutyl-alpha-Methylphenylacetic acid | 2-(4-Isobutyl-phenyl)-propyl |
| 93 | 3,4-Dichlorophenylacetic acid | 3,4-Dichlorophenethyl |
| 94 | 3,5-Bis(Trifluoromethyl)-Phenylacetic acid | 2-(3,5-bis-trifluoromethyl-phenyl)-ethyl |
| 95 | 3-(3,4-Dimethoxyphenyl)-Propionic acid | 3-(3,4-Dimethoxy-phenyl)-propyl |
| 96 | Phenylacetic acid | Phenethyl |
| 97 | 3,4,5-Trimethoxybenzoic acid | 3,4,5-Trimethoxy-benzyl |
| 98 | Butyric acid | Butyl |
| 99 | Heptanoic acid | Heptyl |
| 100 | Isobutyric acid | Isobutyl |
| 101 | 2-Methylbutyric acid | 2-Methylbutyl |
| 102 | Isovaleric acid | 3-Methylbutyl |
| 103 | 3-Methylvaleric acid | 3-Methylpentyl |
| 104 | 4-Methylvaleric acid | 4-Methylpentyl |
| 105 | p-Toluic acid | 4-Methyl-benzyl |
| 106 | Cyclopentanecarboxylic acid | Cyclopentyl-methyl |
| 107 | Cyclohexanecarboxylic acid | Cyclohexyl-methyl |
| 108 | Cyclohexylacetic acid | Cyclohexyl-ethyl |
| 109 | Cyclohexanebutyric acid | Cyclohexyl-butyl |
| 110 | Cycloheptanecarboxylic acid | Cycloheptyl-methyl |
| 111 | 2-Methylcyclopropanecarboxylic acid | (2-Methyl-cyclopropyl)-methyl |
| 112 | Cyclobutanecarboxylic acid | Cyclobutyl-methyl |
| 113 | 3-Cyclopentylpropionic acid | 3-Cyclopentyl-propyl |
| 114 | Cyclohexanepropionic acid | Cyclohexyl-propyl |
| 115 | 4-Methyl-1-Cyclohexanecarboxylic acid | 4-Methyl-1-cyclohexyl-methyl |
| 116 | 4-tert-Butyl-Cyclohexanecarboxylic acid | 4-tert-butyl-cyclohexyl-methyl |
| 117 | 4-Biphenylacetic acid | 2-Biphenyl-4-yl-ethyl |
| 118 | 1-Adamantanecarboxylic acid | Adamantan-1-yl-methyl |
| 119 | 1-Adamantaneacetic acid | 2-Adamantan-1-yl-ethyl |
| 120 | 2-Norbornaneacetic acid | 2-Bicyclo[2.2.1]hept-2-yl-ethyl |

Sublibrary 1: R1 defined for samples 1-26 (28,392 compounds each). Sublibrary 2: R2 defined for samples 27-52 (28,392 compounds each). Sublibrary 3: R3 defined for samples 53-78 (28,392 compounds each). Sublibrary 4: R4 defined for samples 79-120 (17,576 compounds each).

FIGURE 2EX11

Table S3. Analytical information for compounds shown in Table 2.

| Compound | Molecular weight | Molecular weight found | % Peak area at 254nm |
|---|---|---|---|
| a: 1754-113 | 697.86 | 698 | 35:65 * |
| b: 1754-56 | 721.93 | 722 | 99 |
| c: 1754-26 | 707.9 | 708 | 99 |
| d: 1754-20 | 771.94 | 772 | 99 |
| e: 1754-19 | 687.87 | 688 | 99 |
| f: 1754-31 | 721.93 | 722 | 99 |
| g: 1754-49 | 721.93 | 722 | 99 |
| h: 1753-103 | 662.86 | 663 | 99 |

*Compound 1754-113 contains a racemic mixture at the R3 position with a ratio of 35:65.

FIGURE 3EX1
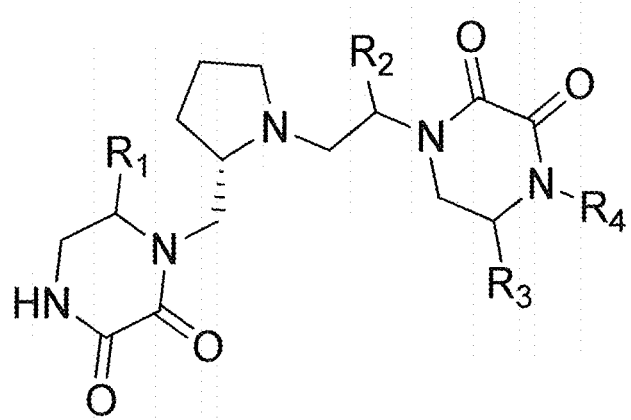

FIGURE 3EX2
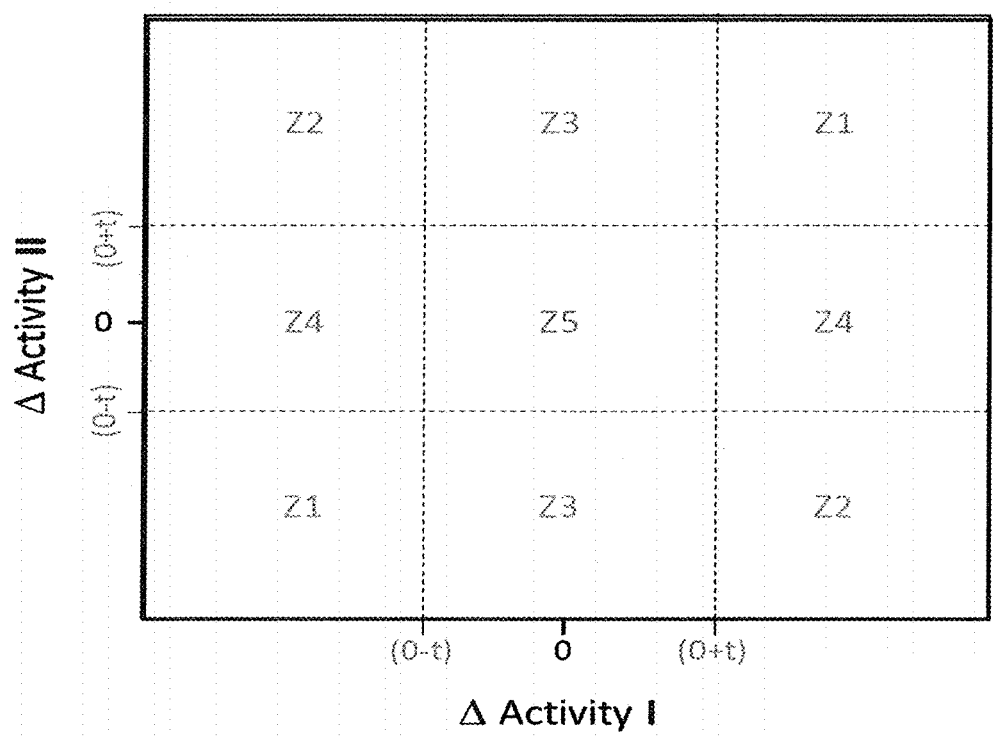

FIGURE 3EX3

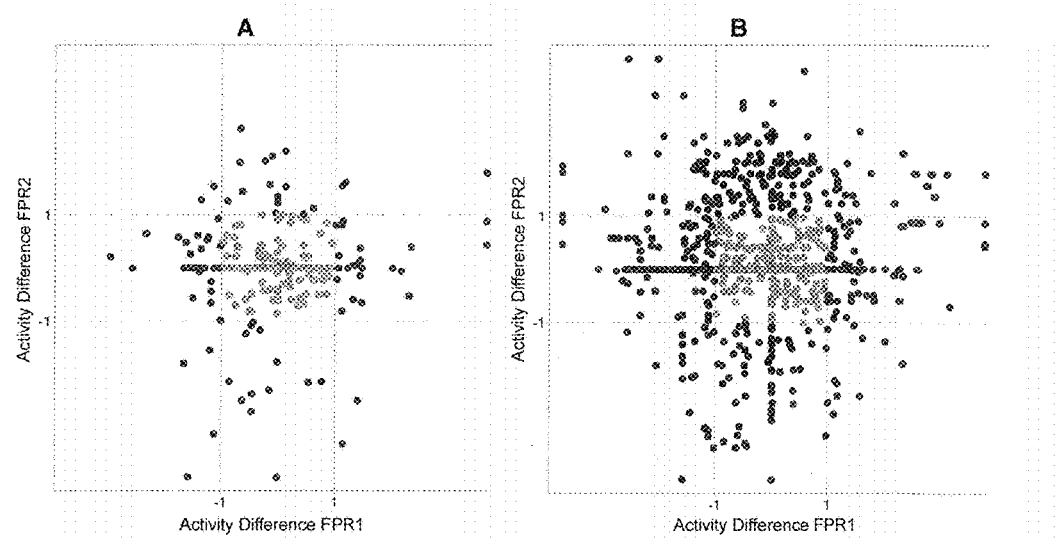

| Region | Interpretation | Single | Double |
|---|---|---|---|
|  |  | 275 pairs total | 896 pairs total |
| Z1 | Substitution changes activity for FPR1 and FPR2 (> 1 log potency) in similar magnitude and direction | 7 (2.5%) | 49 (5.5%) |
| Z2 | Substitution changes activity for FPR1 and FPR2 in similar magnitude but *opposite* direction | 4 (1.4%) | 49 (5.5%) |
| Z3 | Substitution changes activity for FPR2 (> 1 log potency) but not for FPR1 | 27 (9.8%) | 189 (21.1%) |
| Z4 | Substitution changes activity for FPR1 (> 1 log potency) but not for FPR2 | 53 (19.3%) | 242 (27.0%) |
| Z5 | Substitution does not change significantly (≤ 1 log potency) the activity for FPR1 and FPR2 | 184 (66.9%) | 367 (41.0%) |

FIGURE 3EX4
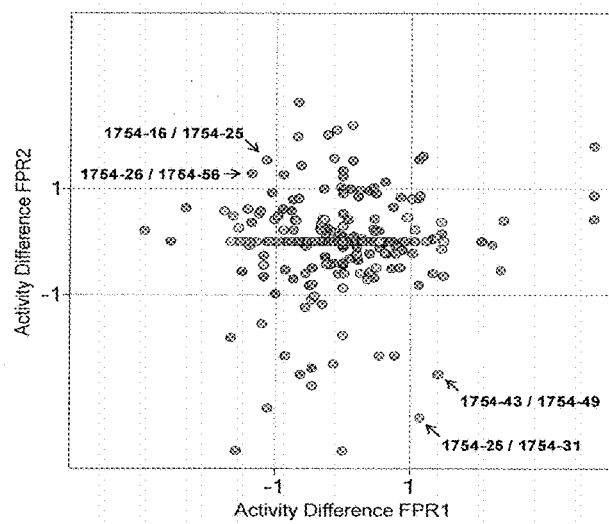
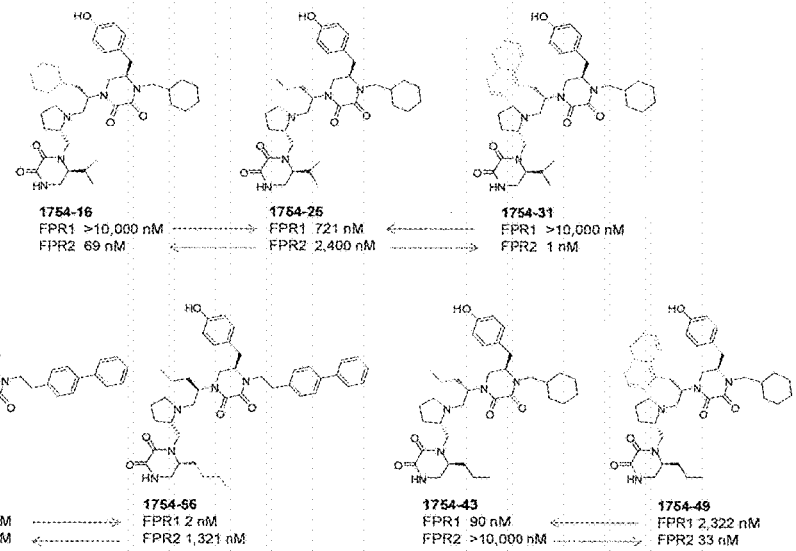
| Pair | ΔpK$_i$ FPR1 | ΔpK$_i$ FPR2 | Mean Similarity | MACCS | GpiDAPH3 | radial |
|---|---|---|---|---|---|---|
| 1754-16 / 1754-25 | -1.14 | 1.54 | 0.736 | 0.917 | 0.936 | 0.354 |
| 1754-25 / 1754-31 | 1.14 | -3.3 | 0.731 | 0.918 | 0.834 | 0.440 |
| 1754-26 / 1754-56 | -1.36 | 1.28 | 0.787 | 0.952 | 0.957 | 0.451 |
| 1754-43 / 1754-49 | 1.41 | -2.48 | 0.745 | 0.949 | 0.840 | 0.447 |

FIGURE 3EX5
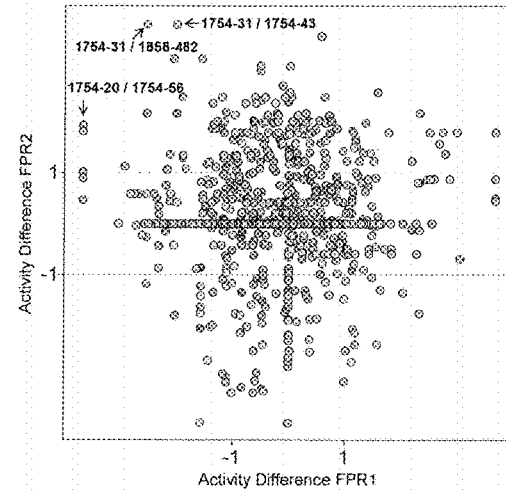
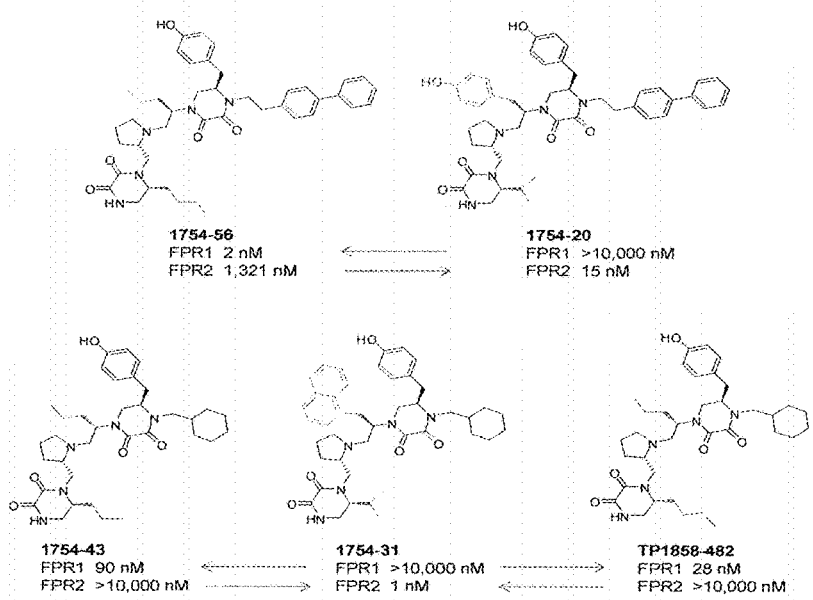
| Pair | ΔpK$_i$ FPR1 | ΔpK$_i$ FPR2 | Mean Similarity | MACCS | GpiDAPH3 | radial |
|---|---|---|---|---|---|---|
| 1754-20 / 1754-56 | -3.7 | 1.93 | 0.699 | 0.934 | 0.835 | 0.329 |
| 1754-31 / 1754-43 | -2.04 | 3.92 | 0.673 | 0.885 | 0.814 | 0.319 |
| 1754-31 / 1858-482 | -2.56 | 3.92 | 0.654 | 0.902 | 0.800 | 0.260 |

FIGURE 3EX6
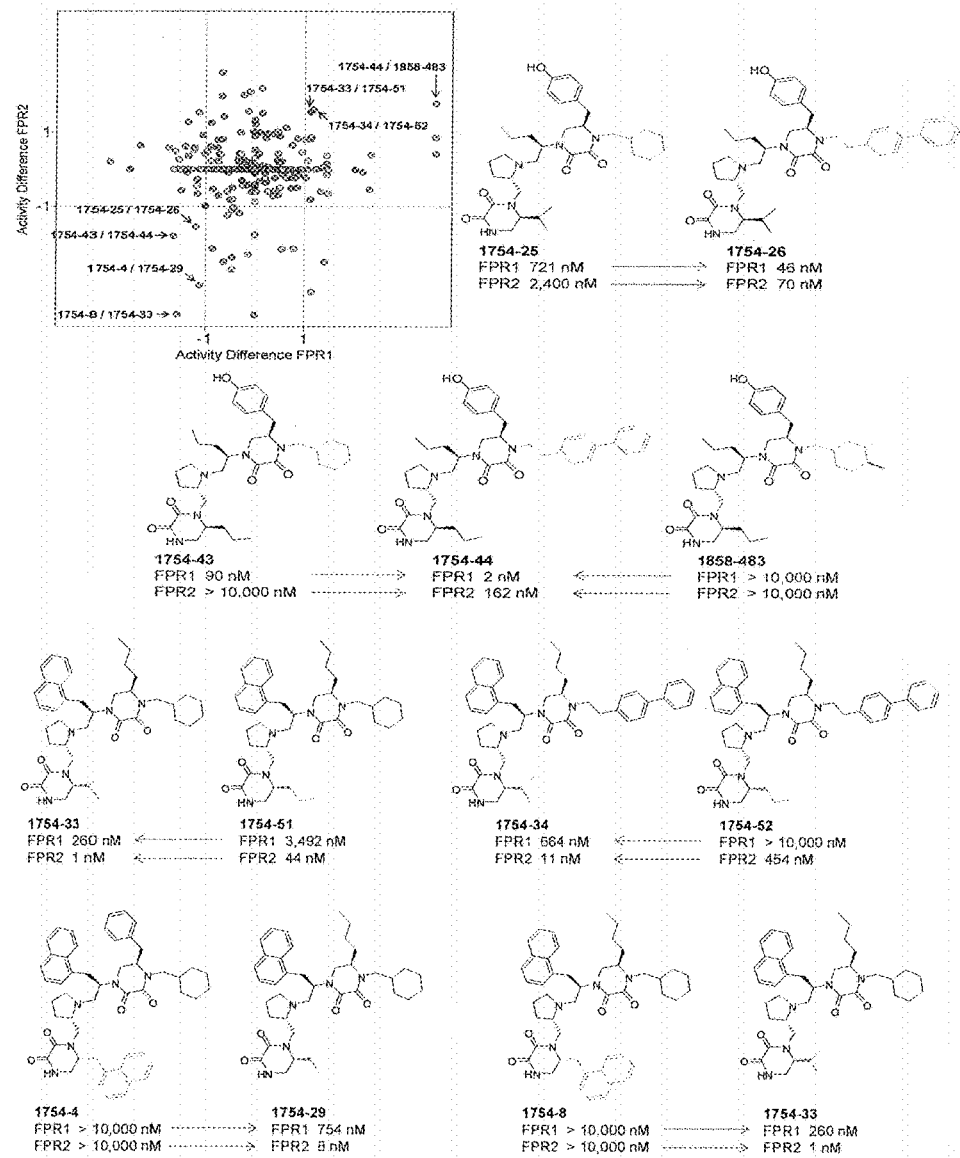
| Pair | ΔpK$_i$ FPR1 | ΔpK$_i$ FPR2 | Mean Similarity | MACCS | GpiDAPH3 | radial |
|---|---|---|---|---|---|---|
| 1754-4 / 1754-29 | -1.12 | -3.11 | 0.765 | 0.889 | 0.917 | 0.488 |
| 1754-8 / 1754-33 | -1.58 | -3.91 | 0.774 | 0.912 | 0.926 | 0.483 |
| 1754-25 / 1754-26 | -1.2 | -1.54 | 0.764 | 0.967 | 0.882 | 0.443 |
| 1754-33 / 1754-51 | 1.12 | 1.55 | 0.829 | 0.947 | 0.983 | 0.556 |
| 1754-34 / 1754-52 | 1.18 | 1.61 | 0.840 | 0.948 | 0.985 | 0.587 |
| 1754-43 / 1754-44 | -1.66 | -1.79 | 0.773 | 0.966 | 0.900 | 0.452 |
| 1754-44 / 1858-483 | 3.7 | 1.79 | 0.756 | 0.934 | 0.887 | 0.447 |

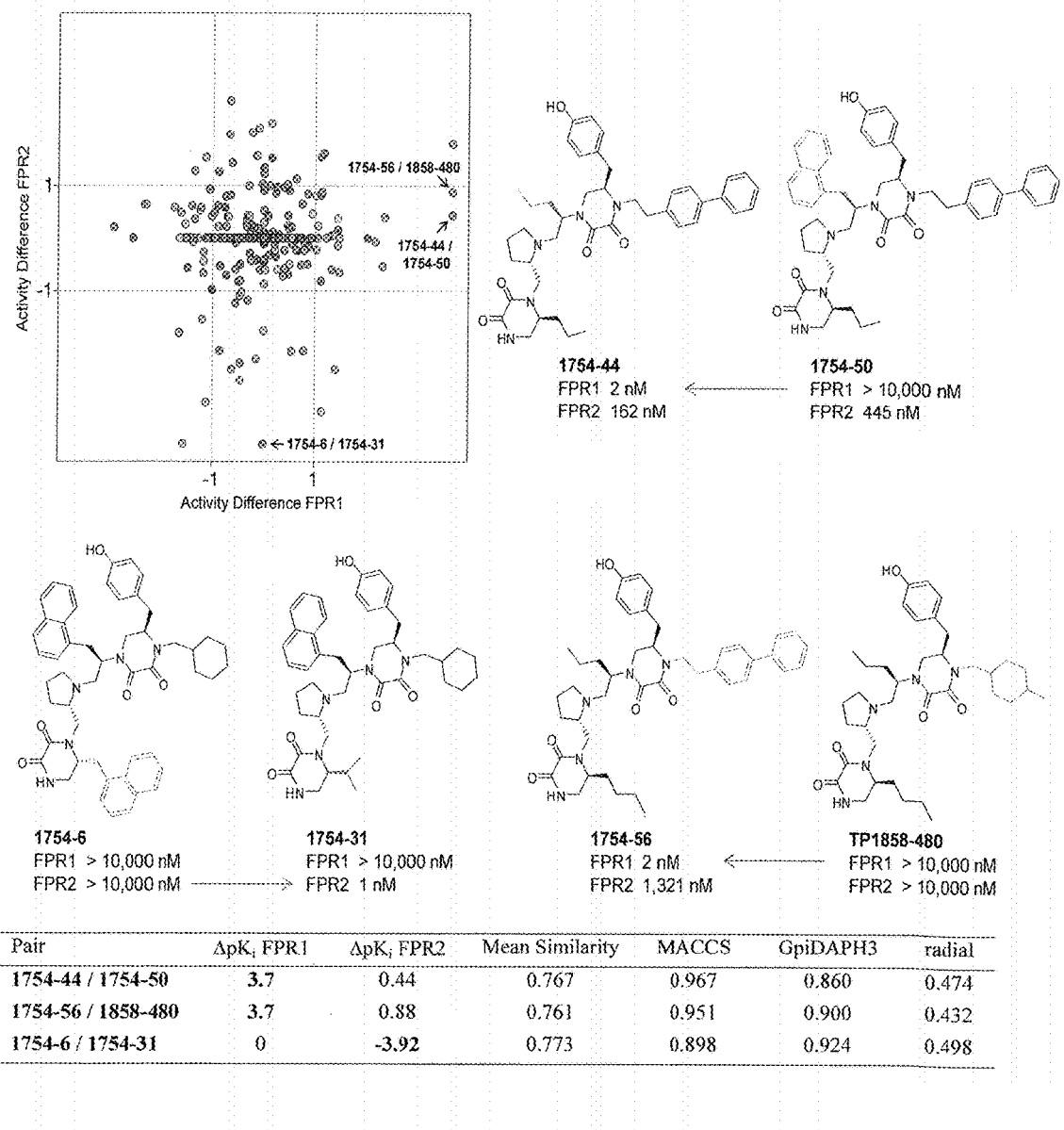
FIGURE 3EX7

FIGURE 3EX8

Table 1. Comparison of FPR1 and FPR2 ligands identified by 4 different screening programs.

| Library | # Samples Tested | # Cmpnds Evaluated | FPR1 # Cmpnds Ki < 1 µM | FPR1 Best ID | FPR1 Best Ki (nM) | FPR1 Best Selectivity | FPR2 # Cmpnds Ki < 1 µM | FPR2 Best ID | FPR2 Best Ki (nM) | FPR2 Best Selectivity | Ref. |
|---|---|---|---|---|---|---|---|---|---|---|---|
| PCL (1) | 880 | 880 | 0 | Sulfinpyrazone | 14,000 | ND | ND | ND | ND | ND | Young, et al., 2005 |
| Focused (2) | 4,324 | 4,324 | 1 | 1910-5441 | 1,000 | ND | ND | ND | ND | ND | Edwards, et al., 2005 |
| MLSM (3) | 24,304 | 24,304 | 7 | 3570-0208 | 95 | >187 | 1 | BB-V-115 | 270 | >20 | Young, et al., 2009 |
| TPIMS (4) 1754 1753 | 5,261 806 | 5 million 106 8 | 55 7 | 1754-113 1753-101 | 3 1 | >3,333 >10,000 | 38 0 | 1754-31 | 1 | >10,000 | Herein |

1 Prestwick Chemical Library, a commercial collection of 880 off-patent drugs and alkaloids.
2 FPR-focused, small molecule library based on a computational screen.
3 Small molecule diversity library (NIH Molecular Libraries Small Molecule Repository).
4 TPIMS small molecule mixture based combinatorial libraries. 1754 and 1753 are two sets of individual compounds derived from the deconvolution of selected mixture based libraries.
ND not determined.

FIGURE 3EX9
Table 2. Examples of active compounds for FPR1 and FPR2.

| Compound # | FPR1 | | | FPR2 | | |
|---|---|---|---|---|---|---|
| | Binding $K_i$ (nM) | Agonist EC50 (nM) | Antagonist IC50 (nM) | Binding $K_i$ (nM) | Agonist EC50 (nM) | Antagonist IC50 (nM) |
| Pyrrolidine bis-diketopiperazine scaffold | | | | | | |
| 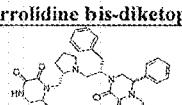 a: 1754-113 | 3 | ** | 1,070 | * |  | * |
| 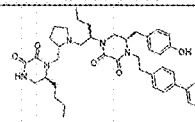 b: 1754-56 | 2 | ** | 139 | 1,320 | 1,300 | N.A. |
| 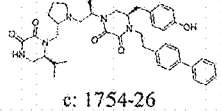 c: 1754-26 | 46 |  | 2,680 | 70 |  | 3,480 |
| 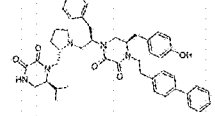 d: 1754-20 | * |  | * | 15 | ** | 452 |
| 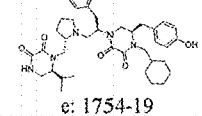 e: 1754-19 | 3,370 |  | * | 6 | ** | 1,410 |
| 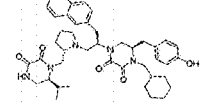 f: 1754-31 | * |  | * | 1 | ** | 81 |
| 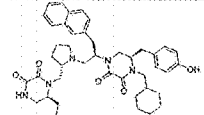 g: 1754-49 | 2,320 |  | * | 33 | 144 | N.A. |
| Polyphenylurea scaffold | | | | | | |
| 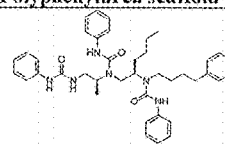 h: 1753-103 | 4 | 131 | N.A. | * |  | * |

* $K_i$ greater than 10,000 nM; No agonistic activity at up to 12 µM; * No antagonistic activity at up to 10 µM; N.A. not applicable.

FIGURE 4EX1
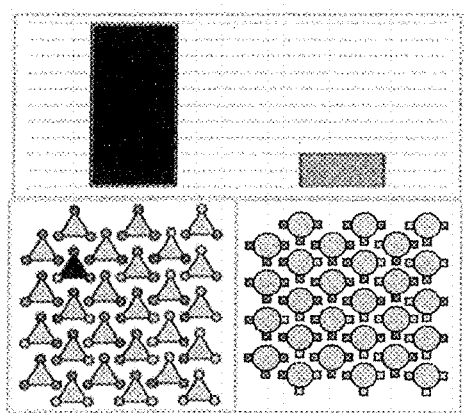
(A) Scaffold Ranking
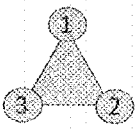
(B) Positional Scanning
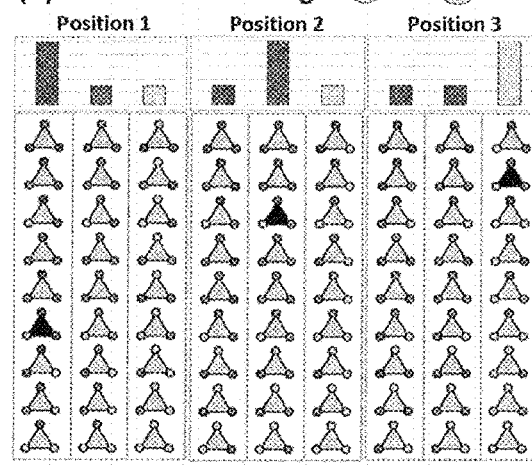
(C) Individual Active Compound
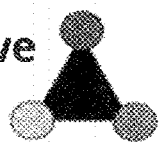

FIGURE 4EX2
32 small-molecule libraries tested against FPR1 and FPR2.
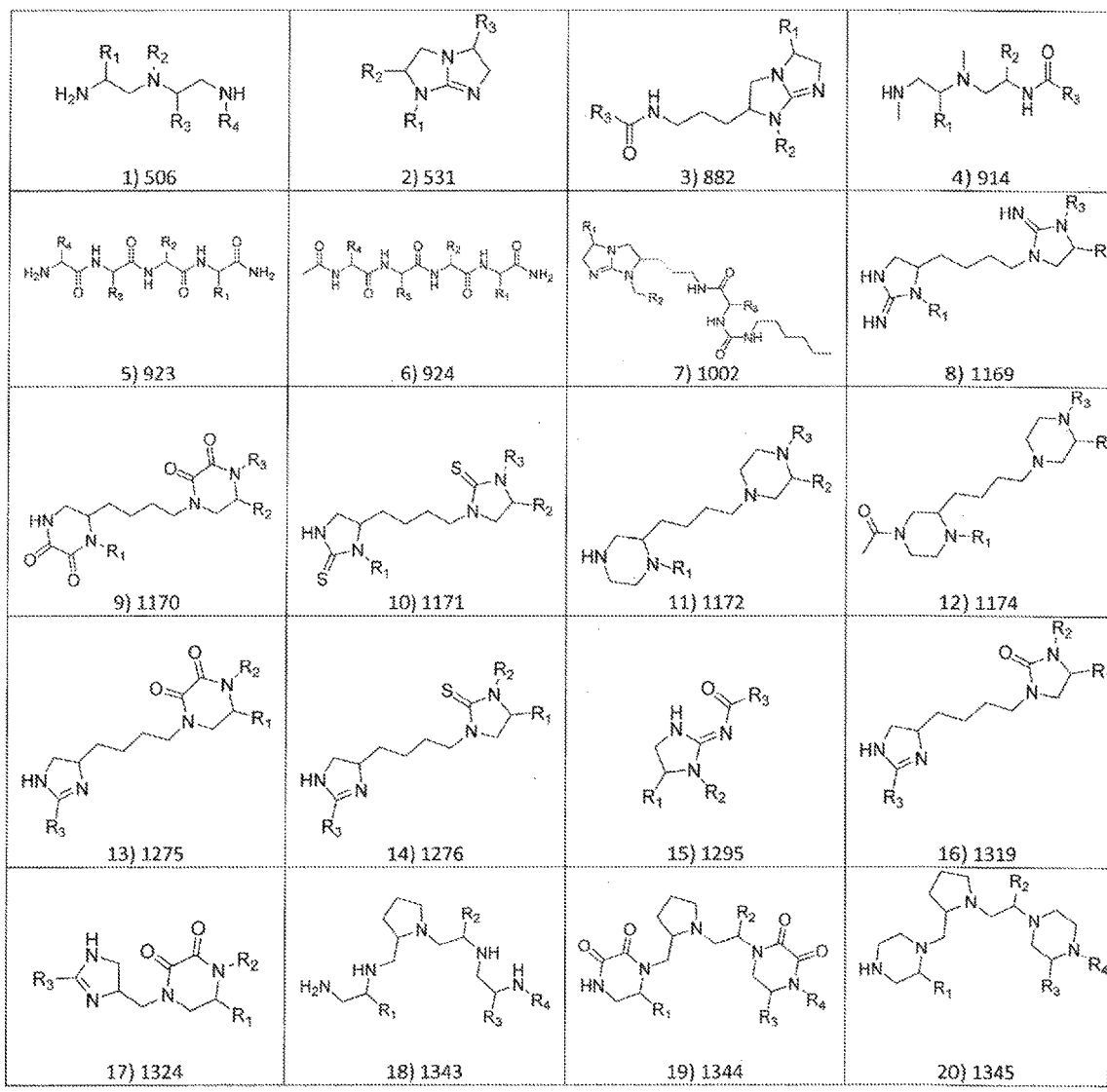

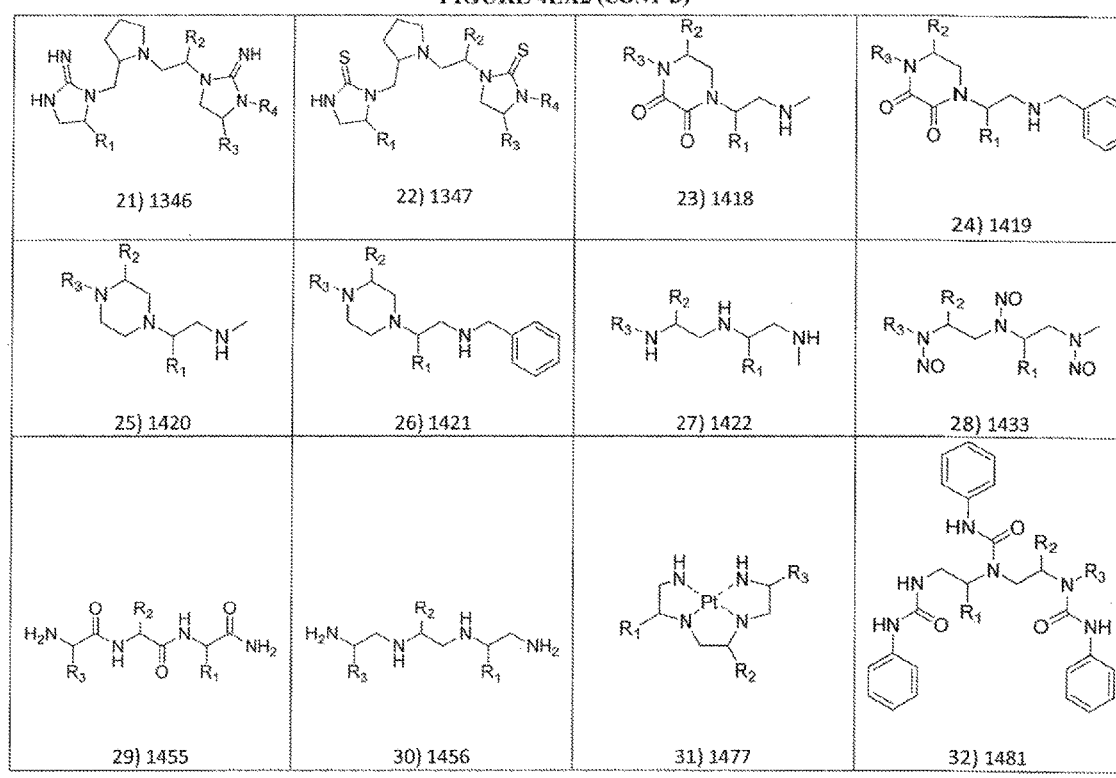
FIGURE 4EX2 (CONT'D)

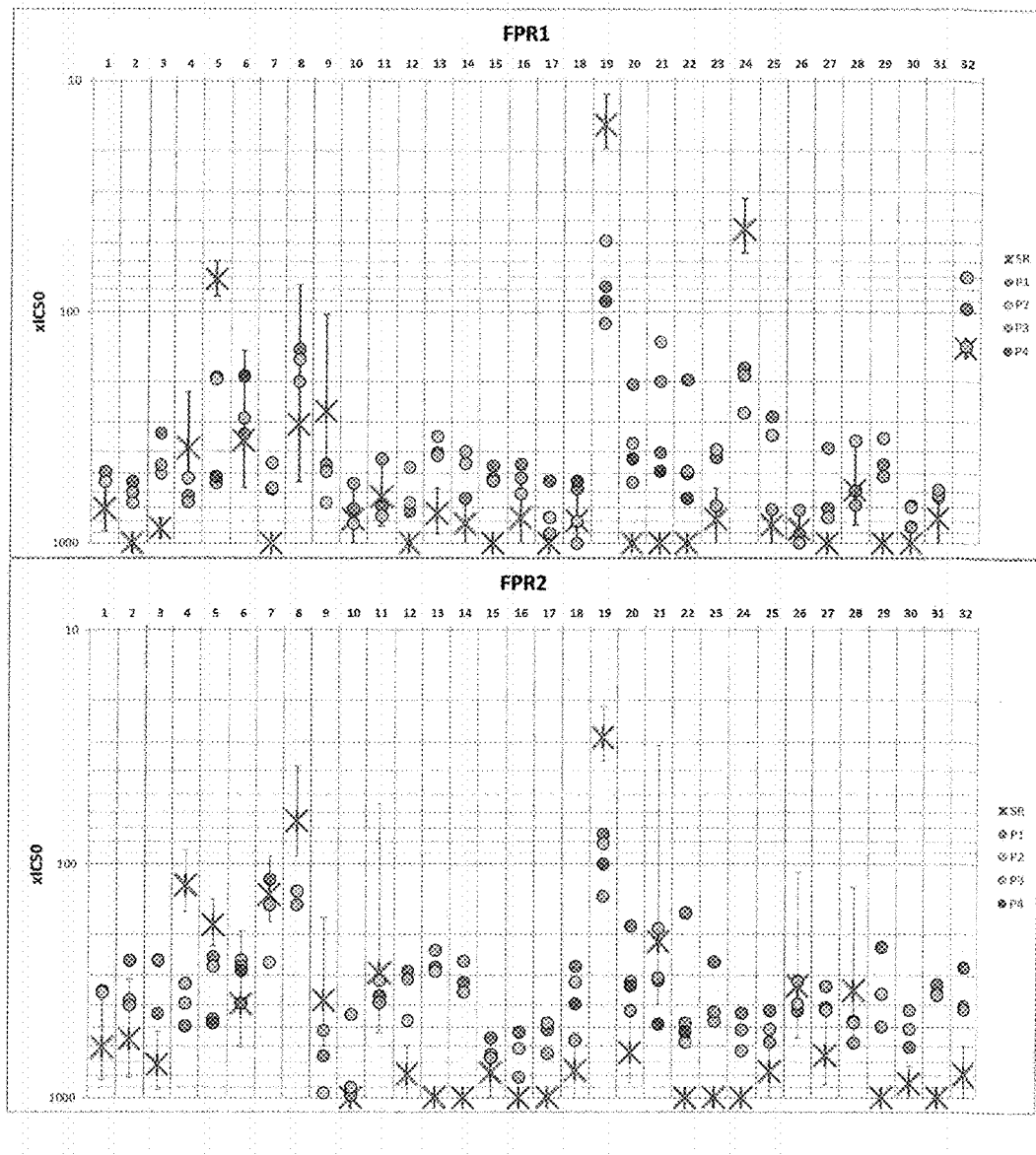
FIGURE 4EX3

FIGURE 4EX4

Table 1. Scaffold Ranking $xIC50s$, compared to the Harmonic Means of Positional Scanning $xIC50s$. Library 19 (red) is the most active in both.

| | FPR1 | | | | | | FPR2 | | | | | |
|---|---|---|---|---|---|---|---|---|---|---|---|---|
| | Scaffold Ranking | | Harmonic Means of Positional Scanning xIC50s | | | | Scaffold Ranking | | Harmonic Means of Positional Scanning xIC50s | | | |
| Library | xIC50 | SEM | P1 | P2 | P3 | P4 | AVG | xIC50 | SEM | P1 | P2 | P3 | P4 | AVG |
| 1 | 708 | 175 | 489 | 540 | NA | NA | 514 | 609 | 226 | 349 | 353 | NA | NA | 351 |
| 2 | 1000 | 0 | 540 | 666 | 601 | NA | 602 | 563 | 252 | 259 | 381 | 402 | NA | 347 |
| 3 | 862 | 85 | 334 | 500 | 458 | NA | 431 | 720 | 200 | 437 | 257 | 260 | NA | 318 |
| 4 | 389 | 166 | 623 | 521 | 662 | NA | 602 | 123 | 37 | 494 | 393 | 324 | NA | 404 |
| 5 | 73 | 13 | 191 | 195 | 547 | 515 | 362 | 183 | 41 | 250 | 273 | 463 | 478 | 366 |
| 6 | 361 | 214 | 336 | 287 | 188 | 190 | 250 | 399 | 206 | 393 | 257 | 273 | 284 | 302 |
| 7 | 1000 | 0 | 583 | 451 | 575 | NA | 536 | 136 | 42 | 117 | 264 | 149 | NA | 177 |
| 8 | 308 | 232 | 145 | 160 | 200 | NA | 168 | 65 | 27 | 131 | 131 | 149 | NA | 137 |
| 9 | 268 | 165 | 456 | 666 | 491 | NA | 538 | 384 | 215 | 660 | 952 | 516 | NA | 709 |
| 10 | 786 | 214 | 707 | 820 | 551 | NA | 692 | 1000 | 0 | 977 | 901 | 440 | NA | 773 |
| 11 | 628 | 216 | 690 | 764 | 431 | NA | 628 | 291 | 236 | 365 | 315 | 392 | NA | 358 |
| 12 | 1000 | 0 | 725 | 666 | 470 | NA | 620 | 798 | 202 | 287 | 467 | 311 | NA | 355 |
| 13 | 744 | 165 | 406 | 344 | 417 | NA | 389 | 1000 | 0 | 276 | 288 | 234 | NA | 266 |
| 14 | 823 | 177 | 638 | 452 | 400 | NA | 497 | 1000 | 0 | 321 | 354 | 260 | NA | 312 |
| 15 | 1000 | 0 | 462 | 523 | 538 | NA | 508 | 781 | 219 | 555 | 652 | 672 | NA | 626 |
| 16 | 779 | 221 | 456 | 612 | 520 | NA | 529 | 1000 | 0 | 525 | 615 | 819 | NA | 653 |
| 17 | 1000 | 0 | 538 | 773 | 909 | NA | 740 | 1000 | 0 | 510 | 478 | 646 | NA | 545 |
| 18 | 803 | 197 | 581 | 799 | 1000 | 538 | 730 | 764 | 236 | 274 | 319 | 566 | 396 | 389 |
| 19 | 15 | 4 | 77 | 49 | 112 | 90 | 82 | 29 | 8 | 74 | 82 | 137 | 100 | 98 |
| 20 | 1000 | 0 | 206 | 368 | 545 | 431 | 387 | 640 | 218 | 184 | 319 | 424 | 331 | 315 |
| 21 | 1000 | 0 | 405 | 134 | 200 | 488 | 307 | 215 | 184 | 314 | 188 | 306 | 485 | 323 |
| 22 | 1000 | 0 | 197 | 500 | 487 | 640 | 456 | 1000 | 0 | 162 | 577 | 479 | 521 | 435 |
| 23 | 790 | 210 | 424 | 394 | 685 | NA | 501 | 1000 | 0 | 262 | 469 | 430 | NA | 387 |
| 24 | 44 | 12 | 174 | 273 | 188 | NA | 212 | 1000 | 0 | 433 | 627 | 512 | NA | 524 |
| 25 | 839 | 161 | 284 | 341 | 711 | NA | 445 | 771 | 229 | 424 | 508 | 579 | NA | 504 |
| 26 | 871 | 129 | 912 | 994 | 717 | NA | 874 | 332 | 223 | 424 | 397 | 316 | NA | 379 |
| 27 | 1000 | 0 | 705 | 772 | 389 | NA | 622 | 660 | 218 | 411 | 420 | 334 | NA | 388 |
| 28 | 588 | 242 | 593 | 361 | 684 | NA | 546 | 349 | 223 | 469 | 475 | 581 | NA | 508 |
| 29 | 1000 | 0 | 455 | 351 | 510 | NA | 439 | 1000 | 0 | 227 | 359 | 497 | NA | 361 |
| 30 | 1000 | 0 | 688 | 696 | 849 | NA | 744 | 866 | 134 | 606 | 509 | 421 | NA | 512 |
| 31 | 782 | 218 | 630 | 614 | 584 | NA | 609 | 1000 | 0 | 329 | 357 | 364 | NA | 350 |
| 32 | 144 | 12 | 97 | 70 | 141 | NA | 102 | 800 | 200 | 277 | 407 | 418 | NA | 367 |

FIGURE 4EX5

Table 2. Indices of Differentiation and Deconvolutability for the 32 libraries against both targets. The most differentiated positions and the most deconvolutable libraries are shown in red.

| Library | FPR1 | | | | | | FPR2 | | | | | |
|---|---|---|---|---|---|---|---|---|---|---|---|---|
| | $I_{DIFF}$ | | | | | $I_{DECON}$ | $I_{DIFF}$ | | | | | $I_{DECON}$ |
| | P1 | P2 | P3 | P4 | AVG | | P1 | P2 | P3 | P4 | AVG | |
| 1 | 4.55 | 1.01 | NA | NA | 2.78 | 5.41 | 2.55 | 2.05 | NA | NA | 2.30 | 6.56 |
| 2 | 3.70 | 0.65 | 0.80 | NA | 1.72 | 2.85 | 10.60 | 1.00 | 1.40 | NA | 4.33 | 12.47 |
| 3 | 0.15 | 1.00 | 1.30 | NA | 0.82 | 1.90 | 1.80 | 4.10 | 0.55 | NA | 2.15 | 6.77 |
| 4 | 3.60 | 3.30 | 1.70 | NA | 2.87 | 4.76 | 4.50 | 1.40 | 0.09 | NA | 2.00 | 4.95 |
| 5 | 6.00 | 0.26 | 0.15 | 6.10 | 3.13 | 8.64 | 0.80 | 0.38 | 0.70 | 0.13 | 0.50 | 1.37 |
| 6 | 1.85 | 15.20 | 14.10 | 4.70 | 8.96 | 35.82 | 1.65 | 4.60 | 15.70 | 9.50 | 7.86 | 26.03 |
| 7 | 0.09 | 1.15 | 1.40 | NA | 0.88 | 1.64 | 9.10 | 0.26 | 10.95 | NA | 6.77 | 38.33 |
| 8 | 0.07 | 0.58 | 0.00 | NA | 0.21 | 1.27 | 8.30 | 0.68 | 0.44 | NA | 3.14 | 22.89 |
| 9 | 1.80 | 1.50 | 1.00 | NA | 1.43 | 2.67 | 1.05 | 0.15 | 2.20 | NA | 1.13 | 1.60 |
| 10 | 0.90 | 2.30 | 7.00 | NA | 3.40 | 4.91 | 0.60 | 3.70 | 10.50 | NA | 4.93 | 6.38 |
| 11 | 0.04 | 2.70 | 0.00 | NA | 0.91 | 1.45 | 0.03 | 0.43 | 0.70 | NA | 0.38 | 1.07 |
| 12 | 1.30 | 0.00 | 0.00 | NA | 0.43 | 0.70 | 0.17 | 0.12 | 3.80 | NA | 1.36 | 3.84 |
| 13 | 0.18 | 2.85 | 0.58 | NA | 1.20 | 3.09 | 1.45 | 0.00 | 5.05 | NA | 2.17 | 8.14 |
| 14 | 0.48 | 0.00 | 3.55 | NA | 1.34 | 2.70 | 4.85 | 4.80 | 0.23 | NA | 3.29 | 10.57 |
| 15 | 0.00 | 0.11 | 2.05 | NA | 0.72 | 1.42 | 0.03 | 0.53 | 0.31 | NA | 0.29 | 0.46 |
| 16 | 1.65 | 0.16 | 0.83 | NA | 0.88 | 1.66 | 2.60 | 0.95 | 0.20 | NA | 1.25 | 1.91 |
| 17 | 2.75 | 1.85 | 5.23 | NA | 3.28 | 4.43 | 3.60 | 1.80 | 0.00 | NA | 1.80 | 3.31 |
| 18 | 0.05 | 2.55 | 0.00 | 0.44 | 0.76 | 1.04 | 2.05 | 0.00 | 0.29 | 0.00 | 0.58 | 1.50 |
| 19 | 15.23 | 0.10 | 5.38 | 1.29 | 5.50 | 67.09 | 41.45 | 36.85 | 0.74 | 0.18 | 19.81 | 201.44 |
| 20 | 25.05 | 0.85 | 0.90 | 19.70 | 11.63 | 30.00 | 36.35 | 0.00 | 0.01 | 23.50 | 14.96 | 47.54 |
| 21 | 4.25 | 43.85 | 0.00 | 0.63 | 12.18 | 39.72 | 0.03 | 24.95 | 1.15 | 0.14 | 6.57 | 20.30 |
| 22 | 8.38 | 0.02 | 1.70 | 1.75 | 2.96 | 6.49 | 13.78 | 0.56 | 2.75 | 1.05 | 4.53 | 10.43 |
| 23 | 3.65 | 0.01 | 1.30 | NA | 1.65 | 3.30 | 0.01 | 0.80 | 2.70 | NA | 1.17 | 3.02 |
| 24 | 21.95 | 4.30 | 13.20 | NA | 13.15 | 62.15 | 2.45 | 0.02 | 1.25 | NA | 1.24 | 2.36 |
| 25 | 4.60 | 1.70 | 0.88 | NA | 2.39 | 5.37 | 2.10 | 0.00 | 0.01 | NA | 0.70 | 1.40 |
| 26 | 2.75 | 0.65 | 0.07 | NA | 1.16 | 1.32 | 0.93 | 0.04 | 1.50 | NA | 0.82 | 2.17 |
| 27 | 0.02 | 0.46 | 0.53 | NA | 0.34 | 0.54 | 0.40 | 0.00 | 0.02 | NA | 0.14 | 0.36 |
| 28 | 0.19 | 0.00 | 0.85 | NA | 0.35 | 0.64 | 1.70 | 1.60 | 0.00 | NA | 1.10 | 2.17 |
| 29 | 1.45 | 1.60 | 0.63 | NA | 1.23 | 2.79 | 41.00 | 1.45 | 7.35 | NA | 16.60 | 46.00 |
| 30 | 2.80 | 0.09 | 0.85 | NA | 1.25 | 1.67 | 0.04 | 0.68 | 4.50 | NA | 1.74 | 3.40 |
| 31 | 0.20 | 0.00 | 0.80 | NA | 0.33 | 0.55 | 2.30 | 0.01 | 2.85 | NA | 1.72 | 4.92 |
| 32 | 12.35 | 57.70 | 18.40 | NA | 29.48 | 287.83 | 3.00 | 0.74 | 0.60 | NA | 1.45 | 3.94 |

FIGURE 4EX6
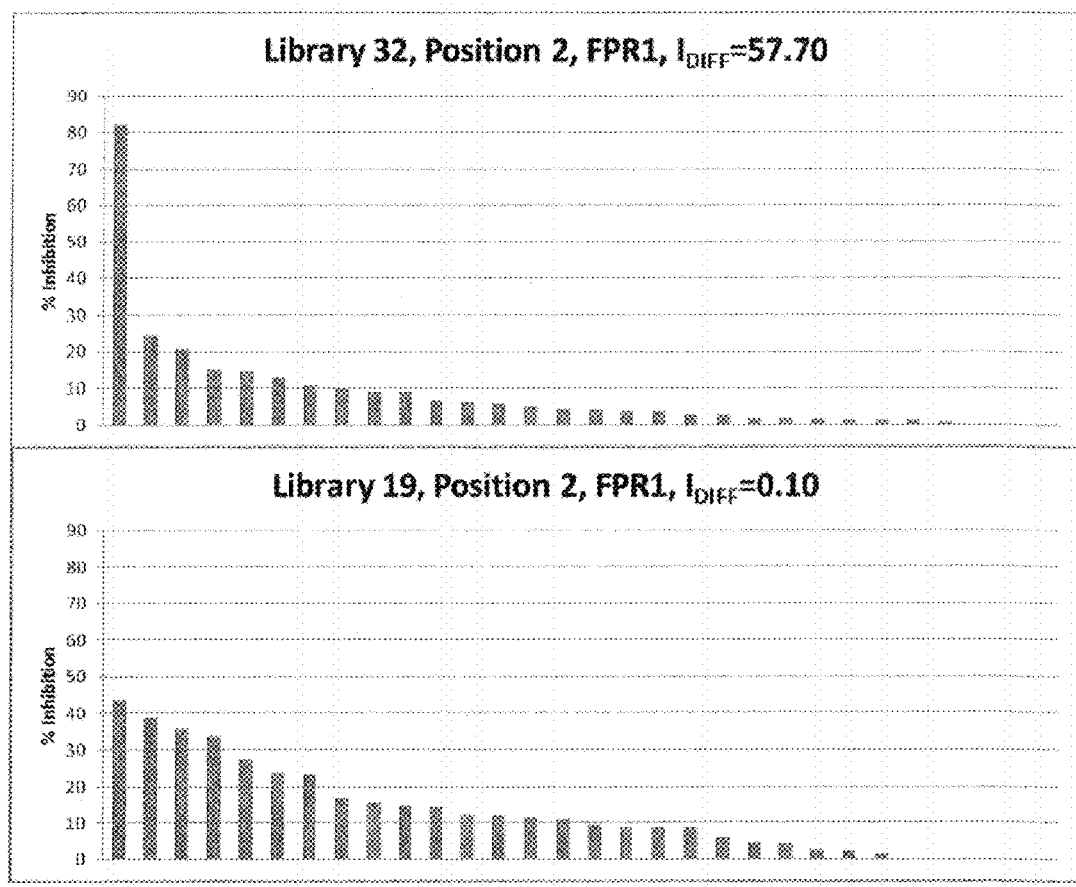

FIGURE 4EX7
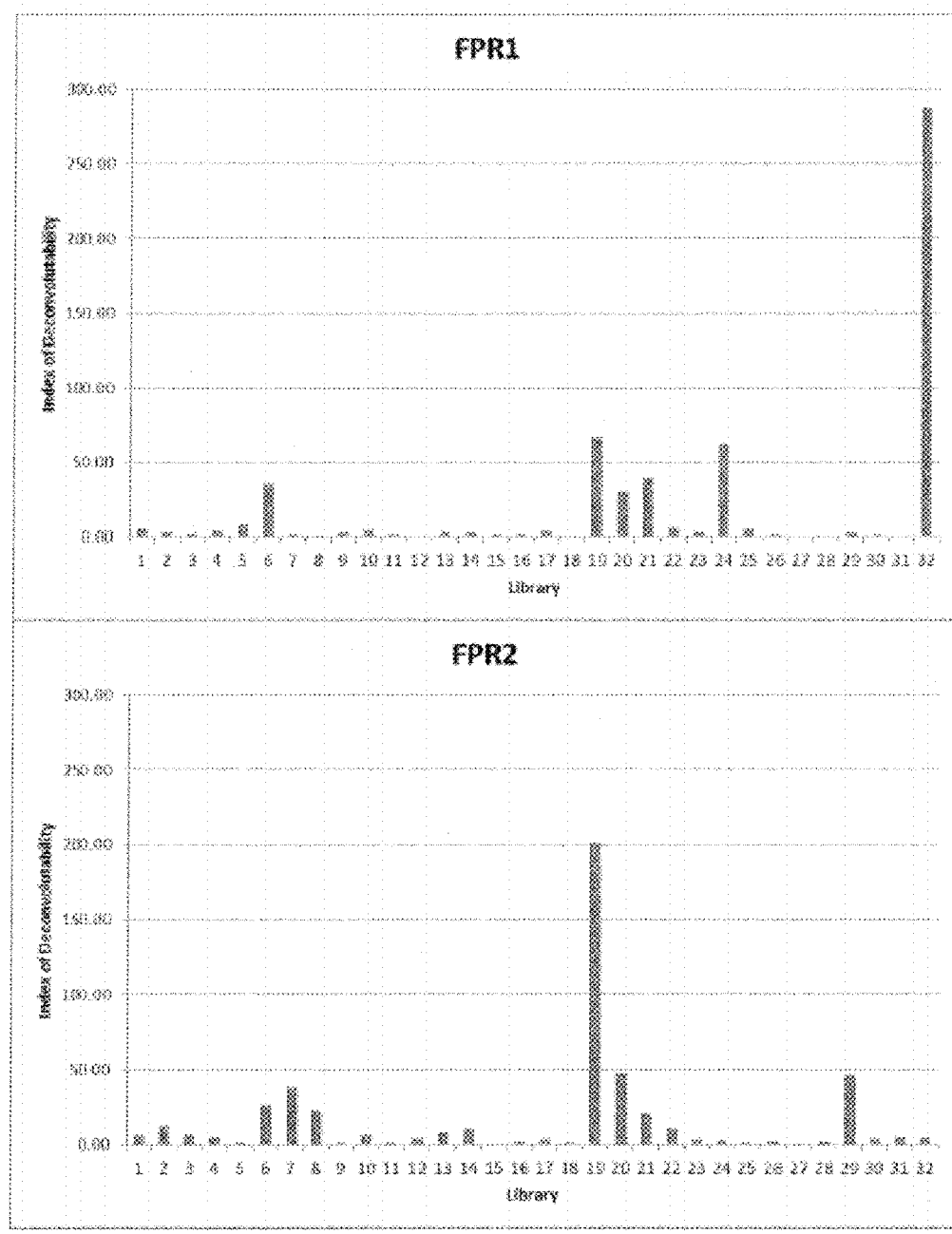

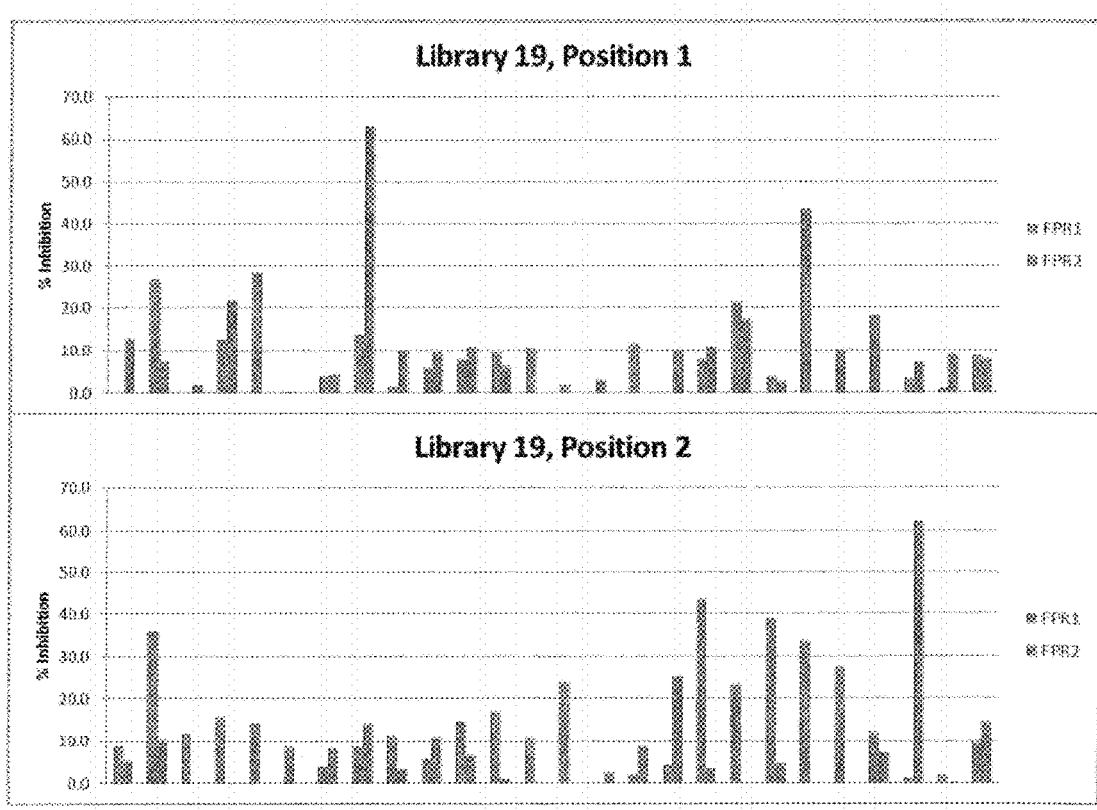
FIGURE 4EX8

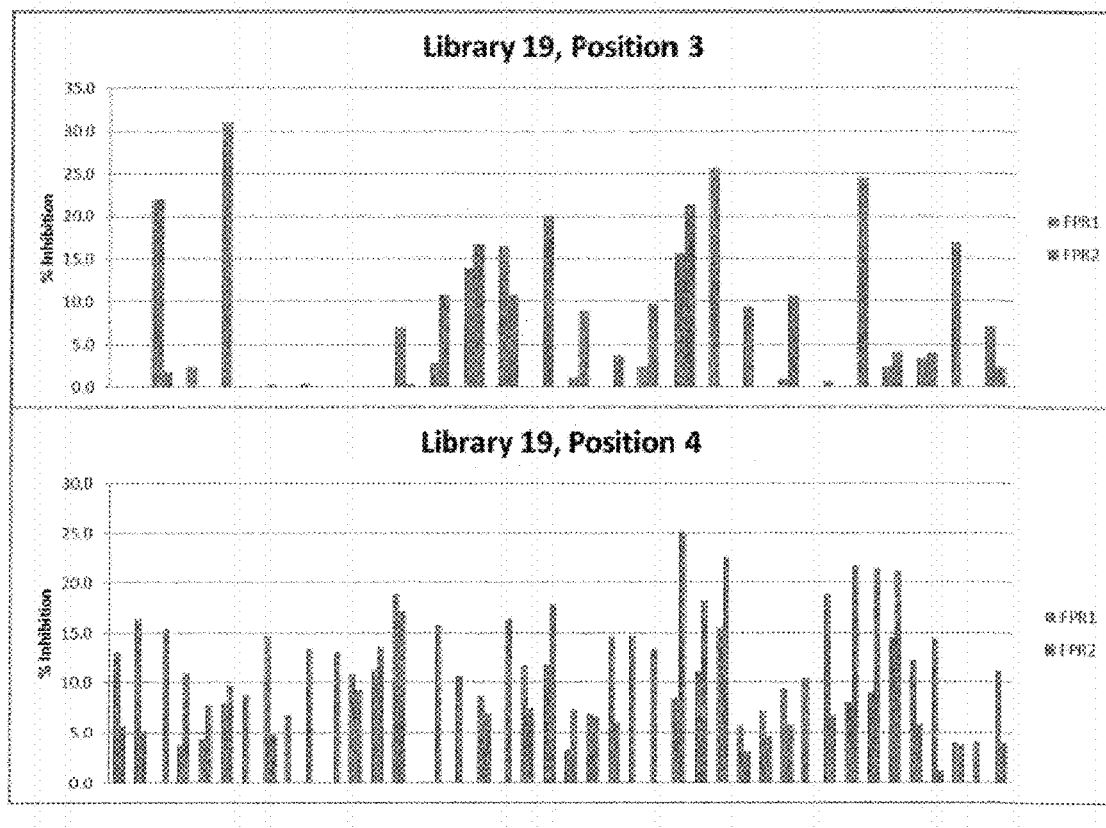
FIGURE 4EX8 (CONT'D)

HIGH-AFFINITY SMALL MOLECULE FORMYLPEPTIDE RECEPTOR LIGANDS FROM SCREENING OF COMBINATORIAL MIXTURE-BASED LIBRARIES

The present application is a continuation application of U.S. patent application Ser. No. 14/174,564 filed Feb. 6, 2014, now U.S. Pat. No. 9,310,364, which claims the benefit of priority of U.S. Provisional Application Ser. No. 61/762,083, filed Feb. 7, 2013, entitled "High Affinity Small Molecule Formylpeptide Receptor Ligands from Screening of Combinatorial Mixture-Based Libraries", both of which are herein incorporated by reference in its entirety.

RELATED APPLICATIONS AND GOVERNMENT SUPPORT

The subject matter of this application was supported by National Institute of Health (NIH) grant numbers 1R01DA031370, U54MH084690, U54MH074425, R01HG005066, P30 CA 118100, U54 RR026083, and 1RO1DA031370, and Department of Defense (DOD) Contract HDTRA1-13-C-005. Consequently, the United States retains rights in the invention.

FIELD OF THE INVENTION

The present invention provides novel methods and assays for high-throughput screening of combinatorial libraries to identify FPR1 agonists and/or FPR2 antagonists by positional scanning deconvolution.

The invention also provides novel FPR1 agonists and FPR2 antagonists, related pharmaceutical compositions and methods of treating FPR1 and FPR2-related disorders.

BACKGROUND OF THE INVENTION

Formyl peptide receptors (FPRs) are a small group of G protein-coupled receptors that are known to be important in host defense and inflammation, and numerous studies have been carried out to identify small molecule ligands in order to characterize the structure and function of these receptors [1, 2]. The two receptors of the FPR family that are addressed here are FPR1, linked to antibacterial inflammation [3] and malignant glioma cell metastasis [4-6], and FPR2 (formally known as FPRL-1), linked to chronic inflammation in systemic amyloidosis, Alzheimer's disease, prion diseases and ischemia/reperpusion injury [7-12]. These two receptors were originally identified to be primarily expressed in myeloid cells, with varying distribution among myeloid cell subsets [1]. However, subsequent work has elucidated expression of functional receptors in a diversity of tissues including endothelial cells, hepatocytes, glial cells, astrocytes, platelets and olfactory neurons [1, 13].

There have been numerous studies to identify naturally occurring and synthetic ligands for each of these receptors (reviewed in [1, 11, 14]). Of particular relevance to the present work have been concerted efforts by a number of groups to develop progressively more potent small molecule agonists or antagonists for each receptor with therapeutic endpoints in mind. We previously reported the use of a fluorescent ligand competition assay and high-throughput flow cytometry to identify a series of novel small molecule ligands for FPR1 and FPR2 [15-17]. The most potent ligands identified were 3570-0208 and BB-V-115, with ligand binding inhibition constants (Ki) of 95 nM and 270 nM for FPR1 and FPR2, respectively [16]. Each was a selective antagonist of the intracellular $Ca^{2+}$ response mediated by its target receptor with an $IC_{50}$ value of 430 nM for FPR1 (3570-0208) and 940 nM for FPR2 (BB-V-115). Recently, two separate groups have identified more potent small molecule FPR1 antagonists with $Ca^{2+}$ response $IC_{50}$ values of 398 nM [18] and 4 nM [19]. Small molecule FPR1 agonists have been identified in a number of recent studies [2, 20-23], the most potent of which had a $Ca^{2+}$ response $EC_{50}$ value of 630 nM [21]. Potent FPR2 agonists have also been reported with $Ca^{2+}$ response $EC_{50}$ values in the 30-40 nM range [24, 25].

The search for novel ligands with high affinities to newly identified/poorly understood receptors remains one of the fundamental aims of biomedical research. Further understanding of a receptor's structure and function and biological relevance in certain diseases and disorders can be accelerated with the identification of high affinity ligands. Synthetic combinatorial methods have been in use for the last 20 years and have fundamentally advanced the ability to synthesize and screen large numbers of compounds. One of the earliest methods described, mixture-based libraries combined with positional scanning deconvolution is the approach that enables the most rapid and economical efficient acquisition of chemical and biological information [26-29]. The ability to identify specific functionalities responsible for driving the activity at each variable position of a chemical scaffold or pharmacophore is one of its strengths, and to this extent mixture-based libraries represent powerful tools that can be used for the identification of active individual compounds for a wide range of important biological targets.

Another advantage of mixture-based libraries resides in the very high densities of compounds that can be synthesized in highly dense regions of chemical space [30, 31] to quickly identify 'activity cliffs' defined as chemical compounds with high similar structure but unexpectedly very different biological activity [31, 32]. The diversity of the libraries synthesized by Torrey Pines Institute for Molecular Studies (TPIMS) has been characterized and described quantitatively by means of molecular scaffolds, molecular properties, and structural fingerprints. It has been shown that TPIMS libraries are unique in that there is partial overlap with the structural space of drugs, some libraries display scaffolds not present in other compound collections [31], and have increased molecular complexity as compared to compound libraries commonly used in high throughput screening (HTS) programs [30].

Extensive computational studies demonstrate that TPIMS libraries are excellent sources to identify selective compounds and expand the traditional relevant medicinal chemistry space typically covered by current commercial screening collections as well as the Molecular Library Small Molecular Repository (MLSMR) [30]. When compared to existing HTS programs, in which tens of thousands of individual compounds are screened against therapeutically important targets, millions of compounds formatted as mixtures can be examined using substantially less material and at much lower time/labor economics than if these same mixture-based diversities were made and screened as individual compounds. This unique combinatorial library approach can be applied to virtually any existing bioassay for the identification of novel ligands as has been reviewed [26, 27, 33].

SUMMARY OF THE INVENTION

In one embodiment, the invention provides a method for high-throughput screening of combinatorial libraries to identify FPR1 agonists and/or FPR2 antagonists by positional scanning deconvolution. More specifically, screening methods and assays of the invention conduct positional scanning deconvolution of a plurality of mixture-based combinatorial libraries using a single cross-reactive peptide ligand and a duplex flow cytometric screen that identifies levels of FPR1 and/or FPR2 expression in color-coded cell lines. Assays used in these high-throughput screening methods can comprise at least thirty mixture-based combinatorial libraries containing approximately five million or more small molecules. Competitive displacement of a fluorescent ligand can be used as the primary screening methodology. Optionally, screening methods and assays of the invention are performed in silico using computer-based computational approaches.

In a preferred high-throughput screening method of the invention, a duplex flow cytometry assay is used to measure inhibition of FITC-labeled Wpep peptide binding to FPR1 and FPR2 receptors. The step of positional scanning deconvolution can involve testing the most active mixtures for each of the receptors in a dose response manner and using the resultant information to select the functionalities of each position of a small molecule FPR1 ligand (agonist or antagonist) and/or a FPR2 ligand (agonist or antagonist). Selective high-affinity (low nM $K_i$) individual compounds can be identified from two or more separate libraries. For example, assays and high-throughput screening methods of the invention are selective for high affinity (low nM $K_i$) individual compounds have an $EC_{50}$ of about 130 nM (4 nM $K_i$) and an $IC_{50}$ of about 80 nM (1 nM $K_i$) in intracellular $Ca^{2+}$ response determinations.

Preferably, high throughput screening is conducted on combinatorial libraries comprising a total of about 2,000 to about 10,000 wells. High throughput screening can also be conducted on between about 30 to about 40 different mixture-based combinatorial libraries totaling more than 5 million small molecules contained in about 2,000 to about 10,000 mixing samples, often about 5,000 to about 7,000 mixture samples.

In certain embodiments of screening methods and assays of the invention, the step of positional scanning deconvolution uses dual-activity difference (DAD) maps to (a) represent a visual and quantitative analysis of all pair-wise comparisons of one or more substitutions around a putative FPR1 ligand (agonist or antagonist) and/or a FPR2 ligand (agonist or antagonist) molecular template, and (b) to identify putative FPR1 agonist or antagonist and/or a FPR2 agonist or antagonist single- and double-target R-cliffs.

In another embodiment, the invention provides novel FPR1 and FPR2 agonists and antagonists and pharmaceutical compositions and methods of treatment that use such compounds to treat a wide-range of FPR1 and/or FPR2-related disorders, including amyloidosis, Alzheimer's disease, a prion disease, HIV, a cancer or an inflammatory disorder.

For example, the invention provides novel FPR2 ligands (agonists or agonists, preferably, antagonists) of the formula (I):

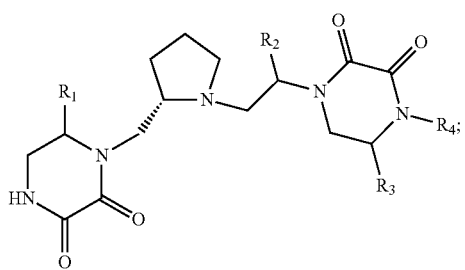

wherein:
$R_1$ and $R_4$ are the same or different and are independently selected from the group consisting of substituted or unsubstituted $C_{1-6}$ alkyl or $C_2$-$C_6$ alkenyl or alkynyl;
$R_2$ is $R_a$-$R_b$, where $R_a$ is substituted or unsubstituted aryl or heteroaryl and $R_b$ is selected from the group consisting of substituted or unsubstituted $C_{1-6}$ alkyl or $C_2$-$C_6$ alkenyl or alkynyl;
$R_3$ is a substituted or unsubstituted aryl; and
$R_4$ is a substituted or unsubstituted $C_{1-6}$ alkyl or $C_2$-$C_6$ alkenyl or alkynyl.

A particularly preferred FPR2 antagonist of the invention has the formula:

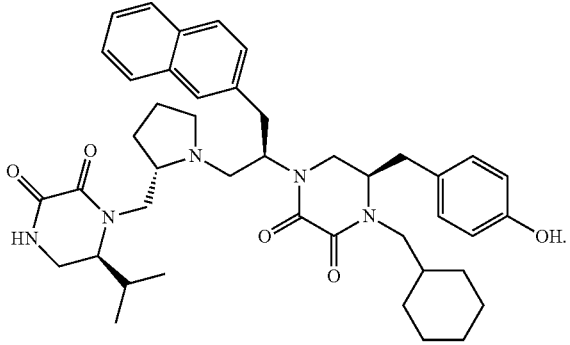 [SMILES: CC(C)[C@H]1CNC(=O)C(=O)N1C[C@@H]1CCCN1C[C@@H](Cc1ccc2ccccc2c1)N1C[C@@H](Cc2ccc(O)cc2)N(CC2CCCCC2)C(=O)C1=O]

The invention also provides novel FPR1 ligands (preferably, agonists) of the formula (II):

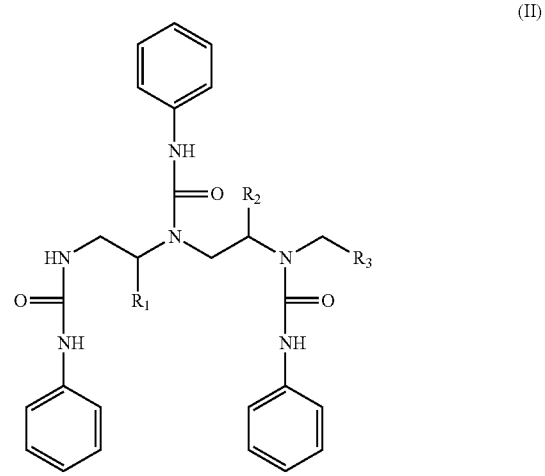

wherein:
$R_1$ and $R_2$ are the same or different and are independently selected from the group consisting of substituted or unsubstituted $C_{1-6}$ alkyl or $C_2$-$C_6$ alkenyl or alkynyl; and
$R_3$ is a substituted or unsubstituted aryl.

A particularly preferred FPR1 agonist of the invention has the formula:

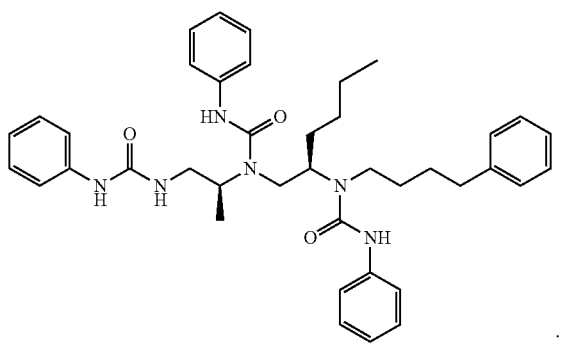 [SMILES: CCCC[C@H](CN(C(=O)Nc1ccccc1)[C@@H](C)CNC(=O)Nc1ccccc1)N(CCCCc1ccccc1)C(=O)Nc1ccccc1]

Another preferred compound of the invention is unique in that it is a FPR1 antagonist and a FPR2 agonist; this compound has the formula:

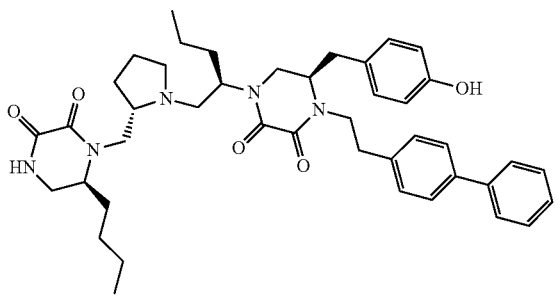

Since down-regulation of FPR2 has been implicated in inflammatory-related processes in murine colonic epithelia cells, see Chen, et al., Formylpeptide receptor-2 contributes to colonic epithelial homeostasis, inflammation and tumorigenesis, *J. Clin. Invest.,* 2013; 12 3(4):1694-1704, this compound's FPR1 antagonist/FPR2 agonist properties may make it particularly well-suited to treating gastrointestinally-related inflammatory disorders and gastrointestinally-related cancers.

The invention also includes pharmaceutically acceptable salts, enantiomers, stereoisomers, solvates and polymorphs of the novel FPR1 and FPR2 agonists and antagonists described herein.

The novel FPR1 and FPR2 agonists and antagonists of the invention can also be used as controls in the screening methods and assays described herein.

Thus, the invention provides versatile chemical scaffolds that (1) exhibit selective, high affinity interactions with human FPR1 and FPR2 in ligand competition assays, and (2) have identified a novel FPR1 small molecule agonist and a FPR2 small molecule antagonist of unprecedented potency.

These and other aspects of the invention are described further in the Detailed Description of the Invention.

BRIEF DESCRIPTION OF THE FIGURES

FIG. 1EX1 (Example 1) shows a scatter plot representation of 106 individual compounds from the 1344 library (pyrrolidine bis-diketopiperazine scaffold) screened against FPR1 and FPR2. The binding activities (Ki nM) of each compound in both receptors are shown, their selectivity is denoted and the number of compounds with different activities and selectivities are shown.

FIG. 1EX2 (Example 1) shows that the agonist and antagonist concentration dependent activity of selected compounds. Test compounds with agonist activity (left column) were added to mixtures of FPR1 and FPR2 cells at the indicated final concentrations to determine changes in Fluo4 fluorescence intensity in FPR1 cells (squares) and FPR2 cells (circles), indicative of mobilization of intracellular calcium. Responses were normalized to results observed with control peptides, 4pep (fMLFF) for FPR1 and Wpep (WKYMVm) for FPR2. Test compounds with antagonist activity (right column) were pre incubated 5 min with mixtures of differentially labeled FPR1 and FPR2 cells after which control peptides were added and Fluo4 fluorescence intensity changes in FPR1 cells (top two figures) or FPR2 cells (bottom two figures) were recorded. Responses were normalized with respect to results observed when cells were treated with 4Pep alone (FPR1 cells) or WPep alone (FPR2 cells), each used at its predetermined EC90 concentration. Curves were fit by GraphPad Prism 5.0 software to a 4 parameter logistic sigmoidal dose-response model in which one parameter (Bottom) was constrained to a value of 0%. The other parameters (Top, $EC_{50}$ and Hill Slope) were determined by the fitted curve. In agonist determinations (left column) the fitted response plateau (Top) corresponded to response efficacy, the maximum response achieved relative to appropriate control peptide. Response efficacies of 1754-49, 1754-56 and 1753-103 were 67, 98 and 78%, respectively.

FIG. 1EX3, Table 1 (Example 1) shows the structure and activity information for individual compounds derived from library 1344 (n=107) and 1481 (n=4) and as otherwise described herein.

FIG. 1EX4, Table 2 (Example 1) shows examples of active compounds for FPR1 and FPR2.

FIG. 2EX1 (Example 2). Activity profiles for FPR1 and FPR2 screened against 37 different mixture-based small molecule libraries. Each library screened is numbered (see Supplemental Table 1 for library details) and color coded, and each bar represents the activity (% inhibition of labeled ligand binding to receptor) for a given mixture within each library.

FIG. 2EX2 (Example 2). Scatter plot representation of 106 individual compounds derived from pyrrolidine bis-diketopiperazine library screened against FPR1 and FPR2. The activities ($K_i$ μM) of each compound for each receptor are shown, their selectivity is denoted and the number of compounds with different activities and selectivities are shown. See Supplemental Dataset 1 for structure and activity data on each compound. Data labeled a-g refer to compounds in Table 2 (FIG. 2EX4). This FIG. 2EX2 is the same as FIG. 1EX1, Example 1, but has been maintained here for consistency of the narrative in Example 2.

FIG. 2EX3 (Example 2). Visual representation of the structure-activity relationship (SAR) of 106 individual compounds screened against FPR1 and FPR2. The distribution of the activity ($K_i$) values for compounds containing an R-group is color-coded using a continuous scale from more active (red) to less active (green). The most populated R-groups, with three or more compounds, are shown. The number of compounds with a given substituent is represented with the number of slices in each pie. For visual clarity, the maximum number of slices shown is 16. The figure was generated with the Structure-Activity Report application of Molecular Operating Environment (version 2011.10; Chemical Computing Group Inc.: Montreal, Quebec, Canada)(Clark and Labute, 2009).

FIGS. 2EX4 and 2EX5 (Example 2): contains (1) Table 1 (FIG. 2EX4) which represents a library of compounds of the pyrrolidine bis-diketopiperazine (see the compound figure in Table 2) with individual substituents $R_1$, $R_2$, $R_3$ and $R_4$.or for the polyphenylurea scaffold. Comparison of FPR1and FPR2 ligands identified by 4 different screening programs, as determined in the experiment(s) of Example 2; and (2) Table 2 (FIG. 2EX5). Examples of active compounds for FPR1 and FPR2, as determined in the experiment(s) of Example 2.

FIG. 2EX6 (Example 2): activity profiles for FPR1 and FPR2 screened against pyrrolidine bis-diketopiperazine positional scanning library (library 21 in 2EX1; library 1344 in Table S1, FIG. 2EX9).

FIG. 2EX7 (Example 2): agonist and antagonist concentration-dependent activity of selected compounds, as determined in the experiment(s) of Example 2. This figure is the same as FIG. 2, Example 1, but has been maintained for consistency of the narrative in Example 2.

FIG. 2EX8 (Example 2): (1) structural differences result in shift of receptor functionality or specificity, as determined in the experiment(s) of Example 2 (2) FPR1 and FPR2 test data, as determined in the experiment(s) of Example 2; and (3) FPR1 and FPR2 SAR data, as determined in the experiment(s) of Example 2.

FIGS. 2EX9 (Table S1), 2EX10 (Table S2) and 2EX11 (Table S3) (Example 2): supplementary tables S1-S3 (2EX9, 2EX10 and 2EX11) provide data as determined in the experiment(s) of Example 2.

FIG. 3EX1 (Example 3). Core scaffold of the 106 pyrrolidine bis-diketopiperazines analyzed in the experiment(s) of Example 3.

FIG. 3EX2 (Example 3). General form of a Dual-Activity Difference (DAD) map for targets I and II. The dashed lines intersect the axes at potency difference values of 0±t e.g., t=1 (one log unit). The regions are as follows: Z1, substitution(s) result in a significant decrease or increase of activity in both targets; Z2, substitution(s) increase activity for one target, while decreasing activity for the other target significantly; Z3 and Z4, substitution(s) result in significant changes in activity on one target, but not an appreciable change on the other.

FIG. 3EX3 (Example 3). Dual-activity difference maps for the 106 compounds. Each data point represents a pairwise comparison with (A) one substitution (275 data points total) and (B) two substitutions (896 data points). Data points in the center of each DAD map (zone Z5) with potency difference ≤1 log unit for any target are in gray. The table shows the number and percentage of data points in each region of the map for compound pairs with single and double substitutions, respectively.

FIG. 3EX4 (Example 3). Activity switches for single substitutions. Data points are colored by the mean structure similarity (see FIG. S2 in the Supporting Information). The switches are readily identified in zone Z2 of the DAD maps. The structural change in each pair is highlighted in magenta. The table summarizes the potency difference and fingerprint-based similarity values for each pair.

FIG. 3EX5 (Example 3). Representative activity switches with double substitutions (selected from 49 pairs in total). The switches are readily identified in the zone Z2 of DAD maps. The structural changes in each pair are highlighted in magenta. The table summarizes the potency difference and fingerprint-based similarity values for each pair.

FIG. 3EX6 (Example 3). Dual target activity cliffs for single substitutions with the same direction e.g., increases or decreases the activity for the two targets. The seven activity cliffs with direct SAR are readily identified in zone Z1 of the DAD maps. The structural changes in each pair are highlighted in magenta. The table summarizes the potency difference and fingerprint-based similarity values for each pair.

FIG. 3EX7 (Example 3). Activity cliffs for FPR1 and FPR2 (deep cliffs with >3 log units in potency difference for single substitutions). The structural changes in each pair are highlighted in magenta. The table summarizes the potency difference and fingerprint-based similarity values for each pair.

FIGS. 3EX8 (Example 3) and 3EX9 (Example 3) contains: (1) Table 1 (same as 2EX4). Number of pair-wise comparisons for 1-4 substitutions and summary of the distribution of the molecular similarity using Tanimoto and three different fingerprints, as determined in the experiment (s) of Example 3 (2) Table 2 (same as 2EX5). Distribution of the absolute potency difference for the two targets, corresponding to all 5,565 pair-wise comparisons and all corresponding pair-wise comparisons for 1-4 substitutions, as determined in the experiment(s) of Example 3 (3) Table S1 (FIG. 2EX9). SMILES representation and biological activity of the 106 compounds analyzed in the experiment(s) of Example 3. Dual-activity difference maps for the 106 compounds. Each data point represents a pairwise comparison with (A) three substitutions (1863 data points) and (B) four substitutions (2531 data points). Data points in the center of each DAD map (zone Z5) with potency difference ≤1 log unit for any target are in gray (5) FIG. S2 (same as FIG. 2EX6). Dual-activity difference maps for the 106 compounds. Data points are color-coded by the mean structure similarity using a continuous scale from green (less similar) to red (more similar). Each data point represents a pairwise comparison with (A) one substitution (275 data points total); (B) two substitutions (896 data points); (C) three substitutions (1863 data points), and (D) four substitutions (2531 data points). The remaining pairs in each map are displayed in light gray for reference. (6) FIG. S3 (same as FIG. 1EX2). Consensus SAS map for FPR1. Each data point represents a pairwise comparison of 106 compounds (5565 data points). Each panel shows in color pairwise comparisons with (A) one substitution (275 data points total); (B) two substitutions (896 data points); (C) three substitutions (1863 data points), and (D) four substitutions (2531 data points). The remaining pairs in each map are displayed in light gray (7) FIG. S4. Consensus SAS map for FPR2. Each data point represents a pairwise comparison of 106 compounds (5565 data points). Each panel shows in color pairwise comparisons with (A) one substitution (275 data points total); (B) two substitutions (896 data points); (C) three substitutions (1863 data points), and (D) four substitutions (2531 data points). The remaining pairs in each map are displayed in light gray.

FIG. 4EX1 (Example 4) shows a simplified illustration of the screening process using mixture-based combinatorial libraries. In a scaffold ranking library, all compounds in the library are simultaneously present as a mixture in a single sample.

FIG. 4EX2 (Example 4). 32 small-molecule libraries tested against FPR1 and FPR2, as determined in the experiment of Example 4.

FIG. 4EX3 (Example 4). Comparison of the extrapolated scaffold ranking IC5o of each library (SR, shown as red stars), and the harmonic means of the extrapolated IC5os of each position of the positional scanning libraries samples (P1, P2, P3 and P4, shown as blue circles), as determined in the experiment of Example 4.

FIG. 4EX4 (Example 4): Table 1. Scaffold Ranking xIC5os, compared to the Harmonic Means of Positional Scanning xIC5os. Library 19 (red/dark) is the most active in both, as determined in the experiment of Example 4.

FIG. 4EX5 (Example 4): Table 2. Indices of Differentiation and Deconvolutability for the 32 libraries against both targets. The most differentiated positions and the most deconvolutable libraries are shown in red), as determined in the experiment of Example 4.

FIG. 4EX6 (Example 4). Examples of very high differentiation (Library 32, Position 2, for FPR1) and little differentiation (Library 19, Position 2, for FPR1) in positional scanning profiles, as defined in Equation (5) and as determined in the experiment of Example 4. Note that overall, Library 19 exhibits more activity, but Library 32 is clearly more well-differentiated. Additional zero percent inhibition values have been removed from Library 32's profile for clarity.

FIG. 4EX7 (Example 4). Indices of deconvolutability for each library, as defined in Equation (6), against both targets) and as determined in the experiment of Example 4.

FIG. 4EX8 (Example 4). The full positional scanning profile of Library 19, as determined in the experiment of Example 4. Notice that there are many instances of different mixtures among the most active at the FPR1 target not being active at the FPR2 target, and vice versa. This indicates the potential selectivity that was eventually found.

DETAILED DESCRIPTION OF THE INVENTION

In accordance with the present invention there may be employed conventional chemical synthetic methods and other biological and pharmaceutical techniques within the skill of the art. Such techniques are well-known and are otherwise explained fully in the literature.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It is to be noted that as used herein and in the appended claims, the singular forms "a," "and" and "the" include plural references unless the context clearly dictates otherwise.

Furthermore, the following terms shall have the definitions set out below. It is understood that in the event a specific term is not defined herein, that term shall have a meaning within its typical use within context by those of ordinary skill in the art.

The term "compound", as used herein, unless otherwise indicated, refers to any specific chemical compound disclosed herein. Within its use in context, the term generally refers to a single compound as otherwise described herein. In certain instances the term may also refer to stereoisomers and/or optical isomers (including racemic mixtures) or enantiomerically enriched mixtures of disclosed compounds. Compounds which are disclosed are those which are stable and where a choice of substituents and claim elements is available, the substituent or claim element is chosen such that stable compounds are formed from the disclosed elements and substituents. The symbol ===== in a chemical structure or formula signifies that either a double or single bond may be present between the atoms to which such symbol is attached, depending upon the valence of those atoms and substituents which are on such atoms.

The term "patient" or "subject" is used throughout the specification within context to describe an animal, especially including a domesticated mammal and preferably a human, to whom a treatment or procedure, including a prophylactic treatment or procedure is performed. For treatment of those infections, conditions or disease states which are specific for a specific animal such as a human patient, the term patient refers to that specific animal. In most instances, the patient or subject of the present invention is a domesticated/agricultural animal or human patient of either or both genders.

The term "effective" is used herein, unless otherwise indicated, to describe an amount of a compound or composition which, in context, is used to produce or effect an intended result (e.g. the treatment of amyloidosis, Alzheimer's disease, a prion-related disorder, HIV, a cancer or an inflammatory disorder). The term effective subsumes all other effective amount or effective concentration terms which are otherwise described or used in the present application.

The term "human immunodeficiency virus" shall be used to describe human immunodeficiency virus (HIV) and its infections, which term shall be used to embrace both human immunodeficieny virus 1 (HIV-1) and human immunodeficiency virus 2 (HIV-2). The term "human immunodeficiency virus" shall be used to describe human immunodeficiency virus I (HIV 1 and 2), the growth or replication of which may be inhibited or disease states of which may be treated using one or more methods according to the present invention. Viruses which may be treated according to the present invention include, for example, human immunodeficiency viruses 1 and 2 (HIV-1 and HIV-2), among others. The term HIV includes mutant strains of HIV including "drug resistant" or "multiple drug resistant" strains of the HIV virus which have mutated to be resistant to one or more clinically approved anti-HIV agents. Exemplary HIV drug resistant strains which may be effectively treated using compounds according to the present invention include the following, among others: (defined by RT mutation)—XXBRU, K65R, Y115F, F116Y, Q151M, M184V, L74V, V75T, 4XZT, T215Y, K103N, T215Y/M184V, 5705-72, 488-101, C910-6, LA1M184V, G910-6 L100I, K101E, K103N, V106A, D110E, V179D, Y181C, D185E, D186E, Y188H, G190E, E138K, M41L, D67N, K70R, T215Y/F, K219Q/E, Y181C, K103N, L100I, Y188C/H among others, especially Y181C and/or K103N/Y181C, among others.

The terms "ARC" and "AIDS" refer to syndromes of the immune system caused by the human immunodeficiency virus, which are characterized by susceptibility to certain diseases and T cell counts which are depressed compared to normal counts. HIV progresses from Category 1 (Asymptomatic HIV Disease) to Category 2 (ARC), to Category 3 (AIDS), with the severity of the disease.

An "inflammatory disorder" includes, but is not limited to, lung diseases, hyperglycemic disorders including diabetes and disorders resulting from insulin resistance, such as Type I and Type II diabetes, as well as severe insulin resistance, hyperinsulinemia, and dyslipidemia (e.g. hyperlipidemia (e.g., as expressed by obese subjects), elevated low-density lipoprotein (LDL), depressed high-density lipoprotein (HDL), and elevated triglycerides) and insulin-resistant diabetes, such as Mendenhall's Syndrome, Werner Syndrome, leprechaunism, and lipoatrophic diabetes, renal disorders, such as acute and chronic renal insufficiency, end-stage chronic renal failure, glomerulonephritis, interstitial nephritis, pyelonephritis, glomerulosclerosis, e.g., Kimmelstiel-Wilson in diabetic patients and kidney failure after kidney transplantation, obesity, GH-deficiency, GH resistance, Turner's syndrome, Laron's syndrome, short stature, increased fat mass-to-lean ratios, immunodeficiencies including decreased $CD4^+$ T cell counts and decreased immune tolerance or chemotherapy-induced tissue damage, bone marrow transplantation, diseases or insufficiencies of cardiac structure or function such as heart dysfunctions and congestive heart failure, neuronal, neurological, or neuromuscular disorders, e.g., diseases of the central nervous system including Alzheimer's disease, or Parkinson's disease or multiple sclerosis, and diseases of the peripheral nervous system and musculature including peripheral neuropathy, muscular dystrophy, or myotonic dystrophy, and catabolic states, including those associated with wasting caused by any condition, including, e.g., mental health condition (e.g., anorexia nervosa), trauma or wounding or infection such as with a bacterium or human virus such as HIV, wounds, skin disorders, gut structure and function that need restoration, and so forth.

"Inflammatory disorder" also includes a cancer and an "infectious disease" as defined herein, as well as disorders of bone or cartilage growth in children, including short stature, and in children and adults disorders of cartilage and bone in children and adults, including arthritis and osteoporosis. An "inflammation-associated metabolic disorder" includes a combination of two or more of the above disorders (e.g., osteoporosis that is a sequela of a catabolic state). Specific disorders of particular interest targeted for treatment herein are diabetes and obesity, heart dysfunctions, kidney disorders, neurological disorders, bone disorders, whole body growth disorders, and immunological disorders.

In one embodiment, an "inflammatory disorder" includes central obesity, dyslipidemia including particularly hypertriglyceridemia, low HDL cholesterol, small dense LDL particles and postpranial lipemia; glucose intolerance such as impaired fasting glucose; insulin resistance and hypertension, and diabetes. The term "diabetes" is used to describe diabetes mellitus type I or type II. The present invention relates to a method for improving renal function and symptoms, conditions and disease states which occur secondary to impaired renal function in patients or subjects with diabetes as otherwise described herein. It is noted that in diabetes mellitus type I and II, renal function is impaired from collagen deposits, and not from cysts in the other disease states treated by the present invention.

A "neurodegenerative disorder" or "neuroinflammation" includes, but is not limited to, Alzheimer's Dementia (AD), amyotrophic lateral sclerosis, depression, epilepsy, Huntington's Disease, multiple sclerosis, the neurological complications of AIDS, spinal cord injury, glaucoma and Parkinson's disease.

The term "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Cancers generally show partial or complete lack of structural organization and functional coordination with the normal tissue and most invade surrounding tissues, metastasize to several sites, and are likely to recur after attempted removal and to cause the death of the patient unless adequately treated. As used herein, the term cancer is used to describe all cancerous disease states applicable to treatment according to the present invention and embraces or encompasses the pathological process associated with all virtually all epithelial cancers, including carcinomas, malignant hematogenous, ascitic and solid tumors. Examples of cancers which may be treated using methods according to the present invention include, without limitation, carcinomas (e.g., squamous-cell carcinomas, adenocarcinomas, hepatocellular carcinomas, and renal cell carcinomas), particularly those of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, and melanoma); mixed types of neoplasias, particularly carcinosarcoma and Hodgkin's disease; and tumors of mixed origin, such as Wilms' tumor and teratocarcinomas. See, for example, The Merck Manual of Diagnosis and Therapy, 17.sup.th ed. (Whitehouse Station, N.J.: Merck Research Laboratories, 1999) 973-74, 976, 986, 988, 991).

In addition to the treatment of ectopic cancers as described above, the present invention also may be used preferably to treat eutopic cancers such as choriocarcinoma, testicular choriocarcinoma, non-seminomatous germ cell testicular cancer, placental cancer (trophoblastic tumor) and embryonal cancer, among others.

An "immune disorder" includes, but is not limited to, lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease and leukemia.

Neuroinflammation is actively involved in many neurological diseases, including Alzheimer's Dementia (AD), amyotrophic lateral sclerosis, depression, epilepsy, Huntington's Disease, multiple sclerosis, the neurological complications of AIDS, spinal cord injury, glaucoma and Parkinson's disease. Research into neuroinflammation may benefit all of these disorders. This research focuses on developing BBB-permeable MRI contrast agents for monitoring neuroinflammation in Alzheimer's disease. Particularly in AD, there is a correlation between local inflammation, and presence of amyloid plaques and neurofibrillary tangles. Age-dependent reactive gliosis has long been recognized in human AD and in mouse models of cerebral amyloidosis. Microglia and astrocytes with altered morphology appear early in rodent models, prior to development of frank amyloid plaques. Nuclear Factor κB (NFκB) is the master regulator of inflammation.

In the case of Alzheimer's disease, useful additional agents that may be administered in accordance with the invention include, but are not limited to, cholinesterase inhibitors, antioxidant Ginkobiloba extract, nonsteroidal anti-inflammatory agents, and non-specific NMDA antagonists, such as Ebixa® (Memantine). Also, compositions and methods of treatment of the invention can be combined with other conventional AD therapies, such as drugs used to treat cognitive and behavioral symptoms of Alzheimer's patients (e.g. Reminyl®, Exelon®, Aricept®, Cognex®, and Namenda®).

"Amyloidosis" and "Amyloid-related disorders" include diseases associated with the accumulation of amyloid which can either be restricted to one organ, "localized amyloidosis", or spread to several organs, "systemic amyloidosis". Secondary amyloidosis may be associated with chronic infection (such as tuberculosis) or chronic inflammation (such as rheumatoid arthritis), including a familial form of secondary amyloidosis which is also seen in Familial Mediterranean Fever (FMF) and another type of systemic amyloidosis found in long-term hemodialysis patients. Localized forms of amyloidosis include, without limitation, type II diabetes and any related disorders thereof, neurodegenerative diseases such as scrapie, bovine spongiform encephalitis, Creutzfeldt-Jakob disease, Alzheimer's disease, senile systemic amyloidosis (SSA), Cerebral Amyloid Angiopathy, Parkinson's disease, and prion protein related disorders (e.g. prion-related encephalopathies), and rheumatoid arthritis.

A "biomarker" is any gene or protein whose level of expression in a biological sample is altered compared to that of a pre-determined level. The pre-determined level can be a level found in a biological sample from a normal or healthy subject. Biomarkers include genes and proteins, and variants and fragments thereof. Such biomarkers include DNA comprising the entire or partial sequence of the nucleic acid sequence encoding the biomarker, or the complement of such a sequence. The biomarker nucleic acids also include RNA comprising the entire or partial sequence of any of the nucleic acid sequences of interest. A biomarker protein is a protein encoded by or corresponding to a DNA biomarker of the invention. A biomarker protein comprises the entire or partial amino acid sequence of any of the biomarker proteins or polypeptides. Biomarkers can be detected, e.g. by nucleic acid hybridization, antibody binding, activity assays, polymerase chain reaction (PCR), S1 nuclease assay and gene chip.

A "control" as used herein may be a positive or negative control as known in the art and can refer to a FPR1 or FPR2 agonist or antagonist composition (e.g. small molecule), or a control cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. For instance, as can be appreciated by a skilled artisan, a control may comprise data from one or more control subjects that is stored in a reference database. The control may be a subject who is similar to the test subject (for instance, may be of the same gender, same race, same general age and/or same general health) but who is known to not have a fibrotic disease. As can be appreciated by a skilled artisan, the methods of the invention can also be modified to compare a test subject to a control subject who is similar to the test subject (for instance, may be of the same gender, same race, same general age and/or same general health) but who is known to express symptoms of a disease. In this embodiment, a diagnosis of a disease or staging of a disease can be made by determining whether protein or gene expression levels as described herein are statistically similar between the test and control subjects.

The terms "level" and/or "activity" as used herein further refer to gene and protein expression levels or gene or protein activity. For example, gene expression can be defined as the utilization of the information contained in a gene by transcription and translation leading to the production of a gene product.

In certain non-limiting embodiments, an increase or a decrease in a subject or test sample of the level of measured biomarkers (e.g. proteins or gene expression) as compared to a comparable level of measured proteins or gene expression in a control subject or sample can be an increase or decrease in the magnitude of approximately ±5,000-10,000%, or approximately ±2,500-5,000%, or approximately ±1,000-2,500%, or approximately ±500-1,000%, or approximately ±250-500%, or approximately ±100-250%, or approximately ±50-100%, or approximately ±25-50%, or approximately ±10-25%, or approximately ±10-20%, or approximately ±10-15%, or approximately ±5-10%, or approximately ±1-5%, or approximately ±0.5-1%, or approximately ±0.1-0.5%, or approximately ±0.01-0.1%, or approximately ±0.001-0.01%, or approximately ±0.0001-0.001%.

The values obtained from controls are reference values representing a known health status and the values obtained from test samples or subjects are reference values representing a known disease status. The term "control", as used herein, can mean a sample of preferably the same source (e.g. blood, serum, tissue etc.) which is obtained from at least one healthy subject to be compared to the sample to be analyzed. In order to receive comparable results the control as well as the sample should be obtained, handled and treated in the same way. In certain examples, the number of healthy individuals used to obtain a control value may be at least one, preferably at least two, more preferably at least five, most preferably at least ten, in particular at least twenty. However, the values may also be obtained from at least one hundred, one thousand or ten thousand individuals.

A level and/or an activity and/or expression of a translation product of a gene and/or of a fragment, or derivative, or variant of said translation product, and/or the level or activity of said translation product, and/or of a fragment, or derivative, or variant thereof, can be detected using an immunoassay, an activity assay, and/or a binding assay. These assays can measure the amount of binding between said protein molecule and an anti-protein antibody by the use of enzymatic, chromodynamic, radioactive, magnetic, or luminescent labels which are attached to either the anti-protein antibody or a secondary antibody which binds the anti-protein antibody. In addition, other high affinity ligands may be used. Immunoassays which can be used include e.g. ELISAs, Western blots and other techniques known to those of ordinary skill in the art (see Harlow and Lane, Antibodies: A Laboratory Manual, Cold Spring Harbor Laboratory Press, Cold Spring Harbor, N.Y., 1999 and Edwards R, Immunodiagnostics: A Practical Approach, Oxford University Press, Oxford; England, 1999). All these detection techniques may also be employed in the format of microarrays, protein-arrays, antibody microarrays, tissue microarrays, electronic biochip or protein-chip based technologies (see Schena M., Microarray Biochip Technology, Eaton Publishing, Natick, Mass., 2000).

Certain diagnostic and screening methods of the present invention utilize an antibody, preferably, a monocolonal antibody, capable of specifically binding to a protein as described herein or active fragments thereof. The method of utilizing an antibody to measure the levels of protein allows for non-invasive diagnosis of the pathological states of kidney diseases. In a preferred embodiment of the present invention, the antibody is human or is humanized. The preferred antibodies may be used, for example, in standard radioimmunoassays or enzyme-linked immunosorbent assays or other assays which utilize antibodies for measurement of levels of protein in sample. In a particular embodiment, the antibodies of the present invention are used to detect and to measure the levels of protein present in a renal cell or urine sample.

Humanized antibodies are antibodies, or antibody fragments, that have the same binding specificity as a parent antibody, (i.e., typically of mouse origin) and increased human characteristics. Humanized antibodies may be obtained, for example, by chain shuffling or by using phage display technology. For example, a polypeptide comprising a heavy or light chain variable domain of a non-human antibody specific for a disease related protein is combined with a repertoire of human complementary (light or heavy) chain variable domains. Hybrid pairings specific for the antigen of interest are selected. Human chains from the selected pairings may then be combined with a repertoire of human complementary variable domains (heavy or light) and humanized antibody polypeptide dimers can be selected for binding specificity for an antigen. Techniques described for generation of humanized antibodies that can be used in the method of the present invention are disclosed in, for example, U.S. Pat. Nos. 5,565,332; 5,585,089; 5,694,761; and 5,693,762. Furthermore, techniques described for the production of human antibodies in transgenic mice are described in, for example, U.S. Pat. Nos. 5,545,806 and 5,569,825.

"Hydrocarbon" or "hydrocarbyl" refers to any monovalent (or divalent in the case of alkylene groups) radical containing carbon and hydrogen, which may be straight, branch-chained or cyclic in nature. Hydrocarbons include linear, branched and cyclic hydrocarbons, including alkyl groups, alkylene groups, saturated and unsaturated hydrocarbon groups including aromatic groups both substituted and unsubstituted, alkene groups (containing double bonds between two carbon atoms) and alkyne groups (containing triple bonds between two carbon atoms). In certain instances, the terms substituted alkyl and alkylene are sometimes used synonymously.

"Alkyl" refers to a fully saturated monovalent radical containing carbon and hydrogen, and which may be cyclic, branched or a straight chain. Examples of alkyl groups are methyl, ethyl, n-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopen-tylethyl, cyclohexylethyl, cyclohexyl, cycloheptyl. Preferred alkyl groups are $C_1$-$C_6$ alkyl groups. "Alkylene" refers to a fully saturated hydrocarbon which is divalent (may be linear, branched or cyclic) and which is optionally substituted. Preferred alkylene groups are $C_1$-$C_6$ alkylene groups. Other terms used to indicate substitutuent groups in compounds according to the present invention are as conventionally used in the art. The term "alkenyl" or "alkynyl", as used herein, refers to an aliphatic group containing at least one double bond or triple bond and is intended to include both "unsubstituted alkenyls", "substituted alkenyls", "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds.

The term "aryl" or "aromatic", in context, refers to a substituted or unsubstituted monovalent aromatic radical having a single ring (e.g., benzene or phenyl) more than one ring (e.g. naphthyl). Other examples of aryl groups, in context, may include heterocyclic aromatic ring systems "heteroaryl" groups having one or more nitrogen, oxygen, or sulfur atoms in the ring (5- or 6-membered heterocyclic rings) such as imidazole, furyl, pyrrole, pyridyl, furanyl, thiene, thiazole, pyridine, pyrimidine, pyrazine, triazole, oxazole, among others, which may be substituted or unsubstituted as otherwise described herein.

The term "heterocyclic group" "heterocycle" as used throughout the present specification refers to an aromatic ("heteroaryl") or non-aromatic cyclic group forming the cyclic ring and including at least one and up to three hetero atoms such as nitrogen, sulfur or oxygen among the atoms forming the cyclic ring. The heterocyclic ring may be saturated (heterocyclic) or unsaturated (heteroaryl). Exemplary heterocyclic groups include, for example pyrrolidinyl, piperidinyl, morpholinyl, pyrrole, pyridine, pyridone, pyrimidine, imidazole, thiophene, furan, pyran, thiazole, more preferably pyrimidinyl, pyrrolidinyl, piperidinyl, morpholinyl, oxazole, isoxazole, pyrrole, pyridine, thiophene, thiazole and even more preferably pyrimidinyl, especially uracil or cytosine which are optionally substituted, furyl, 3-methylfuryl, thiazole, piperazinyl, N-methylpiperazinyl, tetrahydropyranyl and 1,4-dioxane, among others. Additional heterocyclic groups include oxazole, benzoxazole, pyrrole, dihydropyrrole, benzopyrrole, benzodihydropyrrole, indole, indolizine, among others.

The term "substituted" shall mean substituted at a carbon (or nitrogen) position within context, hydroxyl, carboxyl, cyano (C≡N), nitro ($NO_2$), halogen (preferably, 1, 2 or 3 halogens, especially on an alkyl, especially a methyl group such as a trifluoromethyl), alkyl group (preferably, $C_1$-$C_{10}$, more preferably, $C_1$-$C_6$), alkoxy group (preferably, $C_1$-$C_6$ alkyl or aryl, including phenyl and substituted phenyl), ester (preferably, $C_1$-$C_6$ alkyl or aryl) including alkylene ester (such that attachment is on the alkylene group, rather than at the ester function which is preferably substituted with a $C_1$-$C_6$ alkyl or aryl group), preferably, $C_1$-$C_6$ alkyl or aryl, halogen (preferably, F or Cl), nitro or amine (including a five- or six-membered cyclic alkylene amine, further including a $C_1$-$C_6$ alkyl amine or $C_1$-$C_6$ dialkyl amine which alkyl groups may be substituted with one or two hydroxyl groups), amido, which is preferably substituted with one or two $C_1$-$C_6$ alkyl groups (including a carboxamide which is substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Preferably, the term "substituted" shall mean within its context of use alkyl, alkoxy, halogen, ester, keto, nitro, cyano and amine (especially including mono- or di-$C_1$-$C_6$ alkyl substituted amines which may be optionally substituted with one or two hydroxyl groups). Any substitutable position in a compound according to the present invention may be substituted in the present invention, but no more than 3, more preferably no more than 2 substituents (in some instances only 1 or no substituents) is present on a ring. Preferably, the term "unsubstituted" shall mean substituted with one or more H atoms.

The term "pharmaceutically acceptable" refers to a carrier, additive or excipient which is not unacceptably toxic to the subject to which it is administered. Pharmaceutically acceptable excipients are described at length by E. W. Martin, in "Remington's Pharmaceutical Sciences", among others well-known in the art.

A "pharmaceutically acceptable salt" of the present compound generally refers to pharmaceutically acceptable salts form of a compound which can form a salt, because of the existence of for example, amine groups, carboxylic acid groups or other groups which can be ionized in a sample acid-base reaction. A pharmaceutically acceptable salt of an amine compound, such as those contemplated in the current invention, include, for example, ammonium salts having as counterion an inorganic anion such as chloride, bromide, iodide, sulfate, sulfite, nitrate, nitrite, phosphate, and the like, or an organic anion such as acetate, malonate, pyruvate, propionate, fumarate, cinnamate, tosylate, and the like. Certain compounds according to the present invention which have carboxylic acid groups or other acidic groups which may form pharmaceutically acceptable salts, for example, as carboxylate salts, are also contemplated by the present invention.

Aspects of the present invention include compounds which have been described in detail hereinabove or to pharmaceutical compositions which comprise an effective amount of one or more compounds according to the present invention, optionally in combination with a pharmaceutically acceptable carrier, additive or excipient.

The term "pharmaceutically acceptable derivative" is used throughout the specification to describe any pharmaceutically acceptable prodrug form (such as an ester or ether or other prodrug group) which, upon administration to a patient, provides directly or indirectly the present compound or an active metabolite of the present compound.

The term "inhibitory effective concentration" or "inhibitory effective amount" is used throughout the specification to describe concentrations or amounts of compounds according to the present invention which treat amyloidosis, Alzheimer's disease, a prion-related disorder, HIV, a cancer or an inflammatory disorder.

The term "preventing effective amount" is used throughout the specification to describe concentrations or amounts of compounds according to the present invention which are prophylactically effective in preventing, reducing the effects of, or delaying the onset of amyloidosis, Alzheimer's disease, a prion-related disorder, HIV, a cancer or an inflammatory disorder. The terms inhibitory effective amount or preventive effective amount also generally fall under the rubric "effective amount".

The term "co-administration" is used to describe the administration of two or more active compounds, in this case a compound according to the present invention, in combination with an additional therapeutic agent or other biologically active agent, in effective amounts. Although the term co-administration preferably includes the administration of two or more active compounds to the patient at the same time, it is not necessary that the compounds actually be administered at the exact same time, only that amounts of compound will be administered to a patient or subject such that effective concentrations are found in the blood, serum or plasma, or in the pulmonary tissue at the same time.

For example, compounds according to the present invention may be administered with one or more anti-viral agents, including other anti-HIV agents including nucleoside reverse transcriptase inhibitors (NRTI), other non-nucleoside reverse transcriptase inhibitors (i.e., those which are not representative of the present invention), protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C (Elvucitabine), Festinavir, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development.

Anti-cancer compositions and methods of treatment of the invention may entail co-administration of an additional anti-cancer agent, e.g. at least one agent selected from the group consisting of antimetabolites, Ara C, etoposide, doxorubicin, taxol, hydroxyurea, vincristine, cytoxan (cyclophosphamide) or mitomycin C, among numerous others, including topoisomerase I and topoisomerase II inhibitors, such as adriamycin, topotecan, campothecin and irinotecan, other agent such as gemcitabine and agents based upon campothecin and cisplatin for the treatment of cancer, as otherwise described herein. Additional agents which may be combined in pharmaceutical compositions according to the present invention include, for example, adriamycin, anastrozole, arsenic trioxide, asparaginase, azacytidine, BCG Live, bevacizumab, bexarotene capsules, bexarotene gel, bleomycin, bortezombi, busulfan intravenous, busulfan oral, calusterone, campothecin, capecitabine, carboplatin, carmustine, carmustine with polifeprosan 20 implant, celecoxib, cetuximab, chlorambucil, cisplatin, cladribine, clofarabine, cyclophosphamide, cytarabine, cytoxan, cytarabine liposomal, dacarbazine, dactinomycin, actinomycin D, dalteparin sodium, darbepoetin alfa, dasatinib, daunorubicin liposomal, daunorubicin, daunomycin, decitabine, denileukin, denileukin diftitox, dexrazoxane, dexrazoxane, docetaxel, doxorubicin, doxorubicin liposomal, dromostanolone propionate, eculizumab, Elliott's B Solution, epirubicin, epirubicin hcl, epoetin alfa, erlotinib, estramustine, etoposide phosphate, etoposide VP-16, exemestane, fentanyl citrate, filgrastim, floxuridine (intraarterial), fludarabine, fluorouracil 5-FU, fulvestrant, gefitinib, gemcitabine, gemcitabine hcl, gemicitabine, gemtuzumab ozogamicin, goserelin acetate, goserelin acetate, histrelin acetate, hydroxyurea, ibritumomab tiuxetan, idarubicin, ifosfamide, imatinib mesylate, interferon alfa 2a, interferon alfa-2b, irinotecan, lapatinib ditosylate, lenalidomide, letrozole, leucovorin, leuprolide acetate, levamisole, lomustine CCNU, meclorethamine, nitrogen mustard, megestrol acetate, melphalan L-PAM, mercaptopurine 6-MP, mesna, methotrexate, methoxsalen, mitomycin C, mitotane, mitoxantrone, nandrolone phenpropionate, nelarabine, nofetumomab, oprelvekin, oxaliplatin, paclitaxel, paclitaxel protein-bound particles, palifermin, pamidronate, panitumumab, pegademase, pegaspargase, pegfilgrastim, peginterferon alfa-2b, pemetrexed disodium, pentostatin, pipobroman, plicamycin, mithramycin, porfimer sodium, procarbazine, quinacrine, rasburicase, rituximab, sargramostim, sorafenib, streptozocin, sunitinib, sunitinib maleate, talc, tamoxifen, temozolomide, teniposide VM-26, testolactone, thalidomide, thioguanine 6-TG, thiotepa, topotecan, topotecan hcl, toremifene, tositumomab, tositumomab/I-131 tositumomab, trastuzumab, tretinoin ATRA, uracil mustard, valrubicin, vinblastine, vincristine, vinorelbine, vorinostat, zoledronate, zoledronic acid and mixtures thereof.

Compounds according to the present invention may be readily synthesized pursuant to readily available chemical synthetic methods which are available in the art. The preparation of chemical libraries, as detailed in the examples section, proceeds using well known methods which are disclosed in the art. These approaches may be readily modified to provide individual compounds or groups of compounds pursuant to well-known methods.

The compositions of the present invention may be formulated in a conventional manner using one or more pharmaceutically acceptable carriers. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, transdermally, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally, or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically administered transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound of the instant invention that may be combined with the carrier materials to produce a single dosage form will vary depending upon the host treated, the particular mode of administration. Preferably, the compositions should be formulated so that a dosage of between about 0.01 and 150, preferably about 0.5 to about 25 mg/kg of patient/day of the novel compound can be administered to a patient receiving these compositions.

The amount of compound in a pharmaceutical composition of the instant invention that may be combined with the carrier materials to produce a single dosage form will vary depending upon the host and disease treated, the particular mode of administration. Preferably, the compositions should be formulated to contain between about 0.25 milligram to about 1 gram, more preferably about 1 milligram to about 750 milligrams, and even more preferably about 10 milligrams to about 500-600 milligrams of active ingredient.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Oral dosage forms are particularly preferred, because of ease of administration and prospective favorable patient compliance.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques. The use of these dosage forms may significantly the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to viral antigens) may also be prepared by conventional methods to produce pharmaceutically acceptable carriers. This may be appropriate for the delivery of free compounds hynor pro-drug forms of the compounds according to the present invention.

In addition, compounds according to the present invention may be administered alone or in combination with other agents, including other compounds of the present invention. Certain compounds according to the present invention may be effective for enhancing the biological activity of certain agents according to the present invention by reducing the metabolism, catabolism or inactivation of other compounds and as such, are co-administered for this intended effect.

In other aspects of the present invention, certain compounds according to the present invention may be used as antagonists in binding assays, as analytical agents, as agents to be used to isolate or purify proteins and/or as intermediates in the synthesis of further agents, among other uses.

The invention is illustrated further in the following non-limiting examples.

EXAMPLE 1

High Throuput Screening of Mixture Libraries

Table 1 (FIG. 1EX4, Example 1) displays structure and binding activity (Ki) in the duplex receptor assay of 110 compounds that were purified and tested on the basis of deconvoluted results from primary high throughput screening of mixture libraries. FIG. 1 graphically displays the diverse binding activity patterns of the 106 compounds derived from the 1344 library, a collection built around chemical substitutions made at 4 sites of a pyrrolidine bis-diketopiperazine scaffold. Of particular note were 27 distinct compounds with high binding affinity (Ki<100 nM) and selectivity (>100-fold) for one or the other receptor: 15 for FPR1 and 12 for FPR2 (FIG. 1EX1). An additional compound of note exhibited strongly cross-reactive binding, with Ki<100 nM for both receptors.

Table 1 also shows ligand binding data produced from analysis of 4 compounds derived from the 1481 library, a collection built around chemical substitutions made at 3 sites of a polyphenylurea scaffold. All 4 exhibited highly selective binding interactions with FPR1, with Ki ranging from 1 to 21 nM (Table 1).

Extended functional analysis. The structures of two FPR1 selective compounds from the pyrrolidine bis-diketopiperazine library, namely 1754-113 and 1754-56, are shown in Table 2 (FIG. 1EX5) along with that of compound 1754-26, which is the only compound out of the 107 tested with a Ki value less than 100 nM for both receptors. When tested for the ability to elicit or inhibit FPR1-mediated intracellular $Ca^{2+}$ responses, both 1754-56 and 1754-26 acted as antagonists (Table 2, FIG. 1EX5). By contrast, the two compounds exhibited opposite effects in parallel analyses of $Ca^{2+}$ responses mediated by FPR2. 1754-56 was an agonist for FPR2, with a low micromolar $EC_{50}$ that matched the Ki value observed in the competitive ligand displacement assay (FIG. 1EX5, Table 2, and FIGS. 1EX1 and 1EX2). 1754-26 acted as an FPR2 antagonist (FIG. 1EX5, Table 2, and FIG. 1EX2). The only difference between 1754-56 and 1754-26 is the $R_1$ functionality, which is S-butyl and S-isopropyl, respectively. This subtle change in the structure seems to play a dramatic role in selectivity for these ligands and represents a clear example of an 'activity cliff'. The structures of three FPR2 selective pyrrolidine bis-diketopiperazines (1754-20, 1754-19, and 1754-31) are also shown in Table 2. It can be seen that the only difference between non-selective inhibitor, 1754-26, and FPR2-selective inhibitor, 1754-20, is the $R_2$ functionality, which is R-propyl for the former and R-4-hydroxybenzyl for the latter. Another significant functional disparity resulted when the S-isopropyl R1 functionality of 1754-31 was replaced with an S-propyl functionality in 1754-49. Not only was there a decrease in FPR2 selectivity (>10,000 to ~70 nM Ki) but there occurred a conversion from antagonist to partial agonist in FPR2-mediated $Ca^{2+}$ determinations (Table 2, FIG. 1EX4 and FIGS. 1EX1 and 1EX2). Compound 1753-103, derived from the polyphenylurea library, was a selective partial agonist for FPR1 (Table 2, FIG. 1EX4). Two others from this library that selectively bound FPR1 were also determined to be selective partial agonists for FPR1 (1753-101 and 1753-102, Table 1, FIG. 1EX3 and data not shown).

Summary:

We disclose a series of compounds derived from 2 different chemical scaffolds that exhibit selective, high affinity interactions with human FPR1 and FPR2 in ligand competition assays.

1. The newly identified compounds are structurally different from currently described FPR ligands and are based upon pyrrolidine bis-diketopiperazine and polyphenylurea chemical scaffolds.
2. A number of the compounds exhibit selective binding affinities for FPR1 or FPR2 that are the most potent reported to date for small molecules in a ligand competition assay format (eg., 1754-113 and 1753-103 for FPR1; 1754-31 for FPR2; Table 2 (FIG. 1EX5), FIG. 1EX1).
3. Compound 1753-103 is the most potent small molecule agonist reported to date for FPR1 induced intracellular calcium responses (Table 2, FIG. 1EX5).
4. Compound 1754-31 is the most potent small molecule antagonist reported to date for FPR2 induced intracellular calcium responses (Table 2, FIG. 1EX5).
5. Compound 1754-56 is simultaneously an agonist for FPR2 and an antagonist for FPR1 (Table 2, FIG. 1EX5), a unique combination that, to our knowledge, has not been previously reported for any compound, small molecule or otherwise.

We expect that the functionally diverse array of high affinity ligands derived from the pyrrolidine bis-diketopiperazine library will be a unique resource for dissecting structure activity relationships for a range of distinct, biologically important functional responses mediated by FPR1 and FPR2. Understanding of such relationships can aid in identifying strategies to optimize therapeutic benefits of FPR oriented drugs while minimizing undesirable off-target effects.

References For Background of the Invention and Example 1

1. Ye, R. D., Boulay, F., Wang, J. M., Dahlgren, C., Gerard, C., Parmentier, M., Serhan, C. N., and Murphy, P. M. (2009). International Union of Basic and Clinical Pharmacology. LXXIII. Nomenclature for the formyl peptide receptor (FPR) family. Pharmacol Rev 61, 119-161.
2. Kirpotina, L. N., Khlebnikov, A. I., Schepetkin, I. A., Ye, R. D., Rabiet, M. J., Jutila, M. A., and Quinn, M. T. (2010). Identification of novel small-molecule agonists for human formyl peptide receptors and pharmacophore models of their recognition. Mol Pharmacol 77, 159-170.
3. Le, Y., Murphy, P. M., and Wang, J. M. (2002). Formylpeptide receptors revisited. Trends Immunol 23, 541-548.
4. Yao, X. H., Liu, Y., Chen, K., Gong, W., Liu, M. Y., Bian, X. W., and Wang, J. M. (2011). Chemoattractant receptors as pharmacological targets for elimination of glioma stem-like cells. Int Immunopharmacol 11, 1961-1966.
5. Yao, X. H., Ping, Y. F., Chen, J. H., Chen, D. L., Xu, C. P., Zheng, J., Wang, J. M., and Bian, X. W. (2008). Production of angiogenic factors by human glioblastoma cells following activation of the G-protein coupled formylpeptide receptor FPR. J Neurooncol 86, 47-53.
6. Zhou, Y., Bian, X., Le, Y., Gong, W., Hu, J., Zhang, X., Wang, L., Iribarren, P., Salcedo, R., Howard, O. M., et al. (2005). Formylpeptide receptor FPR and the rapid growth of malignant human gliomas. J Natl Cancer Inst 97, 823-835.
7. Le, Y., Gong, W., Tiffany, H. L., Tumanov, A., Nedospasov, S., Shen, W., Dunlop, N. M., Gao, J. L., Murphy, P. M., Oppenheim, J. J., et al. (2001). Amyloid (beta)42 activates a G-protein-coupled chemoattractant receptor, FPR-like-1. J Neurosci 21, RC123.
8. Le, Y., Yazawa, H., Gong, W., Yu, Z., Ferrans, V. J., Murphy, P. M., and Wang, J. M. (2001). The neurotoxic prion peptide fragment PrP (106-126) is a chemotactic agonist for the G protein-coupled receptor formyl peptide receptor-like 1, J Immunol 166, 1448-1451.
9. Su, S. B., Gong, W., Gao, J. L., Shen, W., Murphy, P. M., Oppenheim, J. J., and Wang, J. M. (1999). A seven-transmembrane, G protein-coupled receptor, FPRL1, mediates the chemotactic activity of serum amyloid A for human phagocytic cells. J Exp Med 189, 395-402.
10. He, R., Sang, H., and Ye, R. D. (2003). Serum amyloid A induces IL-8 secretion through a G protein-coupled receptor, FPRL1/LXA4R. Blood 101, 1572-1581.
11. Gavins, F. N. (2010). Are formyl peptide receptors novel targets for therapeutic intervention in ischaemia-reperfusion injury? Trends Pharmacol Sci 31, 266-276.
12. Gavins, F. N., Hughes, E. L., Buss, N. A., Holloway, P. M., Getting, S. J., and Buckingham, J. C. (2012). Leukocyte recruitment in the brain in sepsis: involvement of the annexin 1-FPR2/ALX anti-inflammatory system. FASEB J 26, 4977-4989.
13. Riviere, S., Challet, L., Fluegge, D., Spehr, M., and Rodriguez, I. (2009). Formyl peptide receptor-like proteins are a novel family of vomeronasal chemosensors. Nature 459, 574-577.
14. Dufton, N., and Perretti, M. (2010). Therapeutic anti-inflammatory potential of formyl-peptide receptor agonists. Pharmacol Ther 127, 175-188.
15. Young, S. M., Bologa, C., Prossnitz, E. R., Oprea, T. I., Sklar, L. A., and Edwards, B. S. (2005). High-throughput screening with HyperCyt flow cytometry to detect small molecule formylpeptide receptor ligands. J Biomol Screen 10, 374-382.
16. Young, S. M., Bologa, C. M., Fara, D., Bryant, B. K., Strouse, J. J., Arterburn, J. B., Ye, R. D., Oprea, T. I., Prossnitz, E. R., Sklar, L. A., et al. (2009). Duplex high-throughput flow cytometry screen identifies two novel formylpeptide receptor family probes. Cytometry A 75, 253-263.
17. Edwards, B. S., Bologa, C., Young, S. M., Balakin, K. V., Prossnitz, E. R., Savchuck, N. P., Sklar, L. A., and Oprea, T. I. (2005). Integration of virtual screening with high-throughput flow cytometry to identify novel small molecule formylpeptide receptor antagonists. Mol Pharmacol 68, 1301-1310.
18. Unitt, J., Fagura, M., Phillips, T., King, S., Perry, M., Morley, A., MacDonald, C., Weaver, R., Christie, J., Barber, S., et al. (2011). Discovery of small molecule human FPR1 receptor antagonists. Bioorg Med Chem Lett 21, 2991-2997.
19. Morley, A. D., King, S., Roberts, B., Lever, S., Teobald, B., Fisher, A., Cook, T., Parker, B., Wenlock, M., Phillips, C., et al. (2012). Lead optimisation of pyrazoles as novel FPR1 antagonists. Bioorg Med Chem Lett 22, 532-536.
20. Khlebnikov, A. I., Schepetkin, I. A., Kirpotina, L. N., Brive, L., Dahlgren, C., Jutila, M. A., and Quinn, M. T. (2012). Molecular docking of 2-(benzimidazol-2-ylthio)-N-phenylacetamide-derived small-molecule agonists of human formyl peptide receptor 1. J Mol Model 18, 2831-2843.
21. Schepetkin, Kirpotina, L. N., Khlebnikov, A. I., and Quinn, M. T. (2007). High-throughput screening for small-molecule activators of neutrophils: identification of novel N-formyl peptide receptor agonists. Mol Pharmacol 71, 1061-1074.

22. Schepetkin, I. A., Kirpotina, L. N., Tian, J., Khlebnikov, A. I., Ye, R. D., and Quinn, M. T. (2008). Identification of novel formyl peptide receptor-like 1 agonists that induce macrophage tumor necrosis factor alpha production. Mol Pharmacol 74, 392-402.
23. Cilibrizzi, A., Quinn, M. T., Kirpotina, L. N., Schepetkin, I. A., Holderness, J., Ye, R. D., Rabiet, M. J., Biancalani, C., Cesari, N., Graziano, A., et al. (2009). 6-methyl-2,4-disubstituted pyridazin-3(2H)-ones: a novel class of small-molecule agonists for formyl peptide receptors. J Med Chem 52, 5044-5057,
24. Burli, R. W., Xu, H., Zou, X., Muller, K., Golden, J., Frohn, M., Adlam, M., Plant, M. H., Wong, M., McElvain, M., et al. (2006). Potent hFPRL1 (ALXR) agonists as potential anti-inflammatory agents. Bioorg Med Chem Lett 16, 3713-3718.
25. Frohn, M., Xu, H., Zou, X., Chang, C., McElvaine, M., Plant, M. H., Wong, M., Tagari, P., Hungate, R., and Burli, R. W. (2007). New 'chemical probes' to examine the role of the hFPRL1 (or ALXR) receptor in inflammation. Bioorg Med Chem Lett 17, 6633-6637.
26. Houghten, R. A., Pinilla, C., Appel, J. R., Blondelle, S. E., Dooley, C. T., Eichler, J., Nefzi, A., and Ostresh, J. M. (1999). Mixture-based synthetic combinatorial libraries. J Med Chem 42, 3743-3778,
27. Houghten, R. A., Pinilla, C., Giulianotti, M. A., Appel, J. R., Dooley, C. T., Nefzi, A., Ostresh, J. M., Yu, Y., Maggiora, G. M., Medina-Franco, J. L., et al. (2008). Strategies for the use of mixture-based synthetic combinatorial libraries: scaffold ranking, direct testing in vivo, and enhanced deconvolution by computational methods. J Comb Chem 10, 3-19.
28. Pinilla, C., Appel, J. R., Blanc, P., and Houghten, R. A. (1992). Rapid identification of high affinity peptide ligands using positional scanning synthetic peptide combinatorial libraries. Biotechniques 13, 901-905.
29. Dooley, C. T., and Houghten, R. A. (1993). The use of positional scanning synthetic peptide combinatorial libraries for the rapid determination of opioid receptor ligands. Life Sci 52, 1509-1517.
30. Lopez-Vallejo, F., Giulianotti, M. A., Houghten, R. A., and Medina-Franco, J. L. (2012). Expanding the medicinally relevant chemical space with compound libraries. Drug Discov Today 17, 718-726.
31. Medina-Franco, J. L., Martinez-Mayorga, K., Bender, A., Marin, R. M., Giulianotti, M. A., Pinilla, C., and Houghten, R. A. (2009). Characterization of activity landscapes using 2D and 3D similarity methods: consensus activity cliffs. J Chem Inf Model 49, 477-491.
32. Maggiora, G. M. (2006). On outliers and activity cliffs— why QSAR often disappoints. J Chem Inf Model 46, 1535.
33. Pinilla, C., Appel, J. R., Borras, E., and Houghten, R. A. (2003). Advances in the use of synthetic combinatorial chemistry: mixture-based libraries. Nat Med 9, 118-122.

EXAMPLE 2

Selective Agonists and Antagonists of Formylpeptide Receptors: Duplex Flow Cytometry and Mixture-Based Positional Scanning Libraries
Materials and Methods
Preparation of Mixture-Based Libraries and Individual Compounds. Employing solid-phase chemistry approaches, mixture-based libraries were synthesized from resin-bound amino acids, peptides, and peptidomimetics as starting materials using the simultaneous multiple synthesis and "libraries from libraries" approaches as previously described (Houghten, 1985; Houghten, et al., 1991; Houghten, et al., 1999; Nefzi, et al., 2004; Ostresh, et al., 1994a). Extensive optimization of each reaction condition was necessary for mixture library generation. The isokinetic ratios necessary for equimolar incorporation of amino acids (Ostresh, et al., 1994b) and carboxylic acids (Acharya, et al., 2002) as well as other reagents have previously been determined. Synthetic controls are prepared systematically to determine a wide range of building blocks to be incorporated into varied reactive positions of a given central scaffold molecule. Supplemental Table 1 (FIG. 2EX9) contains information on 37 small molecule libraries screened against FPR1 and FPR2. Three peptide libraries (totaling 26 million compounds; libraries 6, 7, and 33 in Supplemental Table 1) were screened, but were excluded in the deconvolution or analysis of the screening efficiency (Table 1). In most cases, libraries were dissolved in DMF at 10 mg/ml and diluted in water for final testing concentrations. The synthesis of library 1344 (including 1343, 1345, 1346 and 1347) has been previously described (Reilley, et al., 2010). In brief, library 1344 was synthesized using the "libraries from libraries" approach (Nefzi, et al., 2004; Ostresh, et al., 1994a) starting with resin-bound N-acylated peptides (Hensler, et al., 2006) that were subsequently exhaustively reduced with borane-THF. No loss of chirality was found in either the reduction or subsequent steps. The resin bound polyamine was then treated with oxyalyldiimidazole to form the resin bound pyrrolidine bis-diketopiperazine before cleavage from the resin. The library was synthesized in a positional scanning format with four positions of diversity (Supplemental Table 2, FIG. 2EX10). Each separate sublibrary ($R_1$-$R_4$) was synthesized representing the same diversity and differing solely by the location of the defined position, allowing for library screening and deconvolution essentially as described (Pinilla, et al., 1992; Pinilla, et al., 2003). The synthesis of library 1481 has been described elsewhere (Nefzi, et al., 2000; Schimmer, et al., 2004). In brief, library 1481 was synthesized starting with resin-bound N-acylated dipeptides that were exhaustively reduced with borane-THF followed by treatment with phenylisocynate to afford the resin-bound polyphenyl ureas, which were subsequently removed from the solid support. Library 1481 was synthesized in a positional scanning format with three positions of diversity. The $R_1$ and $R_2$ positions were prepared with the same 48 functionalities and $R_3$ was prepared with 39 functionalities (48×48×39=89,856, see Supplemental Table 2). Each separate sublibrary ($R_1$-$R_3$) was synthesized representing the same diversity and differing solely by the location of the defined position, allowing for library screening and deconvolution essentially as described (Pinilla, et al., 1992; Pinilla, et al., 2003). Individual compounds derived from libraries 1344 and 1481 were synthesized by the same solid-phase methods used for the libraries and analyzed by LCMS to confirm identity and purity. The individual compounds shown in Table 2 were all purified by RP-HPLC and had a final purity of >99% as determined by integration of the absorbance at 254 nm. (The LCMS data for these compounds can be found in the Supplemental FIG. 1, FIG. 2EX10 and Supplemental Table 3, FIG. 2EX11) (Example 2). Additional analytical information based on LCMS for all 106 TPI compounds can be found in Datasets S1 and S2. It should be noted that for the compounds that contain a phenyl group in the $R_3$ position (such as Table 2 compound a: 1754-113) the final product is close to 50:50 racemic mixture of the S, R-phenyl.

Flow cytometry receptor binding assay. The assay was performed in a "duplex" format in which U937/FPR1 cells were tested together with RBL/FPR2 cells as previously described (Young, et al., 2009)(PubChem Summary AIDs 805 and 1202). The FPR1-expressing cells were stained with a red-fluorescent dye, FuraRed™ allowing them to be distinguished from the FPR2-expressing cells during flow cytometric analysis. A fluorescein label was conjugated to the lysine residue of the WPep peptide (WKYMVm) to produce a fluorescent ligand (WPep-FITC) that bound both FPR1 and FPR2. Dissociation constants ($K_d$) for binding of WPep-FITC to FPR1 and FPR2 were determined to be 1.2 nM and 1.8 nM, respectively. Assays were performed in polystyrene 384-well plates with small volume wells (Greiner #784101). Additions to wells were in sequence as follows: (1) test compounds and control reagents (5 ul/well); (2) the combined suspension of U937/FPR1 and RBL/FPR2 cells (5 ul/well) and; (3) (after 30 min, 4° C. incubation) WPep-FITC (5 ul/well). After an additional 45 min, 4° C. incubation, plates were immediately analyzed using flow cytometry. The assay response range was defined by replicate control wells containing unlabeled receptor-blocking peptide (positive control) or buffer (negative control). fMLFF was used as the FPR1-blocking peptide and unlabeled WPep as the FPR2-blocking peptide. Final concentration of WPep-FITC was 5 nM. The assay was homogeneous in that cells, compounds and fluorescent peptide were added in sequence and the wells subsequently analyzed without intervening wash steps. The HyperCyt™ high-throughput flow-cytometry platform (Kuckuck, et al., 2001; Ramirez, et al., 2003) was used to sequentially sample cells from wells of 384-well microplates (2 ul/sample) for presentation to a CyAn flow cytometer (Beckman-Coulter) at a rate of 40 samples/min. Fluorescence was excited at 488 nm and detected with 530/40 and 680/30 optical bandpass filters for WPep-FITC and FuraRed™, respectively. Test compound inhibition of fluorescent peptide binding was calculated as percent inhibition. WPep-FITC fluorescence intensity measurements of cells from control wells were also used to calculate Z' factors (Zhang, et al., 1999), which ranged between 0.6 and 0.8 for each assay.

Intracellular calcium mobilization assays. Intracellular calcium mobilization assays were performed as previously described with modifications (Edwards, et al., 2005). Briefly, cells were collected by centrifugation (200×g, 10 min, 24° C.) and suspended at $10^6$/ml in 1 ml PBS ($Ca^{2+}$, $Mg^{2+}$ free). Cells were added with 210 nM Fluo4 (FPR2 cells) or with a combination of 210 nM Fluo4 and 210 nM FuraRed (FPR1 cells). After incubation for 30 min at 24° C. cells were washed with 1 ml PBS, suspended in 1 ml TCM (RPMI, 10% FBS) and stored in the dark at 24° C. until used in assays. For test compound agonist determinations, 50 µL from FPR1 and FPR2 cell suspensions were combined, analyzed 10 s in an Accuri C6 flow cytometer (BD Biosciences) to determine baseline Fluo4 fluorescence in the FL1 channel (530/20 nm), then added with 50 µL containing test compounds and analyzed an additional 110 s to evaluate changes in Fluo4 fluorescence intensity. During the analysis FPR1 cells were distinguished from FPR2 cells on the basis of FuraRed fluorescence intensity detected in the FL3 channel (>610 nM). The innate calcium response was quantified as the maximum % of cells that exceeded the baseline Fluo4 fluorescence intensity over the course of the analysis. These responses were normalized to the innate calcium responses observed in the presence of 11 nM control peptides: 4pep for FPR1 cells and Wpep for FPR2 cells as follows:

Normalized Calcium Response (%)=100×innate response % to test compound/innate response % to control peptide.

For test compound antagonist determinations, 10 µL test compound was added to the combined FPR1/FPR2 cell mixture and incubated 5 min at 24° C. prior to assessing the innate calcium response to subsequent addition of fMLFF or Wpep peptide. In these determinations, fMLFF and Wpep were used at concentrations that produced 90% of the maximal intracellular calcium response ($EC_{90}$), and responses were normalized with respect to the innate response to each control peptide observed in the absence of test compounds.

Dose response determinations. Fluorescent ligand competition dose response assays were performed essentially as described for single concentration assays except that test compounds were initially tested at a starting concentration of 10 mM in DMSO and serially diluted 1:3 to produce final concentration ranging from 67 µM to 0.1 nM. The resulting ligand competition curves were fitted by Prism software (GraphPad Software, Inc., San Diego, Calif.) using nonlinear least-squares regression in sigmoidal dose response model with variable slope, also known as the four parameter logistic equation. Two parameters, the top and bottom of the fitted curves, were fixed at 100 and 0, the expected upper and lower boundaries of normalized data. Curve fit statistics were used to determine the concentration of added test compound competitor that inhibited fluorescent ligand binding by 50 percent ($IC_{50}$).

FPR expression ranged from 100,000 to 200,000 receptors per cell in different assays as determined by comparison to standard curves generated with Fluorescein Reference Standard Microbeads (Bangs Laboratories, Fishers, Ind.). This corresponds to total FPR concentration of 0.6 to 1.2 nM. To account for effects of possible ligand depletion at the higher receptor concentrations, $K_i$ values were calculated from $IC_{50}$ estimates by the method of Munson and Rodbard (Munson and Rodbard, 1988): $K_i=K_d\times[y0/(y0+2]+IC_{50}/\{1+[p^*\times(y0+2)]/[2\times K_d\times(y0+1)]+y0\}$ in which y0 is the initial bound-to-free concentration ratio for the fluorescent ligand, p* is the added concentration of fluorescent ligand and $K_d$ is the dissociation constant for the fluorescent ligand.

Intracellular $Ca^{2+}$ dose response curves were also fitted using nonlinear least-squares regression in a sigmoidal dose response model with variable slope. Curve fit statistics were used to determine the concentration of added test compound competitor that inhibited $Ca^{2+}$ responses by 50 percent ($IC_{50}$) for antagonists or effected increases in $Ca^{2+}$ response by 50% ($EC_{50}$) for agonists. Since responses were normalized relative to control stimuli the top and bottom of the fitted curves were fixed at 100 and 0.

Results

In the search for novel FPR ligands we have used four distinctive screening programs (Table 1, FIG. 2EX4). For two of these programs we also evaluated FPR1 and FPR2 ligand binding activity in parallel. All four studies used competitive displacement of a fluorescent ligand as the primary screening methodology but each differed with respect to the composition of the compound library and conceptual design of the screening program. The earliest (Young, et al., 2005) was a screen of a commercial collection of 880 off-patent drugs and alkaloids, the Prestwick Chemical Library (PCL), in which we confirmed the previously reported FPR1 binding activity of sulfinpyrazone (Levesque, et al., 1991) but failed to detect novel ligands of greater potency (Table 1: PCL). The next involved the screening of a focused library containing 4,234 small molecule compounds. The library was constructed on the basis of a preliminary computational screen of 480,000 compounds from the commercial ChemDiv collection using an FPR homology model and pharmacophore (Edwards, et al., 2005). From several chemically distinct families of FPR1 ligands identified, the most potent was an antagonist with a $K_i$ of 1 µM (Table 1: Focused, Line 2). In the third approach we screened a subset of the NIH Molecular Libraries Small Molecule Repository (MLSMR), a small molecule diversity library of 24,304 compounds (Young, et al., 2009). Computational SAR analysis of active compounds from the first round of screening resulted in the commercial procurement and testing of an additional 1,446 small molecules. Seven FPR1 ligands and 1 FPR2 ligand with submicromolar potency were identified and all were antagonists (Table 1: MLSMR). In each of these first three screening approaches the physical screening component involved analysis of 1 test compound/well.

The fourth screening approach is presented here and involved the screening of a collection of mixture based combinatorial libraries, of which more than 5 million are classic small molecule compounds (Table 1: TPIMS Library, Line 1). This collection is made up of 5,261 mixtures ranging from 48 to 216,000 compounds per mixture. Based on the screening results for FPR1 and FPR2 described below, two different libraries were selected for deconvolution to identify individual compounds. From one library, 106 individual compounds (Table 1: 1754) were synthesized and evaluated, of which 56 compounds had $K_i$ values ≤1 µM for FPR1 and 38 had $K_i$ values ≤1 µM for FPR2. Additionally from the deconvolution of a second library, 8 individual compounds (Table 1: 1753) were evaluated, of which 7 had $K_i$ values ≤1 µM in FPR1.

As is evident from the results elucidated in Table 1, the set of active compounds ($K_i$<1 µM) generated from the mixture-based combinatorial libraries contains compounds which are more active and more selective towards each target than those sets previously obtained from any of the other screening methods performed. In addition to the superiority of these results, positional scanning of combinatorial libraries offers additional advantages to the alternative screening methods attempted. The first is efficiency, as assessed solely by the number of samples tested; given a hit rate in MLSMR of 8/24,304, the probability of randomly testing only 5,375 samples (5,261 mixtures+114 individual compounds, Table 1 FIG. 2EX4) and having at least 100 total positive hits is essentially zero ($p \leq 4.2 \times 10^{-133}$). Another way to assess screening efficiency is the number of active compounds identified relative to the total number of samples initially tested. In our previous screen of the MLSMR collection we evaluated 24,304 samples to identify 7 hit compounds for FPR1 and 1 for FPR2 (Table 1, FIG. 2EX4), hit frequencies of ~0.03% and ~0.004%, respectively. In the present study, 5,261 samples were initially screened to obtain hit frequencies of 1.1% for FPR1 and 0.6% for FPR2. In comparison with the MLSMR screen this represented a 37-fold and 150-fold increase in hit identification efficiency, respectively.

Primary screening of mixtures. The TPIMS collection of mixture based combinatorial libraries containing 37 different small molecule scaffolds were formatted on 19 separate 384-well plates (1 mixture sample per well) and screened in the duplex flow cytometry assay for inhibition of the FITC-labeled Wpep peptide binding to FPR1 and FPR2 receptors. The results of the screen in both receptors are shown in FIG. 1, FIG. 2EX1. Each of the 37 libraries is numbered and grouped by color, and the inhibitory activity for each of the 5,261 mixtures is shown. Supplemental Table 1 contains detailed information for the 37 mixture based libraries. This includes the library synthesis number, the number of mixture samples tested, the number of compounds per mixture, the total number of compounds in each library, the library name and its chemical structure. A number of libraries showed inhibitory activity for both receptors. Library 21 was one of the most active libraries for both receptors, whereas library 36 was the most active in FPR1 alone. These two libraries were selected for further testing and deconvolution. It is worth noting that other libraries showed modest activity that could also be pursued. Thus, even in the duplex primary screen, a range of pharmacological possibilities were revealed.

Library 21 is a positional scanning library with four positions of diversity. It is a pyrrolidine bis-diketopiperazine scaffold (library 1344 in Supplemental Table 1). The mixtures for $R_1$ (1-26), $R_2$ (27-52), and $R_3$ (53-78) were each defined with one of 26 functionalities and each mixture was composed of 28,392 compounds (26×26×42=28,392). The mixtures for $R_4$ (79-120) were each defined with one of 42 functionalities and each mixture was composed of 17,576 compounds (26×26×26=17,576). The building blocks and the resulting functionalities of each of the mixtures are shown in Supplemental Table 2. Each of the 120 mixtures for this library was retested in a series of confirmatory screens for their inhibitory binding activity of FPR1 and FPR2 receptors. The average and standard error of the mean of different screens (n=4-7) for each mixture in each diversity position is shown in Supplemental FIG. 2, FIG. 2EX9.

Positional scanning deconvolution. Identification of the individual compounds responsible for library 21 activity was carried out using positional scanning deconvolution {Pinilla, 1992 2723 /id;Dooley, 1993 2666 /id;Houghten, 1999 10071 /id;Houghten, 2008 16970 /id}, in which the functionalities in each of the defined positions of the most active mixtures within each library were selected to design a set of individual compounds. The most active mixtures for each of the receptors were tested in a dose response manner and this information was taken into consideration in the selection of the functionalities from each position. The most differential inhibitory activity was seen in $R_1$, $R_2$ and $R_3$. Some of the most active mixtures (>40% inhibition) for one receptor were among the least active for the other receptor. In $R_4$ the overall inhibitory activity was lower and little difference was seen between receptors. The selection of functionalities for the synthesis of individual compounds was solely based on activity and not selectivity. The functionalities and the corresponding mixture number (Supplemental Table 2, FIG. 2EX10 and Supplemental FIG. 2, FIG. 2EX6) used for the synthesis of individual compounds for FPR1 included: S-benzyl (#2), S-propyl (#19), and S-butyl (#21) in $R_1$; S-benzyl (#28), S-isobutyl (#31), S-hydroxymethyl (#40), R-propyl (#46) and R-butyl (#48) in $R_2$; S-2-butyl (#56), R-4-hydroxybenzyl (#69), S-phenyl (#70) and S-cyclohexyl (#77) in $R_3$; and cyclohexyl-methyl (#107), 4-methyl-1-cyclohexyl-methyl (#115) and 2-biphenyl-4-yl ethyl (#117) in $R_4$. For the individual compounds for FPR2 the functionalities were: S-isopropyl (#8), S-propyl (#19) and R-2-naphthylmethyl (#24) in $R_1$; R-4-hydroxybenzyl (#43), R-propyl (#46), R-2-naphthylmethyl (#50) and R-cyclohexyl (#52) in $R_2$; R-benzyl (#63), R-4-hydroxybenzyl (#69), R-propyl (#72), and R-butyl (#74) in $R_3$; and cyclohexyl-methyl (#107), 4-methyl-1-cyclohexyl-methyl (#115) and 2-biphenyl-4-yl ethyl (#117) in $R_4$. A total of 106 compounds (Table 1: 1754) were synthesized and tested at both receptors.

FIG. 2EX7 shows a scatter plot of the activity of individual compounds for both receptors. The structural information and inhibitory binding activities for all 106 compounds are given in Supplemental Dataset 1. Nineteen different compounds of the 106 pyrrolidine bis-diketopiperazines were identified with $K_i$ values less than 100 nM for FPR1, of which 15 are FPR1 selective with $K_i$ values more than 100 fold greater for FPR2. For the FPR2 receptor, 23 out of the 106 compounds have $K_i$ values less than 100 nM and of those 12 were selective for FPR2 with $K_i$ values more than 100 fold greater for FPR1.

A visualization of the SAR for the inhibitory binding activity of the 106 diketopiperazine individual compounds is shown in FIG. 3. The figure summarizes the distribution of the inhibitory activity $(K_i)$ values for compounds with a given R-group. Activity is color-coded with a continuous scale from more active (red) to less active (green). The most representative R-groups (i.e., with three or more compounds) are displayed. This visual representation of the SAR clearly shows striking differences in the general activity and selectivity pattern of R-groups. For example, FIG. 2EX3 highlights the overall increased activity for FPR2 when small and aliphatic substituents are utilized in $R_1$, in particular S-isopropyl. In general, bulky and aromatic rings in $R_1$ decrease the activity. In contrast, S-benzyl in $R_1$ is favorable for activity for FPR1. A large and hydrophobic moiety in $R_1$ such as R-naphthyl is not tolerated for either FPR1 or FPR2. For $R_2$, FIG. 2EX3 visually emphasizes the selectivity for FPR2 when R-4-hydroxymethyl or R-2-naphthylmethyl is utilized. Strikingly the selectivity switches to FPR1 when the aromatic S-benzyl is utilized instead at $R_2$. This switch in selectivity might be due to either the switch in stereochemistry or from the subtle structural differences in this set of aromatic substitutions. The small and polar S-hydroxymethyl group in $R_2$ leads to inactive compounds for FPR1 and FPR2.

Extended functional analysis. Two FPR1 selective compounds from the pyrrolidine bis-diketopiperazine library, namely 1754-113 and 1754-56, are shown in Table 2, FIG. 2EX5 along with that of compound 1754-26, which is the only compound out of the 106 tested with a $K_i$ value less than 100 nM for both receptors. These 3 compounds acted as antagonists when tested for their ability to elicit or inhibit FPR1-mediated intracellular $Ca^{2+}$ response (Table 2). By contrast, the two compounds exhibited opposite effects in parallel analyses of $Ca^{2+}$ responses mediated by FPR2. 1754-56 was an agonist for FPR2, with a low micromolar $EC_{50}$ that matched the $K_i$ value observed in the competitive ligand displacement assay (Table 2, FIG. 2EX5 and Supplemental FIG. 3, FIG. 2EX7). 1754-56 and 1754-26 differ at the $R_1$ functionality, which is S-butyl and S-isopropyl, respectively. Thus, a subtle change in the structure plays a dramatic role in selectivity for these ligands, representing a clear example of an 'activity cliff'.

Three FPR2 selective pyrrolidine bis-diketopiperazines (1754-20, 1754-19, and 1754-31) are also shown in Table 2. It can be seen that the only difference between the non-selective inhibitor, 1754-26, and the FPR2-selective inhibitor, 1754-20, is the $R_2$ functionality, which is R-propyl for the former and R-4-hydroxybenzyl for the latter. Another significant functional disparity resulted when the S-isopropyl $R_1$ functionality of 1754-31 was replaced with an S-propyl functionality in 1754-49. Not only was there a decrease in FPR2 selectivity (>10,000 to ~70) but the antagonist (1754-31) was converted to partial agonist (1754-49) in the FPR2-mediated $Ca^{2+}$ response determinations (Table 2, Supplemental FIG. 3).

As shown in FIG. 2EX1, library 36 (Library 1481 in Supplemental Table 1, FIG. 2EX4) was clearly more active at FPR1 than FPR2. This library is made up of a polyphenylurea scaffold having three positions of diversity. Each mixture contains 1,777-2,304 compounds while the entire library contains 85,248 compounds. Eight individual compounds (Table 1: 1753) were designed based on the deconvolution of the library screening data in FPR1, and the results of the 4 most active and selective compounds ($K_i$ values 1-24 nM) are shown in Supplemental Dataset 2. 1753-101, 1753-102 and 1753-103 (Table 2) were determined to be selective partial agonists for FPR1 in intracellular $Ca^{2+}$ response determinations, as illustrated in a representative dose-response profile for 1754-103 in Supplemental FIG. 2EX7.

Discussion

The rapid and efficient identification of potent and selective FPR ligands presented in this work is in accord with our previous findings that screening of mixture-based libraries enables the rapid exploration of novel regions of the chemical space not typically covered by commercially available screening compounds. The results of screening mixture-based combinatorial libraries over traditional HTS of commercially available small-molecule libraries to identify potent and selective FPR ligands are compared in Table 1, FIG. 2EX4. These results clearly show that the use of mixture-based libraries in a duplex HTS system was a more efficient and robust approach for the primary screening stage than the other approaches involving the screening of 1 compound/well. In the present study, 5,261 samples were initially screened to obtain hit frequencies of 1.1% for FPR1 and 0.6% for FPR2. In comparison with the MLSMR screen this represented a 37-fold and 150-fold increase in hit identification efficiency, respectively. This indicates that positional scanning of mixture-based combinatorial libraries was significantly more efficient than random testing when evaluated by virtually any standard of significance chosen. It should be noted that the number of total compounds evaluated by the mixture libraries in this study (including 5 million small molecule compounds) is beyond the range of feasibility for most single-compound screening efforts.

Screening of the highly dense region of chemical space covered by the active libraries tested herein led to the identification of potent and highly selective ligands and also provided substantial and useful structure-activity relationship (SAR) information. The individual compounds generated from a positional scanning deconvolution are especially well-suited to SAR analysis, since one can immediately analyze the effect that single- or double-substitutions at individual positions have on the activities of these compounds (see more below). This SAR allows for the identification of the causes of activity cliffs that cannot be readily accomplished in libraries of individual compounds of disparate scaffolds. Thus, the exhaustive exploration of the SAR of the most active libraries readily revealed the presence of activity cliffs, chemical compounds with highly similar structures, but unexpectedly very different biological activities.

Recently, two separate groups have identified potent small molecule FPR1 antagonists with $Ca^{2+}$ response $IC_{50}$ values of 398 nM (Unitt, et al., 2011) and 4 nM (Morley, et al., 2012). Small molecule FPR1 agonists have also been identified in a number of recent studies (Cilibrizzi, et al., 2009; Kirpotina, et al., 2010; Schepetkin, et al., 2007), the most potent of which had a $Ca^{2+}$ response $EC_{50}$ value of 630 nM (Schepetkin, et al., 2007). Potent FPR2 agonists have also been reported with $Ca^{2+}$ response $EC_{50}$ values in the 30-40 nM range (Burli, et al., 2006; Frohn, et al., 2007). The compounds reported here include the most potent FPR1 agonist (1753-103) and FPR2 antagonist (1754-31) identified to date. These compounds are structurally distinct from all previously described FPR ligands. In intracellular $Ca^{2+}$ response determinations the FPR1 agonist had an $EC_{50}$ of 131 nM (binding affinity 4 nM $K_i$) and the FPR2 antagonist had an $IC_{50}$ of 81 nM (binding affinity 1 nM $K_i$).

The SAR findings summarized in Table 2, FIG. 2 EX5 and FIG. 2EX3 for the FPR1 and FPR2 ligands suggest the importance of S-butyl in the $R_1$ functionality for FPR1 active and selective ligands and R-4-hydroxybenzyl in the $R_2$ functionality for FPR2 active and selective ligands. More extensive structural activity analysis of the 106 compounds supports the importance of these functionalities. The functionalities that are more frequently found in the active and selective compounds for each of the receptors are: 1) For FPR1, in $R_1$ S-butyl and S-benzyl and in $R_2$ R-propyl and S-benzyl; and 2) For FPR2, in $R_1$ S-isopropyl followed by S-propyl and in $R_2$ R-4-hydroxymethyl and R-2-naphthylmethyl. It is important to note that even in the primary screen the mixtures with these functionalities show clear selectivity. For example in library mixture 1344-8 $R_1$ is defined with S-isopropyl and is active for FPR2 while library mixture 1344-21 is defined with S-butyl and shows significantly greater activity for FPR1 than FPR2 (Supplemental FIG. 2EX6 and Supplemental Table 2, FIG. 2EX10). Although there are specific R-groups with marked differences in activity for FPR1 and FPR2, FIG. 2EX3 and the activity data for individual compounds in Table 2 also indicate that there are specific combinations of R-groups that determine the activity and selectivity of the individual ligands. In order to explore in detail the SAR of the entire data set, a systematic pairwise comparison of the structure and activity of the 106 molecules was conducted using the principles of activity landscape modeling. Results of the systematic analysis indicated that the compound pair 1754-26/1754-56 (Table 2) represents an "activity switch" where the substitution of an S-isopropyl with S-butyl at $R_1$ increases the activity for FPR1 by 1.36 log units but decreases the activity for FPR2 by 1.28 log units. The analysis also rapidly revealed that the compound pair 1754-20/1754-56 (Table 2) is a "selectivity switch" because changes in the R-groups have a large and opposite effect on the activity for FPR1 and FPR2. These and other conclusions from the comprehensive SAR analysis based on the structure of the 106 ligands are reported elsewhere (Medina-Franco, et al., 2013). The structure-activity analysis derived from the deconvolution of positional scanning libraries provides useful information about the importance of the functionalities at each position of the compound, which can then be used as a starting point for a more detailed characterization of the functionalities required for activity and selectivity.

Discrimination between agonists and antagonists in this study was based on elevation of intracellular calcium. We have shown previously that in these assay systems, the cellular response reflects a distribution of responding and non-responding cells which are captured in the current analysis and can distinguish among antagonists as well as full and partial agonists. Thus, the collection of FPR1 and FPR2 agonists and antagonists we report here adds to the FPR1/FPR2 ligands identified and characterized by different groups. The ligands identified cover divergent structural classes, but in some cases the ligands within structural classes display similar functional activity, i.e., piperazines as selective FPR2 agonists (Kirpotina, et al., 2010). However there are several examples from these studies, including our own, in which compounds derived from similar scaffolds have divergent functional activity against FPR1 and FPR2, such as an apparently slight modification in structure changes a ligand from a selective agonist to a selective antagonist. For instance t-Boc peptides have been reported as FPR1 antagonists while the N-formyl peptides of the same or similar composition are FPR1 agonists (Ye, et al., 2009). The synthetic, nonpeptide FPR2 agonist (Quin-C1) differs from the FPR1 antagonist Quin-C7 only in the para position of the phenyl ring, methoxy (Quin-C1) to hydroxyl (C7) (Zhou, et al., 2007). In the current study modification of the $R_1$ propyl functionality of the FPR2 agonist (1754-49) to an isopropyl yielded an FPR2 antagonist (1754-31), Additionally there are examples of what appear to be small structural modifications that change a ligand from a target selective functionality to a non-selective functionality against FPR1 and FPR2. For instance, Khlebnikov et al. report that by modifying the p-$COOCH_3$ group on their benzimidazole selective FPR1 agonist (AG-11/05) to a m-$COCH_3$ group they obtained the dual FPR1/FPR2 agonist (AG-11/06) (Khlebnikov, et al., 2012). In a similar manner we observed that the modification of the phenol portion of the $R_2$ functionality of the FPR2 selective antagonist (1754-20) to a methyl group yielded the dual FPR1/FPR2 antagonist (1754-26) (FIG. 2EX8). The accumulated SAR to date supports the high degree of homology between the FPR targets. The ligands in which slight structural modifications produce a dramatic shift in functionality holds promise for the identification of therapeutically relevant, target/functionality specific compounds. Additionally the breadth of structural classes reported to date for FPR1 and FPR2 indicates that many structural motifs are available for these targets, expanding the range of medicinal chemistry space available for optimization of leads.

The use of positional scanning libraries with a duplex HTS approach enabled the identification of compounds with diverse functional activities (selective agonist, selective antagonist, dual antagonist, mixed agonist/antagonist) containing a wealth of SAR from the screening 5,261 samples. It is important to note that more than 5 million small molecules were assessed in this approach. Such a wealth of data lends itself to a broad analysis and quantification of the overall screening process, which will be reported elsewhere (Santos, et al., 2013). We anticipate that the combined approaches illustrated herein, in which mixture-based positional scanning libraries are screened in a variety of differing targets and assay formats, such as the duplex flow cytometry utilized in the current studies, will facilitate and accelerate a wide range of translational drug discovery efforts. Finally, it is worth noting that while the exploration of two libraries has revealed extraordinary pharmacological diversity, other opportunities within the TPIMS chemical space, such as libraries 8, 22, 23, 24, and 28, remain to be explored.

References for Example 2

Acharya A N, Ostresh J M and Houghten R A (2002) Determination of isokinetic ratios necessary for equimolar incorporation of carboxylic acids in the solid-phase synthesis of mixture-based combinatorial libraries. *Biopolymers* 65:32-39.

Burli R W, Xu H, Zou X, Muller K, Golden J, Frohn M, Adlam M, Plant M H, Wong M, McElvain M, Regal K, Viswanadhan V N, Tagari P and Hungate R (2006) Potent hFPRL1 (ALXR) agonists as potential anti-inflammatory agents. *Bioorg Med Chem Lett* 16:3713-3718.

Cilibrizzi A, Quinn M T, Kirpotina L N, Schepetkin I A, Holdemess J, Ye R D, Rabiet M J, Biancalani C, Cesari N, Graziano A, Vergelli C, Pieretti S, Dal P, V and Giovannoni M P (2009) 6-methyl-2,4-disubstituted pyridazin-3 (2H)-ones: a novel class of small-molecule agonists for formyl peptide receptors. *J Med Chem* 52:5044-5057.

Clark A M and Labute P (2009) Detection and assignment of common scaffolds in project databases of lead molecules. *J Med Chem* 52:469-483.

Dooley C T and Houghten R A (1993) The use of positional scanning synthetic peptide combinatorial libraries for the rapid determination of opioid receptor ligands. *Life Sci* 52:1509-1517.

Dufton N and Perretti M (2010) Therapeutic anti-inflammatory potential of formyl-peptide receptor agonists. *Pharmacol Ther* 127:175-188.

Edwards B S, Bologa C, Young S M, Balakin K V, Prossnitz E R, Savchuck N P, Sklar L A and Oprea T I (2005) Integration of virtual screening with high-throughput flow cytometry to identify novel small molecule formylpeptide receptor antagonists. *Mol Pharmacol* 68:1301-1310.

Frohn M, Xu H, Zou X, Chang C, McElvaine M, Plant M H, Wong M, Tagari P, Hungate R and Burli R W (2007) New 'chemical probes' to examine the role of the hFPRL1 (or ALXR) receptor in inflammation. *Bioorg Med Chem Lett* 17:6633-6637.

Giulianotti M A, Debevec G, Santos R G, Maida L E, Chen W, Ou L, Yu Y, Dooley C T and Houghten R A (2012) A novel method for the determination of isokinetic ratios and its application in the synthesis of two new positional scanning libraries. *ACS Comb Sci* 14:503-512.

Hensler M E, Bernstein G, Nizet V and Nefzi A (2006) Pyrrolidine bis-cyclic guanidines with antimicrobial activity against drug-resistant Gram-positive pathogens identified from a mixture-based combinatorial library. *Bioorg Med Chem Lett* 16:5073-5079.

Houghten R A (1985) General method for the rapid solid-phase synthesis of large numbers of peptides: Specificity of antigen-antibody interaction at the level of individual amino acids. *Proc Natl Acad Sci USA* 82:5131-5135.

Houghten R A, Pinilla C, Appel J R, Blondelle S E, Dooley C T, Eichler J, Nefzi A and Ostresh J M (1999) Mixture-based synthetic combinatorial libraries. *J Med Chem* 42:3743-3778.

Houghten R A, Pinilla C, Blondelle S E, Appel J R, Dooley C T and Cuervo J H (1991) Generation and use of synthetic peptide combinatorial libraries for basic research and drug discovery. *Nature* 354:84-86.

Houghten R A, Pinilla C, Giulianotti M A, Appel J R, Dooley C T, Nefzi A, Ostresh J M, Yu Y, Maggiora G M, Medina-Franco J L, Brunner D and Schneider J (2008) Strategies for the use of mixture-based synthetic combinatorial libraries: Scaffold ranking, direct testing in vivo, and enhanced deconvolution by computational methods. *J Comb Chem* 10:3-19.

Khlebnikov A I, Schepetkin I A, Kirpotina L N, Brive L, Dahlgren C, Jutila M A and Quinn M T (2012) Molecular docking of 2-(benzimidazol-2-ylthio)-N-phenylacetamide-derived small-molecule agonists of human formyl peptide receptor 1. *J Mol Model* 18:2831-2843.

Kirpotina L N, Khlebnikov A I, Schepetkin I A, Ye R D, Rabiet M J, Jutila M A and Quinn M T (2010) Identification of novel small-molecule agonists for human formyl peptide receptors and pharmacophore models of their recognition. *Mol Pharmacol* 77:159-170.

Kuckuck F W, Edwards B S and Sklar L A (2001) High throughput flow cytometry. *Cytometry* 44:83-90.

Le Y, Murphy P M and Wang J M (2002) Formyl-peptide receptors revisited. *Trends Immunol* 23:541-548.

Le Y, Yazawa H, Gong W, Yu Z, Ferrans V J, Murphy P M and Wang J M (2001) The neurotoxic prion peptide fragment PrP (106-126) is a chemotactic agonist for the G protein-coupled receptor formyl peptide receptor-like 1. *J Immunol* 166:1448-1451.

Levesque L, Gaudreault R C and Marceau F (1991) The interaction of 3,5-pyrazolidinedione drugs with receptors for f-Met-Leu-Phe on human neutrophil leukocytes: a study of the structure-activity relationship. *Can J Physiol Pharmacol* 69:419-425.

Lopez-Vallejo F, Giulianotti M A, Houghten R A and Medina-Franco J L (2012) Expanding the medicinally relevant chemical space with compound libraries, *Drug Discov Today* 17:718-726.

Maggiora G M (2006) On outliers and activity cliffs—why QSAR often disappoints. *J Chem Inf Model* 46:1535.

Medina-Franco J L, Martinez-Mayorga K, Bender A, Marin R M, Giulianotti M A, Pinilla C and Houghten R A (2009) Characterization of activity Landscapes using 2D and 3D similarity methods: Consensus activity cliffs. *J Chem Inf Model* 49:477-491.

Medina-Franco J L, Martinez-Mayorga K, Giulianotti M A, Houghten R A and Pinilla C (2008) Visualization of chemical space in drug discovery. *Current Computer-Aided Drug Design* 4:322-333.

Medina-Franco J L, Pinilla C, Appel J R, Giulianotti M A, Santos R G, Yongye A B, Edwards B S, Sklar L A and Houghten R A (2013) Scanning structure-activity relationships in combinatorial data sets: Rapid identification of activity-switches. *J Chem Inf Model*, accepted.

Morley A D, King S, Roberts B, Lever S, Teobald B, Fisher A, Cook T, Parker B, Wenlock M, Phillips C and Grime K (2012) Lead optimisation of pyrazoles as novel FPR1 antagonists. *Bioorg Med Chem Lett* 22:532-536.

Munson P J and Rodbard D (1988) An exact correction to the "Cheng-Prusoff" correction. *J Recept Res* 8:533-546.

Nefzi A, Ong N and Houghten R A (2000) An efficient two-step synthesis of mono-, di- and triureas from resin-bound amides. *Tetrahedron Letters* 41:5441-5446.

Nefzi A, Ostresh J M, Yu Y and Houghten R A (2004) Combinatorial chemistry: libraries from libraries, the art of the diversity-oriented transformation of resin-bound peptides and chiral polyamides to low molecular weight acyclic and heterocyclic compounds. *J Org Chem* 69:3603-3609.

Ostresh J M, Husar G M, Blondelle S E, Dörner B, Weber P A and Houghten R A (1994a) "Libraries from libraries": Chemical transformation of combinatorial libraries to extend the range and repertoire of chemical diversity. *Proc Natl Acad Sci USA* 91:11138-11142.

Ostresh J M, Winkle J H, Hamashin V T and Houghten R A (1994b) Peptide libraries: Determination of relative reaction rates of protected amino acids in competitive couplings. *Biopolymers* 34:1681-1689.

Pinilla C, Appel J R, Blanc P and Houghten R A (1992) Rapid identification of high affinity peptide ligands using positional scanning synthetic peptide combinatorial libraries. *Biotechniques* 13:901-905.

Pinilla C, Appel J R, Borras E and Houghten R A (2003) Advances in the use of synthetic combinatorial chemistry: Mixture-based libraries. *Nat Med* 9:118-122.

Ramirez S, Aiken C T, Andrzejewski B, Sklar L A and Edwards B S (2003) High-throughput flow cytometry: validation in microvolume bioassays. *Cytometry A* 53:55-65.

Reilley K J, Giulianotti M A, Dooley C T, Nefzi A, McLaughlin J P and Houghten R A (2010) Identification of two novel, potent, low-liability antinociceptive compounds from the direct in vivo screening of a large mixture-based combinatorial library. *AAPS J* 12:318-329.

Riviere S, Challet L, Fluegge D, Spehr M and Rodriguez I (2009) Formyl peptide receptor-like proteins are a novel family of vomeronasal chemosensors. *Nature* 459:574-577.

Santos R G, Appel J R, Giulianotti M A, Edwards B S, Sklar L A, Houghten R A and Pinilla C (2013) The mathematics of a successful deconvolution: A quantitative assessment of mixture-based combinatorial libraries screened against two formypeptide receptors. *Molecules* 18:6408-6424.

Santos R G, Giulianotti M A, Dooley C T, Pinilla C, Appel J R and Houghten R A (2011) Use and Implications of the Harmonic Mean Model on Mixtures for Basic Research and Drug Discovery. *ACS Comb Sci* 13:337-344.

Schepetkin I A, Kirpotina L N, Khlebnikov A I and Quinn M T (2007) High-throughput screening for small-molecule activators of neutrophils: identification of novel N-formyl peptide receptor agonists. *Mol Pharmacol* 71:1061-1074.

Schimmer A D, Welsh K, Pinilla C, Wang Z, Krajewska M, Bonneau M-J, Pedersen I M, Kitada S, Scott F L, Bailly-Maitre B, Glinsky G, Scudiero D, Sausville E, Salvesen G, Nefzi A, Ostresh J M, Houghten R A and Reed J C (2004) Small-molecule antagonists of apoptosis suppressor XIAP exhibit broad antitumor activity. *Cancer Cell* 5:25-35.

Singh N, Guha R, Giulianotti M A, Pinilla C, Houghten R A and Medina-Franco J L (2009) Chemoinformatic analysis of combinatorial libraries, drugs, natural products, and molecular libraries small molecule repository. *J Chem Inf Model* 49:1010-1024.

Unitt J, Fagura M, Phillips T, King S, Perry M, Morley A, MacDonald C, Weaver R, Christie J, Barber S, Mohammed R, Paul M, Cook A and Baxter A (2011) Discovery of small molecule human FPR1 receptor antagonists. *Bioorg Med Chem Lett* 21:2991-2997.

Ye R D, Boulay F, Wang J M, Dahlgren C, Gerard C, Parmentier M, Serhan C N and Murphy P M (2009) International Union of Basic and Clinical Pharmacology. LXXIII. Nomenclature for the formyl peptide receptor (FPR) family. *Pharmacol Rev* 61:119-161.

Young S M, Bologa C, Prossnitz E R, Oprea T I, Sklar L A and Edwards B S (2005) High-throughput screening with HyperCyt flow cytometry to detect small molecule formylpeptide receptor ligands. *J Biomol Screen* 10:374-382.

Young S M, Bologa C M, Fara D, Bryant B K, Strouse J J, Arterbum J B, Ye R D, Oprea T I, Prossnitz E R, Sklar L A and Edwards B S (2009) Duplex high-throughput flow cytometry screen identifies two novel formylpeptide receptor family probes. *Cytometry A* 75:253-263.

Zhang J H, Chung T D and Oldenburg K R (1999) A simple statistical parameter for use in evaluation and validation of high throughput screening assays. *J Biomol Screen* 4:67-73.

Zhou C, Zhang S, Nanamori M, Zhang Y, Liu Q, Li N, Sun M, Tian J, Ye P P, Cheng N, Ye R D and Wang M W (2007) Pharmacological characterization of a novel nonpeptide antagonist for formyl peptide receptor-like 1. *Mol Pharmacol* 72:976-983.

Zhou Y, Bian X, Le Y, Gong W, Hu J, Zhang X, Wang L, Iribarren P, Salcedo R, Howard O M, Farrar W and Wang J M (2005) Formylpeptide receptor FPR and the rapid growth of malignant human gliomas. *J Natl Cancer Inst* 97:823-835.

EXAMPLE 3

Rapid Scanning Structure-Activity Relationships in Combinatorial Data Sets: Identification of Activity Switches Structure-activity relationship (SAR) analyses of large data sets usually require the application of computational methods, which enable an organized characterization and rapid identification of activity and selectivity cliffs. Systematic identification and quantification of such cases have been the subject of intense research giving rise to the development of 'activity landscape modeling' that is extensively reviewed elsewhere.[1-3] Most of the activity landscape methods are applied to diverse data sets using fingerprint-based representations calculated from whole molecular structures. Just recently, substructure based representations have been explored for activity landscapes using the concept of matched molecular pair (MMP) which is defined as a pair of compounds that only differs at a single site.[4]

Combinatorial data sets continue to play a central role in lead identification and drug discovery. For example, screening of highly dense mixture-based libraries[5-7] explores uncovered regions of the medicinally-relevant chemical space,[8] increases the potential of identifying activity cliffs and provides a rapid understanding of the SAR associated with novel leads and targets.[8] Furthermore, in vivo testing of mixture-based libraries offers the possibility of identifying 'master key compounds' for multitarget drug discovery (i.e., molecules that may operate on a desired set of 'locks' -targets-to gain access to a desired clinical effect).[9] High-density libraries are suitable for lead identification because they facilitate the detection of small structural modifications that contribute to biological activity and selectivity.

Computational methods have been developed to navigate and visualize the SAR of analogue series or combinatorial data sets. Recent examples include SAR map,[10] SAR matrix,[11] Single R-Group Polymorphisms that identify R-cliffs,[12] and SAR analysis tools recently reviewed by Duffy et al.[13] Although most of these methods are suitable to quickly identify specific R-groups that lead to active, inactive and selective compounds, it is not straightforward to identify pairs of compounds that have opposing—activity outcomes on two or more targets due to specific changes in structure.

Herein, we introduce an approach for the facile visualization and analysis of the SAR of combinatorial data sets. The method is based on systematic pairwise comparisons of the R-groups of all molecular pairs in a data set tested across two biological endpoints. The approach represents an extended application of the Dual-Activity-Difference (DAD) maps that were designed to explore the SAR of diverse sets with activity against two targets.[14,15] In previous applications of the DAD maps, the structural relationships were obtained with similarity calculations computed using fingerprint representations. Since combinatorial data sets have, in general, low-structural diversity, fingerprint-based methods do not always result in easily interpretable SAR. In addition, it has been discussed that the activity landscape models largely depend on the variables utilized to represent chemical structures.[16,17] In order to address these issues, we present an intuitive method to compare systematic changes in the substitutions of combinatorial data sets and finding the associations between those changes and the response in biological activity. We also discuss examples of 'activity switches' and 'selectivity switches',[3] the latter concept defined as a minor structural modification that drastically inverts the selectivity pattern of two compounds. As a case study, we explored the SAR of a series of novel, high affinity formylpeptide receptor (FPR) ligands we reported recently.[18] FPRs are a small group of G protein-coupled receptors that are important in host defense and inflammation. Specifically, the two receptors investigated were FPR1, linked to antibacterial inflammation[19] and malignant glioma cell metastasis,[20] and FPR2, linked to chronic inflammation in systemic amyloidosis, Alzheimer's disease, prion diseases.[21] Using positional scanning deconvolution methods, FPR1 and FPR2 selective ligands with nanomolar binding affinities were identified from mixture-based molecule libraries containing more than 700,000 compounds. The ligands were identified by the screening and deconvolution of TPIMS libraries using a high-throughput screening duplex receptor assay.[18] As noted previously, a number of compounds in this data set showed selective affinities for FPR1 or FPR2 that are the most functionally active reported to date for small molecules in a ligand competition assay format.[18]

Methods

Data Set

We analyzed the SAR of 106 compounds obtained by screening and deconvoluting the pyrrolidine bis-diketopiperazine library in FIG. 1.[18] The library has four diversity positions. Each molecule in the data set has reported binding inhibition constants ($K_i$) that were obtained from competitive ligand displacement assays. The 106 compounds were tested on the basis of deconvoluted results from primary high-throughput screening of mixture libraries in a duplex flow cytometry binding assay. The chemical structures and binding activity ($K_i$) is presented in Table S1 of the Supporting Information. The initial $K_i$ values (in nM) were transformed to $pK_i$ ($-\log_{10} K_i$) values. The activity of compounds with undefined experimental $K_i$ (>10,000 nM) was approximated as 10,000 nM.

Dual-Activity Difference (DAD) Maps

The SAR of data sets tested with two biological endpoints can be characterized using pairwise comparisons portrayed in DAD maps proposed recently.[14,15,22,23] Given a set of N compounds tested with targets I and II, the DAD map depicts $N(N-1)/2$ pairwise potency differences for each possible pair in the data set against both targets. The potency differences for target T for each molecule pair are calculated with the expression:

$$\Delta pK_i(T)_{i,j} = pK_i(T)_i - pK_i(T)_j$$

where $pK_i(T)_i$ and $pK_i(T)_j$ are the activities of the ith and jth molecules (j>i) against the two targets and T=FPR1, FPR2. Noteworthy, $\Delta pK_i$ can have positive or negative values providing information about the directionality of the SAR. Thus, DAD maps are able to differentiate pairs of molecules where the structural change increases the activity for one target but decreases the activity for the other target (see below).[15]

A general form of a DAD map is shown in FIG. 2. Vertical and horizontal lines at $\Delta pK_i \pm t$ define boundaries for low/high potency difference for targets I and II, respectively. Here, we set t=1, one log unit, so that data points were considered with low potency difference if $-1 \leq \Delta pK_i \leq 1$ for each target. The boundaries define zones Z1 through Z5 in FIG. 2. Structural modifications for molecule pairs that fall into zone Z1 (small or a large structural change) have a similar impact on the activity against the two targets (increase or decrease in activity). Therefore, Z1 is associated with similar SAR of the pair of compounds for both targets. In sharp contrast, pairs of compounds that fall into Z2 indicate that the change in activity for the compounds in the pair is opposite for I and II. Thus, the structural changes in the pair of compounds in Z2 are associated with an inverse SAR or switch in activity,[3] increases the activity for one target but decreases the activity for the other target. Thus, activity switches point to structural changes that completely invert the activity pattern. Data points in Z3 and Z4 correspond to pairs of molecules with the same or similar activity for one target (I or II, respectively), but different activity for the other target (II or I, respectively). Data points in Z5 denote a pair of compounds with similar activity (or identical if ΔActivity=0 for both targets) against I and II. In other words, structural changes in the pairs of compounds in Z5 have little or no impact on the activity against the two targets. As previously noted, the classification of data points in an activity-difference map is independent of the structure similarity.[14,15,22,23]

Pairwise Comparison of the R-Group Substitutions

Since dual activity-difference maps are based on pairwise comparisons, it is straightforward to incorporate pairwise structure relationships by distinguishing each molecular pair by the number of substitutions (one to four) around the core or scaffold in FIG. 1. The number of different R-groups for each pair of compounds was determined by comparing the text strings of the chemical names of the substituents in Table S1. This is a simple but powerful method to compare combinatorial data sets. Remarkably, the stereochemistry is taken into account such that substituents with "R" and "S" configuration are easily distinguished by the specific name of the R-group (e.g., "R-propyl" vs. "S-propyl").

Analysis of the SAR is focused on data points in the DAD maps with one or two substitutions since these examples are straightforward to interpret from the experimental point of view. As noted above, distinguishing molecular pairs based on the different number of R-groups around a core scaffold is a substructure-based approach to represent chemical structures. The substructure-based representation of compounds has been proposed in activity landscape studies to enhance interpretability of the SAR[4] and address the 'facts vs. artifacts' issue of activity cliffs.[24]

Fingerprint Representations and Structure Similarity

For comparison, we computed pairwise similarity values using Molecular ACCess System (MACCS) keys (166-bits), graph-based three-point pharmacophores fingerprints (GpiDAPH3), implemented in MOE,[25] and radial fingerprints implemented in Canvas.[26] These three fingerprints were selected because they have conceptually different designs capturing distinctive aspects of chemical structures. For example, MACCS keys used in this work are a pre-defined set of 166 structural keys; GpiDAPH3 fingerprints are graph-based three-point pharmacophores employing any set of three possible atom types (pi system, donor, acceptor); radial fingerprints that are equivalent to the extended connectivity fingerprints (ECFPs), entail growing a set of fragments radially from each heavy atom over a series of iterations.[27,28] We also computed the average similarity of all three measures as a 'consensus' representation discussed previously.[15,29]

Results and Discussion

Overview the Diversity of the Data Set

In order to assess quantitatively the structural similarity and 'high structural density' (low molecular diversity) of the data set, we measured the molecular similarity of the 106 compounds with the pairwise comparisons using the Tanimoto metric and three different fingerprints, namely MACCS, GpiDPH3, and radial fingerprints. The average of all three Tanimoto/fingerprint similarities was computed as described in the Methods section. Table 1 summarizes the distribution of the molecular similarities of the 5565 pairwise comparisons of the 106 compounds in the data set.

Table 1 also summarizes the molecular similarities of the pairwise comparisons of pairs of compounds with one, two, three, and four substitutions (275, 896, 1863, and 2531 pairs of compounds, respectively). The entire data set has, in general, low structural diversity (or high density) as deduced from the median, mean (0.87) and other statistics of the 5565 Tanimoto/MACCS keys similarity values. For comparison, the median MACCS/Tanimoto similarity reported for a general screening collection, and a set of approved drugs is 0.32 and 0.30, respectively.[8] The high density of the data set studied in this work can also be deduced from other fingerprints, e.g., the mean GpiDAPH3/Tanimoto similarity of a set of approved drugs is 0.13.[30] It is also remarkable the different ranges of similarity values obtained with the three fingerprints for the same data set. Such dependence has been extensively discussed in the literature[16, 31] and emphasizes the importance of using more than one fingerprint representation.

Not surprisingly Table 1, FIG. 2EX4 also shows that the 275 pairs of compounds with one substitution have higher similarity than the pairs of compounds with four substitutions. Indeed, as the number of substitutions increases, the molecular similarity decreases. This result is similar for all three fingerprint representations.

To compare the similarities of the potencies of the dataset towards FPR1 and FPR1, the distributions of their absolute pairwise potency differences were analyzed and the results are summarized in Table 2, FIG. 2EX5.

A total of 5,565 pairwise comparisons are shown. Considering all pairwise comparisons, the potency difference for FPR1 is lower than the difference of FPR2, as deduced from the median and all other statistics. This suggests that the activity for FPR2 was, overall, more sensitive to the structural changes of this data set. Table 2 also summarizes the distributions of the potency differences of the pairwise comparisons of pairs of compounds with one, two, three, and four changes in their R-groups. Not surprisingly, for both receptors, the potency difference increases from one to four substitutions. However, the activity for FPR1 was more sensitive than FPR2 to one and two changes in R-groups as clearly shown by the higher absolute potency differences (for example, median values of 0.47 and 0.75 for FPR1 vs. 0.14 and 0.42 for FPR2, respectively). This result suggests that, for this data set, FPR1 is involved in more activity cliffs than FPR2, i.e., it is expected that a large change in activity will be observed for FPR1 ligands due to one or two substitutions in the R-groups. It remains to explore if this observation applies for other pyrrolidine bis-diketopiperazines tested with FPR1 and FPR2. The most dramatic cliffs for each receptor are discussed in the next section with emphasis on those cases where a change in structure switches the activity pattern for FPR1 and FPR2.

Dual Activity-Difference Maps

In order to facilitate the interpretation of the SAR, the analysis is mainly focused on the pairwise comparisons of molecules with one and two substitutions in the R-groups. FIG. 3EX3 shows DAD maps with pairwise potency differences corresponding to pairs of compounds with one (275 data points) and two (896 data points) substitutions; the table beneath the plots shows the number and percentage of data points in each region of the map for compound pairs with single and double substitutions, respectively. Activity changes associated with three and four changes, although easily mined in the DAD maps, are less informative from the SAR interpretation point of view. Noteworthy, the distribution of the data points in all DAD maps discussed here is independent of the structure similarity.

FIGS. 3EX3A and 3EX3B show that the majority of the data points in the corresponding DAD maps are in the center, zone Z5, in particular for the DAD map for single substitutions. These results support the notion that "similar compounds have similar activity" as one or two changes around the core scaffold do not have a large impact on the activity for both receptors, e.g., potency difference less than one log unit. As the number of substitutions increases from one to four, the percentage of pairs of compounds in Z5 decreases.

The DAD maps in FIG. 3EX3 also show data points in the regions Z1-Z4, which are the most informative from an SAR point of view.[14,15] As discussed in the Methods section, compound pairs in these regions point to one or two R-group replacements that change dramatically (more than log unit) the activity difference for one or both receptors. Since the compounds in the data set were derived from the screening results of a mixture based combinatorial library in positional scanning format, it is expected that pairs of compounds with one or two substitutions will have relatively high structural similarity.

The number and percentage of pairs in each zone are summarized in the table below the DAD maps. The higher percentages of data points in Z4 vs. Z3 (FIG. 3EX3) indicate that compared to FPR2, FPR1 is more sensitive to changes in activity than FPR2 from single and double substitutions in the data set. This result is in agreement with the results in Table 2, FIG. 2EX5 discussed above.

Mapping Structure Similarity on DAD Maps Filtered by the Number of Substituents

Although the main focus of this work is scanning the SAR from DAD maps showing pairs of compounds with a discrete number of substituents, for reference, the mean similarity values of the molecule pairs was mapped into the DAD maps. The scale was defined based on the distribution of similarity values for all possible pairs of molecules in the data set. This analysis depicted in a visual manner clearly shows that pairs of compounds with only one different R-group are more similar than compound pairs with two, three and four substitutions (see FIG. 2EX6 and discussion below). This conclusion reflects the quantitative characterization of the molecular similarity analyzed above (Table 1, FIG. 2EX4).

The SAR obtained from zones Z3 and Z4 e.g., single-target activity cliffs, has been broadly discussed in previous applications of DAD maps for other data sets.[14,15] Herein, the discussion of the DAD maps is primarily focused on pairs of compounds in Z1, and more importantly, Z2. It should be recalled that Z1 represents similar SARs, while Z2 indicates inverse SAR. All activity switches (in Z2) are discussed first, followed by representative examples of dual-target activity cliffs with the same directionality of SAR (in Z1).

Activity Switches (Z2) with One Substitution

FIG. 3EX4 shows a DAD map displaying 275 pairs of compounds with one substitution. In this map, the data points are colored by the mean molecular similarity (distributions summarized in Table 1, FIG. 2EX4). As discussed above, most of these points are colored orange-to-red further emphasizing the structural similarity of the pairs of compounds with one substitution (see above). FIG. 3EX4 also shows the chemical structures, biological activity, potency difference and as reference, the structural similarity of the four activity switches in Z2. As discussed below, all compound pairs shown in FIG. 3EX4 except 1754-26/1754-56 are in addition 'selectivity switches'.

For the four pairs in FIG. 3EX4, the change in the R-group (highlighted in magenta) has a large and opposite effect on the activity of FPR1 and FPR2. For example, in the compound pair 1754-43/1754-49 the replacement of an R-propyl with R-2-naphthylmethyl at $R_2$ dramatically increases the activity for FPR2 by more than 2.48 log units (from $K_i$=>10,000 to 33 nM) but it greatly decreases the activity for FPR1 by 1.41 log units (from $K_i$=90 to 2,322 nM). This is also an example of a selectivity switch since 1754-43 is selective for FPR1 whereas 1754-49 is selective for FPR2.

A second notable example is the compound pair 1754-26/1754-56 where the substitution of an S-isopropyl with S-butyl at $R_1$ increases the activity for FPR1 by 1.36 log units but decreases the activity for FPR2 in 1.28 log units. Notably, as pointed out previously, 1754-26 was the only compound in the data set with a $K_i$ value less than 100 nM for both receptors.[18] The compound pair 1754-26/1754-56, however, is not a selectivity switch because 1754-26 is nearly equipotent with both receptors.

The mean structural similarity of the activity switches in FIG. 3EX4 is high, relative to the mean similarity of the entire data set (for all 5565 pairs of compounds, Table 1, FIG. 2EX4). For example, all four molecule pairs have mean similarity equal or greater than 0.73, which is higher than the U95 of the mean similarity for the whole data set, 0.61. These results indicate that the switches discussed in this figure would have been identified following a fingerprint similarity based approach (because of its 'high' fingerprint-based structural similarity). However, as discussed in the literature, using a substructure-based method to classify molecular structures is more intuitive and easy to interpret than using fingerprint representations in activity landscape studies.[4]

Activity Switches (Z2) with Two Substitutions

FIG. 3EX5 presents a DAD map showing 896 pairs of compounds with two substitutions. Data points are further distinguished by the mean molecular similarity. Comparison of this figure in the color pattern of the DAD map in FIG. 3EX4 clearly shows the overall lower structural similarity of the pairs of compounds with two substitutions (see also Table 1, FIG. 2EX4). FIG. 3EX5 also presents the chemical structures of three representative activity switches in Z2 (selected from 49 total) along with the biological activity, potency difference and structural similarity. The changes in the R-groups are highlighted in magenta. We choose these examples because they have one potent compound ($K_i \leq 90$ nM) for FPR1 or FPR2 in the pair.

For the three examples in FIG. 3EX5, the two changes in the R-groups have a large and opposite effect on the activity for FPR1 and FPR2. Notably, in the molecule pair 1754-31/1754-43, the replacement of an S-isopropyl to an S-propyl in $R_1$, and the substitution of an R-2-naphthylmethyl to R-propyl in $R_2$ increases the activity for FPR1 by more than two log units (from $K_i$=>10,000 to 90 nM) but it decreases dramatically the activity for FPR2 by four log units (from $K_i$=1 to >10,000 nM). Two other remarkable examples of activity switches with two R-group replacements are given by the pairs of compounds 1754-20/1754-56 and 1754-31/1858-482. The three activity switches in FIG. 3EX5 are also selectivity switches, since the corresponding replacement in the R-groups has not only an opposite effect on the activity of the two receptors, but also on the selectivity.

The molecular similarity of the three compound pairs in FIG. 3EX5 (e.g., mean structure similarity equal or greater than 0.65) is still higher than the U95 mean similarity (0.61) of all pairs of compounds in the data set. Thus, they would be considered structurally similar. Although these examples would have been retrieved from a fingerprint similarity based approach, it is clear that these pairs of compounds represent borderline cases in activity landscape studies based on fingerprint-based molecular similarity.

The previous examples illustrate that the SAR of pairs of compounds with two substitutions can be rapidly analyzed in a systematic manner in DAD maps. However, the interpretation of the SAR for compounds with two (or more) substitutions is more difficult than pairs of compounds with only one substitution. In the following subsections, the discussion is focused on representative examples of dual- and single-target activity cliffs with one R-group replacement. These cases can be regarded as R-cliffs.[12]

Dual-Target Activity Cliffs (Z1)

FIG. 3EX6 shows a DAD map with pairs of compounds with one substitution. The seven Z1 data points are labeled. As clearly shown in the figure, the change in the R-group for all seven pairs simultaneously increases (or decreases) the activity for both targets by more than a log unit. The pair of compounds 1754-44 and 1858-483 illustrate that the replacement of a 2-biphenyl-4-yl-ethyl to a 4-methyl-1-cyclohexyl-methyl in $R_4$ decreases the activity for FPR1 and FPR2. Similar analysis can be performed for the other six pairs of compounds.

Single-Target Activity Cliffs

FIG. 3EX7 shows the three single-target activity cliffs with a very large potency difference, i.e., more than three log units. These examples can be regarded as "deep activity cliffs".[29] It is clear from the figure that the corresponding R-group modification greatly changes the activity for only one target, either FPR1 (pairs 1754-44/1754-50; 1754-56/1858-480) or FPR2 (1754-6/1754-31). However, the replacement of the R-group does not have a major impact (<1 log unit) on the activity of the other target.

Interestingly, the chemical structures and $K_i$ values of compounds 1754-43 and 1858-483 in FIG. 6 exemplify a single-target activity cliff for FPR1 (the pair 1754-43/1858-483 is not labeled in the DAD map in FIG. 6 that illustrates dual target cliffs). The only difference in the chemical structure of this pair of compounds is the methyl group in the $R_4$ substituent highlighted in blue, i.e., cyclohexyl-methyl vs. 4-methyl-1-cyclohexyl-methyl. This subtle modification changes the activity for FPR1 from $K_i$=90 nM (1754-43) to $K_i$>10,000 nM (1858-483). However, this modification has no impact on the activity of FPR2.

SAS Maps

DAD maps are highly related to the Structure-Activity Similarity (SAS) maps that are two-dimensional plots representing the relationship between the potency difference for one target (typically plotted on the Y-axis) and the structural similarity (usually plotted on the X-axis).[3] It is possible to generate SAS maps for FPR1 and FPR2 and further distinguish the data points based on the number of R-group changes (FIGS. 2EX7/1EX2 and 2EX8 in the Supporting Information). Although it is straightforward to identify single-target activity cliffs from these maps, the directionality of the SAR is lost; therefore, it is impossible to identify selectivity switches and dual-target cliffs with similar SAR.

Conclusions

We report an intuitive substructure-based approach for the systematic and rapid scanning of the SAR in combinatorial data sets using the concept of activity landscape modeling. The general method herein introduced enables the quick and methodological identification on large changes in biological activity associated with one, two (or more) replacements in the R-groups of a common scaffold. The approach captures the substructure relationships of all possible pairs in the data set, and it is reminiscent of the MMP concept. However, while the MMP and MMP-Cliffs consider structural changes at a single R-group, the current approach considers structural changes at one, two or more groups. Of course, changes at one or two groups are the ones that are easier to interpret for a medicinal chemist. The substructure relationships can be readily mapped and visualized in DAD maps. DAD maps are based on pairwise comparisons of potency differences making it straightforward to represent changes in the R-groups and to systematically explore single and dual-target activity R-cliffs. In particular, DAD maps enable the rapid identification of all 'activity switches', defined as pairs of compounds where a small change in the structure (e.g., replacement of one or two R-groups), completely invert the biological response for two targets, namely, increases the activity for one target but decreases the activity for the second target. Several 'activity switches' identified in this work were also 'selective switches' defined as structural changes that completely invert the selectivity pattern of similar compounds against two biological endpoints. Of note, the number of data points analyzed in the DAD maps are selected solely based on the number of R-group substitutions of the core scaffold. This approach is in sharp contrast with previous applications of the DAD maps where data points are selected based on the fingerprint-similarity values. To illustrate the rapid detection of activity switches in combinatorial data sets using DAD maps we discuss the activity switches, single- and dual-target activity cliffs of a novel and relevant set of 106 pyrrolidine bis-diketopiperazines tested with two formylpeptide receptors.[18] This data set represents one example of several combinatorial data sets obtained from positional scanning deconvolution methods of mixture-base libraries.[5,7]

References for Example 3

(1) Stumpfe, D.; Bajorath, J., Exploring Activity Cliffs in Medicinal Chemistry. *Journal of Medicinal Chemistry* 2012, 55, 2932-2942.
(2) Bajorath, J., Modeling of activity landscapes for drug discovery. *Expert. Opin. Drug Discov.* 2012, 7, 463-473.
(3) Medina-Franco, J. L., Scanning Structure-Activity Relationships with SAS and Related Maps: From Consensus Activity Cliffs to Selectivity Switches, *J. Chem. Inf. Model.* 2012, 52, 2485-2493.
(4) Hu, X.; Hu, Y.; Vogt, M.; Stumpfe, D.; Bajorath, J., MMP-Cliffs: Systematic Identification of Activity Cliffs on the Basis of Matched Molecular Pairs. *J. Chem. Inf. Model,* 2012, 52, 1138-1145.
(5) Houghten, R. A.; Pinilla, C.; Appel, J. R.; Blondelle, S. E.; Dooley, C. T.; Eichler, J.; Nefzi, A.; Ostresh, J. M., Mixture-Based Synthetic Combinatorial Libraries. *J. Med. Chem,* 1999, 42, 3743-3778.
(6) Pinilla, C.; Appel, J. R.; Borras, E.; Houghten, R. A., Advances in the use of synthetic combinatorial chemistry: Mixture-based libraries. *Nat. Med.* 2003, 9, 118-122.
(7) Houghten, R. A.; Pinilla, C.; Giulianotti, M. A.; Appel, J. R.; Dooley, C. T.; Nefzi, A.; Ostresh, J. M.; Yu, Y. P.; Maggiora, G. M.; Medina-Franco, J. L.; Brunner, D.; Schneider, J., Strategies for the use of mixture-based synthetic combinatorial libraries: Scaffold ranking, direct testing, in vivo, and enhanced deconvolution by computational methods. *J. Comb. Chem.* 2008, 10, 3-19.
(8) López-Vallejo, F.; Giulianotti, M. A.; Houghten, R. A.; Medina-Franco, J. L., Expanding the medicinally relevant chemical space with compound libraries. *Drug Discovery Today* 2012, 17, 718-726.
(9) Medina-Franco, J. L.; Giulianotti, M. A.; Welmaker, G. S.; Houghten, R. A., Shifting from the single to the multitarget paradigm in drug discovery. *Drug Discovery Today* 2013, in press. DOI: 10.1016/j.drudis.2013.01.008,
(10) Kolpak, J.; Connolly, P. J.; Lobanov, V. S.; Agrafiotis, D. K., Enhanced SAR Maps: Expanding the Data Rendering Capabilities of a Popular Medicinal Chemistry Tool. *J. Chem. Inf. Model.* 2009, 49, 2221-2230.
(11) Wassermann, A. M.; Haebel, P.; Weskamp, N.; Bajorath, J., SAR Matrices: Automated Extraction of Information-Rich SAR Tables from Large Compound Data Sets. *J. Chem. Inf. Model.* 2012, 52, 1769-1776.
(12) Agrafiotis, D. K.; Wiener, J. J. M.; Skalkin, A.; Kolpak, J., Single R-Group Polymorphisms (SRPs) and R-Cliffs: An Intuitive Framework for Analyzing and Visualizing Activity Cliffs in a Single Analog Series. *J. Chem. Inf. Model.* 2011, 51, 1122-1131.
(13) Duffy, B. C.; Zhu, L.; Decornez, H.; Kitchen, D. B., Early phase drug discovery: Cheminformatics and computational techniques in identifying lead series. *Bioorg. Med. Chem.* 2012, 20, 5324-5342.
(14) Pérez-Villanueva, J.; Santos, R.; Hernández-Campos, A.; Giulianotti, M. A.; Castillo, R.; Medina-Franco, J. L., Structure-activity relationships of benzimidazole derivatives as antiparasitic agents: Dual activity-difference (DAD) maps. *Med. Chem. Comm.* 2011, 2, 44-49.
(15) Medina-Franco, J. L.; Yongye, A. B.; Pérez-Villanueva, J.; Houghten, R. A.; Martínez-Mayorga, K., Multitarget Structure-Activity Relationships Characterized by Activity-Difference Maps and Consensus Similarity Measure, *J. Chem. Inf. Model.* 2011, 51, 2427-2439.
(16) Medina-Franco, J. L.; Martínez-Mayorga, K.; Bender, A.; Marín, R. M.; Giulianotti, M. A.; Pinilla, C.; Houghten, R. A., Characterization of Activity Landscapes Using 2D and 3D Similarity Methods: Consensus Activity Cliffs. *J. Chem. Inf. Model.* 2009, 49, 477-491.
(17) Yongye, A.; Byler, K.; Santos, R.; Martínez-Mayorga, K.; Maggiora, G. M.; Medina-Franco, J. L., Consensus Models of Activity Landscapes with Multiple Chemical, Conformer and Property Representations. *J. Chem. Inf. Model.* 2011, 51, 1259-1270.
(18) Pinilla, C.; Edwards, B. S.; Appel, J. R.; Yates-Gibbins, T.; Giulianotti, M. A.; Medina-Franco, J. L.; Young, S. M.; Santos, R. G.; Sklar, L. A.; Houghten, R. A., Selective agonists and antagonists of formylpeptide receptors: duplex flow cytometry and mixture-based positional scanning libraries. submitted.
(19) Le, Y.; Murphy, P. M.; Wang, J. M., Formyl-peptide receptors revisited. *Trends Immunol.* 2002, 23, 541-548.
(20) Zhou, Y.; Bian, X.; Le, Y.; Gong, W.; Hu, J.; Zhang, X.; Wang, L.; Iribarren, P.; Salcedo, R.; Howard, O. M. Z.; Farrar, W.; Wang, J. M., Formylpeptide Receptor FPR and the Rapid Growth of Malignant Human Gliomas. *J. Natl. Cancer Inst.* 2005, 97, 823-835.
(21) Le, Y.; Yazawa, H.; Gong, W.; Yu, Z.; Ferrans, V. J.; Murphy, P. M.; Wang, J. M., Cutting Edge: The Neurotoxic Prion Peptide Fragment PrP106-126 Is a Chemotactic Agonist for the G Protein-Coupled Receptor Formyl Peptide Receptor-Like 1. *J. Immunol.* 2001, 166, 1448-1451.
(22) Pérez-Villanueva, J.; Medina-Franco, J. L.; Méndez-Lucio, O.; Yoo, J.; Soria-Arteche, O.; Izquierdo, T.; Lozada, M. C.; Castillo, R., CASE Plots for the Chemotype-Based Activity and Selectivity Analysis: A CASE Study of Cyclooxygenase Inhibitors. *Chem. Biol. Drug Des.* 2012, 80, 752-762,
(23) Méndez-Lucio, O.; Pérez-Villanueva, J.; Castillo, R.; Medina-Franco, J. L., Activity Landscape Modeling of PPAR ligands with Dual-Activity Difference Maps. *Bioorg. Med. Chem.* 2012, 20, 3523-3532.

(24) Medina-Franco, J. L., Activity Cliffs: Facts or Artifacts?, submitted,

(25) MOE Molecular Operating Environment (MOE), version 2011.10, Chemical Computing Group Inc., Montreal, Quebec, Canada. Available at: http://www.chemcomp.com.

(26) Canvas Canvas, version 1.5; Schrödinger, LLC, New York, N.Y., 2012.

(27) Rogers, D.; Hahn, M., Extended-Connectivity Fingerprints. *J. Chem. Inf. Model.* 2010, 50, 742-754.

(28) Sastry, M.; Lowrie, J. F.; Dixon, S. L.; Sherman, W., Large-Scale Systematic Analysis of 2D Fingerprint Methods and Parameters to Improve Virtual Screening Enrichments. *J. Chem. Inf. Model.* 2010, 50, 771-784.

(29) Pérez-Villanueva, J.; Santos, R.; Hernández-Campos, A.; Giulianotti, M. A.; Castillo, R.; Medina-Franco, J. L., Towards a systematic characterization of the antiprotozoal activity landscape of benzimidazole derivatives. *Bioorg. Med. Chem.* 2010, 18, 7380-7391.

(30) Singh, N.; Guha, R.; Giulianotti, M. A.; Pinilla, C.; Houghten, R. A.; Medina-Franco, J. L., Chemoinformatic Analysis of Combinatorial Libraries, Drugs, Natural Products, and Molecular Libraries Small Molecule Repository. *J. Chem. Inf. Model,* 2009, 49, 1010-1024.

(31) Bender, A., How similar are those molecules after all? Use two descriptors and you will have three different answers. *Expert. Opin. Drug Discov.* 2010, 5, 1141-1151.

EXAMPLE 4

The Mathematics of a Successful Deconvolution: A Quantitative Assessment of Mixture-Based Combinatorial Libraries Screened Against Two Formylpeptide Receptors In an effort to further increase efficiency and utility as this collection of libraries increases, we previously developed a strategy termed scaffold ranking for the rapid identification and ranking of active library scaffolds [3].

FIG. 4EX1 shows a simplified illustration of the screening process using mixture-based combinatorial libraries. In a scaffold ranking library, all compounds in the library are simultaneously present as a mixture in a single sample; FIG. 4EX1A shows two 27-compound scaffold ranking library samples, with the colors red, blue and yellow representing three choices of functionality at each of three positions.

In general, scaffold ranking library samples can result from mixing the cleaved products of the complete positional scanning library or may be synthesized directly as a single mixture. The objective of using scaffold ranking libraries is to prioritize library scaffolds for future analysis, including positional scanning; as show in FIG. 4EX1A-B, the scaffold which includes the black active compound (represented by a triangle) is chosen for positional scanning because its scaffold ranking mixture is relatively more active when compared to the other scaffold shown (represented by a circle). Only a single positional scanning library is then tested (FIG. 4EX1B) and deconvoluted (by picking the most active mixtures at each position) in order to find the active compound (FIG. 4EX1C). This process can be advantageous in low-throughput assays that would make numerous positional scanning library screenings impractical. The relative efficacy of the scaffold ranking approach provides clear support for its use in low-throughput assays, or costly assays including in vivo screening.

The format in which scaffold ranking or positional scanning libraries are used in a particular lead discovery effort will depend on the resources and throughput of the assay. The flexibility of these two screening formats of mixture-based libraries represents a clear advantage for the rapid identification of active lead compounds.

Because screening all positional scanning libraries may not be practical in all assays, determining the information both present and absent in a scaffold ranking, relative to positional scanning, is vital for proper usage of the scaffold ranking approach. Herein, we present such a study based on the screening of mixture-based libraries against the formylpeptide receptor (FPR1) and formylpeptide-like1 receptor (FPR2) targets, two receptors that have been implicated in both cancer [12] and inflammatory responses [13].

Thirty-two positional scanning libraries (FIG. 4EX2 and Table S1, FIG. 2EX9) were tested in their entirety (for a total of 4,304 samples), along with the corresponding 32 scaffold ranking samples. Detailed methodologies and analyses of structures and activities of the individual compounds discovered in this campaign will be presented elsewhere [14, 15]. In this study, we present and demonstrate quantitative tools that analyze and use the information present in a positional scanning library screening most important to increasing the likelihood of a successful deconvolution. We also focus on comparing and contrasting the scaffold ranking and positional scanning screening approaches from a mathematical modeling perspective.

The results presented here demonstrate that the scaffold ranking library samples lead to effective selection of active positional scanning libraries; consequently, determining the relative activities of the libraries as the first step of a screening campaign does not require the use of the complete collection of positional scanning libraries. This strategy greatly reduces the time and resources required by testing a fraction of the samples with equivalent accuracy. However, it will be also shown that use of the complete collection of positional scanning libraries provides screening data that offers important information, beyond activity alone, which increases the likelihood of the successful deconvolution of a library.

Considering the inherent inaccuracy of single-dose $IC_{50}$ extrapolations one would not expect perfect correspondences between scaffold ranking $xIC_{50}$s and the harmonic mean of a position's $xIC_{50}$s. In general, however, scaffold ranking activities corresponded well to those obtained by harmonic meaning each position; only three comparisons resulted in even a four-fold disparity against the average harmonic mean of its positional scanning library, and 41 of the 64 total comparisons had under a two-fold disparity. Many differences were the result of the scaffold ranking $xIC_{50}$ being 1,000, and the positional scanning harmonic means being lower; this is unsurprising, since by imposing a cap on $xIC_{50}$ values, errors would necessarily be one-sided. The three largest deviations, however, were all overestimates: Libraries 5, 19, and 24 against FPR1. Library 19 had the highest error (over five-fold more active than the average harmonic mean of its positional scanning library) but was the most active library against FPR1 in either case. Libraries 5 and 24, while showing above-average activity in their positional scanning samples, were not actually the second- and third-most active libraries against FPR1; library 32, whose scaffold ranking $xIC_{50}$ and positional scanning harmonic means corresponded quite well, was actually the second-most active overall. It should be noted, however, libraries 5 and 24 do not exhibit substantially less active positional scanning harmonic means than library 32.

Analysis of Positional Scanning Profiles

As shown above, scaffold ranking is equally capable of gauging the overall activity of a given library. However, when the assay throughput rate allows, there is a wealth of additional information present in a full screening of all positional scanning libraries that can aid in choosing the most promising libraries to deconvolute. One of the most important aspects of a positional scanning activity profile is the level of activity differentiation of samples at each position. Given the same overall library activity, a positional scanning activity profile that shows few mixtures at each position that are much more active than the rest is likelier to have compounds that are more active than one with little differentiation. To see why this is the case, consider a library with a scaffold ranking sample IC5o of 100 ìM containing inactive compounds with IC5os of 1,000 ìM and an unknown percentage of active compounds of fixed unknown activity. Under the assumptions of the Harmonic Mean model, such a library could theoretically have a composition of compounds ranging from 100% of compounds with IC5os of 100 ìM each, to 0.01% of compounds with an IC5o of 11 nM each, to even smaller percentages of even more active compounds. If, in such a library, a position contained only one mixture that exhibited activity higher than that of an inactive compound (therefore being a well-differentiated profile), then that mixture would need to have a very high relative activity (so that the harmonic mean of that position would come out to 100 ìM), and thus the vast majority of the active compounds would be mathematically required to be within that mixture. Since that mixture represents only a fraction of the total library, this in turn puts an upper bound on the percentage of active compounds that could be in the library; as presented above, the lower the percentage of active compounds, the greater the required activity of each active compound. In contrast, if a position contained mixtures all with approximately the same activity, then these mixtures' IC5os must be approximately 100 ìM each in order for their harmonic mean to be 100 ìM. Thus each mixture would be required to have approximately the same number of active compounds, and so no upper bound can be placed on the overall percentage of active compounds.

In an effort to quantify the activity profile of a positional scanning library position that models activity differentiation, the following procedure was developed. For a given position with n functional groups, let $\{x_k\}_{k=1}^n$ be the rank-ordered activities of the mixtures in that position, so that $x_1$ is the most active mixture's activity, $x_2$ is the second-most active mixture's activity, etc. In this study, percentage inhibition values were used for the activities; since we are attempting to compare the differentiation of positional scanning profiles within a single study, absolute scaling issues are irrelevant so long as they are consistent, and so long as higher numbers correspond to greater activity. Next, the maximum drop in activity $$m = \max_{k=1,\ldots,n-1} (x_k - x_{k+1}) \tag{3}$$

was calculated. This represents the maximum sequential activity difference within the position; clearly, the more difference between active and inactive mixtures, the greater m. The value of k for which the largest drop occurs, K, is calculated as well:

$$K = \underset{k=1,\ldots,n-1}{\mathrm{argmax}} (x_k - x_{k+1}). \tag{4}$$

For an ideally differentiated positional scanning library activity profile, then, one would see high activity differences between active and inactive mixtures (i.e., a high value of m) in a relatively small number of mixtures (i.e., a low value of K). To this end, the index of differentiation of a positional scanning position's profile is defined as $$I_{DIFF} \equiv \frac{m}{2^{K-1}}, \tag{5}$$

The values of $I_{DIFF}$ for each position of each of the 32 libraries in this study are shown in Table 2, FIG. 4EX5. Selected profiles illustrating high and low differentiation are shown in FIG. 4EX4. Note that $I_{DIFF}$ can vary greatly from position to position in a given library; this is unsurprising, since specific functionalities at certain positions will inevitably be more important to the activity potential of a compound than others. Library 32 exhibited by far the highest average index of differentiation for FPR1, having the highest single position $I_{DIFF}$, and two remaining positions ranking $6^{th}$ and $11^{th}$. Libraries 20, 21, and 24 showed relatively high differentiation in some positions, but not all, and had the next highest average $I_{DIFF}$. For FPR2, library 19 had the highest average $I_{DIFF}$, followed closely by libraries 20 and 29; all three exhibited high-ranking differentiation in two of their positions.

As reasoned above, high differentiation is very important for potentiating the discovery of highly active compounds in a positional scanning screening profile. Such differentiation in the absence of overall activity, however, may only result in varying degrees of inactive compounds. Therefore, the overall potentiation index of deconvolutability of a library is better quantified as $$I_{DECON} \equiv \frac{\text{Average } I_{DIFF} \text{ Over All Positions}}{\text{Average Harmonic Mean of } xIC50s \text{ Over All Positions}}. \tag{6}$$

The values of $I_{DECON}$ for each library are in Table 2, FIG. 4EX5. As is evident, each receptor has one standout library: library 32 for FPR1, because of high relative activity and very high relative differentiation, and library 19 for FPR2 (which had the second highest score in FPR1 as well), because of very high relative activity and high relative differentiation. Indeed, these libraries were the two chosen in this study for deconvolution, and both proved to lead to the identification of highly active individual compounds with nanomolar $K_i$ values [14].

Selectivity in Scaffold Ranking and Positional Scanning

In the event that selectivity is a desirable endpoint in a study, as it was in this study, additional important lessons can be learned about the relative utility of screening scaffold ranking libraries versus complete positional scanning libraries. As has already been noted, library 19 showed the highest level of overall scaffold ranking activity in both receptors. Library 32, in contrast, only showed substantial scaffold ranking activity against the FPR1 target. Using this information to infer that library 19 could not include selective compounds, however, would not be an appropriate use of the activity of the scaffold ranking samples. The absence of activity in FPR2 for library 32 did indeed imply, both in its positional scanning profile and its eventual deconvolution, an absence of FPR2-active individual compounds. The reverse, however, proved not to be true, as is evident from a closer inspection of library 19's positional scanning activity profile (FIG. 4EX6). Although library 19 exhibits overall high activity against both targets, the mixtures at each position that exhibit that activity vary greatly; FPR2 shows greater differentiation in the first two positions (as evidenced by its higher index of differentiation as described above), and the mixtures of maximum activity do not correspond to those of FPR1. These patterns persisted when individual compounds were tested. Thus, positional scanning libraries should be selected and screened even if the scaffold ranking screening does not show the desired selectivity. Positional scanning libraries offer a window into the possibility of additional selectivity of individual compounds that would not be evident in the analysis of the scaffold ranking library's activity alone.

Conclusions

In the past, scaffold ranking has been used as a first step for determining which library will be tested using positional scanning. With the side-by-side data presented in this study, we have shown for the first time that scaffold ranking is indeed sufficient for accurately demonstrating the overall activity of a library, with each library presenting essentially the same activity levels in its scaffold ranking format as in its full positional scanning format. However, we have also demonstrated that, when feasible, complete screening of all positional scanning libraries allows for additional analyses of the differentiation and selectivity that can drastically increase the likelihood of a successful deconvolution.

If only the scaffold ranking samples had been tested, library 19 surely would have been chosen, based on the basis of its activity, to screen the complete positional scanning library; as we have shown in this study, to exclude a library on the grounds of selectivity using only scaffold ranking information is a mistake. The potential of identifying selective compounds is only revealed from analysis of its positional scanning profile. As will be presented in a complementary study, 106 individual compounds were synthesized and tested from library 19 [14]. Nineteen compounds had Ki values ≤100 nM for FPR1, of which 15 were FPR1 selective (Ki values for FPR2 are more than 100-fold greater); 23 compounds had Ki values ≤100 nM for FPR2, of which 12 were selective for FPR2. Furthermore, Library 32, with less activity exhibited in the scaffold ranking than other libraries, may not have been explored at all, had its impressively differentiated profile not been determined through screening its positional scanning library. Deconvolution of Library 32 resulted in the synthesis of only 8 individual compounds, of which 4 had Ki values ≤20 nM in FPR1 and were highly selective. Additional libraries (library 24 for FPR1, and libraries 20 and 29 for FPR2) that have not yet been deconvoluted show about the same indices of deconvolutability as the successfully deconvoluted library 19 for FPR1; these are clearly a possible direction for future research.

By having the scaffold ranking data in tandem with the positional scanning data, one is better able to see the strengths and weaknesses of each approach, and use this knowledge to further increase the effectiveness of already-effective mixture-based combinatorial library screening.

References for Example 4

1. Houghten, R. A.; Pinilla, C.; Appel, J. R.; Blondelle, S. E.; Dooley, C. T.; Eichler, J.; Nefzi, A.; Ostresh, J. M. Mixture-based synthetic combinatorial libraries. *J. Med. Chem.* 1999, 42, 3743-3778.
2. Pinilla, C.; Appel, J. R.; Borras, E.; Houghten, R. A. Advances in the use of synthetic combinatorial chemistry: Mixture-based libraries. *Nat. Med.* 2003, 9, 118-122.
3. Houghten, R. A.; Pinilla, C.; Giulianotti, M. A.; Appel, J. R.; Dooley, C. T.; Nefzi, A.; Ostresh, J. M.; Yu, Y.; Maggiora, G. M.; Medina-Franco, J. L.; Brunner, D.; Schneider, J. Strategies for the use of mixture-based synthetic combinatorial libraries: scaffold ranking, direct testing in vivo, and enhanced deconvolution by computational methods. *J. Comb. Chem.* 2008, 10, 3-19.
4. Pinilla, C.; Appel, J. R.; Blanc, P.; Houghten, R. A. Rapid identification of high affinity peptide ligands using positional scanning synthetic peptide combinatorial libraries. *Biotechniques* 1992, 13, 901-905.
5. Dooley, C. T.; Houghten, R. A. The use of positional scanning synthetic peptide combinatorial libraries for the rapid determination of opioid receptor ligands. *Life Sci.* 1993, 52, 1509-1517.
6. Santos, R. G.; Giulianotti, M. A.; Dooley, C. T.; Pinilla, C.; Appel, J. R.; Houghten, R. A. Use and implications of the harmonic mean model on mixtures for basic research and drug discovery. *ACS Comb. Sci.* 2011, 13, 337-344.
7. Giulianotti, M. A.; Debevec, G.; Santos, R. G.; Maida, L. E.; Chen, W.; Ou, L.; Yu, Y.; Dooley, C. T.; Houghten, R. A. A novel method for the determination of isokinetic ratios and its application in the synthesis of two new positional scanning libraries. *ACS Comb, Sci.* 2012, 14, 503-512.
8. Ranjit, D. K.; Rideout, M. C.; Nefzi, A.; Ostresh, J. M.; Pinilla, C.; Segall, A. M. Small molecule functional analogs of peptides that inhibit lambda site-specific recombination and bind Holliday junctions. *Bioorg. Med. Chem. Lett.* 2010, 20, 4531-4534.
9. Rideout, M. C.; Boldt, J. L.; Vahi-Ferguson, G.; Salamon, P.; Nefzi, A.; Ostresh, J. M.; Giulianotti, M.; Pinilla, C.; Segall, A. M. Potent antimicrobial small molecules screened as inhibitors of tyrosine recombinases and Holliday junction-resolving enzymes. *Mol. Divers.* 2011, 15, 989-1005.
10. Reilley, K. J.; Giulianotti, M.; Dooley, C. T.; Nefzi, A.; McLaughlin, J. P.; Houghten, R. A. Identification of two novel, potent, low-liability antinociceptive compounds from the direct in vivo screening of a large mixture-based combinatorial library. *AAPS J.* 2010, 12, 318-329.
11. Minond, D.; Cudic, M.; Bionda, N.; Giulianotti, M.; Maida, L.; Houghten, R. A.; Fields, G. B. Discovery of novel inhibitors of a disintegrin and metalloprotease 17 (ADAM17) using glycosylated and non-glycosylated substrates. *J. Biol. Chem.* 2012, 287, 36473-36487.
12. Zhou, Y.; Bian, X.; Le, Y.; Gong, W.; Hu, J.; Zhang, X.; Wang, L.; Iribarren, P.; Salcedo, R.; Howard, O. M.; Farrar, W.; Wang, J. M. Formylpeptide receptor FPR and the rapid growth of malignant human gliomas. *J. Natl. Cancer. Inst.* 2005, 97, 823-835.
13. Le, Y.; Yazawa, H.; Gong, W.; Yu, Z.; Ferrans, V. J.; Murphy, P. M.; Wang, J. M. The neurotoxic prion peptide fragment PrP (106-126) is a chemotactic agonist for the G protein-coupled receptor formyl peptide receptor-like 1. *J. Immunol.* 2001, 166, 1448-1451.
14. Pinilla, C.; Edwards, B. S.; Appel, J. R.; Yates-Gibbins, T.; Giulianotti, M.; Medina-Franco, J. L.; Young, S. M.; Santos, R. G.; Sklar, L. A.; Houghten, R. A. Selective agonist and antagonist of formylpeptide receptors:duplex flow cytometry and mixture-based positional scanning libraries. *Mol. Pharmacol.* 2013, submitted.

15. Medina-Franco, J. L.; Pinilla, C.; Appel, J. R.; Giulianotti, M.; Santos, R. G.; Yongye, A. B.; Edwards, B. S.; Sklar, L. A.; Houghten, R. A. Scanning structure-activity relantionships in combiatorial data sets: Rapid identification of activity-switches. *J. Chemical Information and Modeling* 2013, submitted.

What is claimed is:

1. A method of modulating formyl peptide receptor-1 (FPR1) or formyl peptide receptor-2 FPR2 in a subject in need thereof, the method comprising administering to the subject an effective amount of a compound as set forth in FIG. 1EX3, FIG. 1EX4 or FIG. 2EX5 herein, or a pharmaceutically acceptable salt or enantiomer thereof.

2. The method of claim 1, wherein the subject suffers from amyloidosis, Alzheimer's disease, a prion disease, HIV, a cancer or an inflammatory disorder.

3. The method of claim 2, wherein the subject suffers from HIV and the compound is optionally administered in combination with an additional anti-HIV agent.

4. The method of claim 2, wherein the subject suffers from a cancer and the compound is optionally administered with an additional anti-cancer agent.

5. The method according to claim 1 wherein said compound is

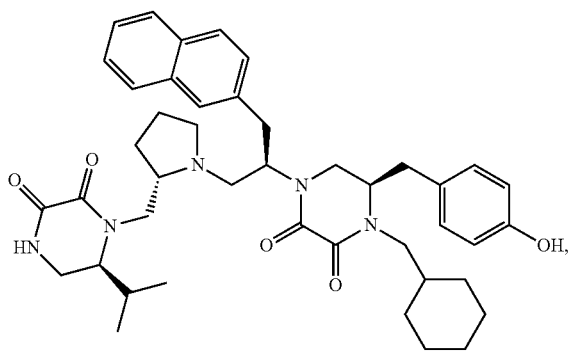 [SMILES: CC(C)[C@H]1CNC(=O)C(=O)N1C[C@@H]1CCCN1C[C@@H](Cc1ccc2ccccc2c1)N1C[C@@H](Cc2ccc(O)cc2)N(CC2CCCCC2)C(=O)C1=O]

a compound of FIG. 1EX4, or a pharmaceutically acceptable salt or stereoisomer thereof.

6. The method according to claim 1 wherein said compound is

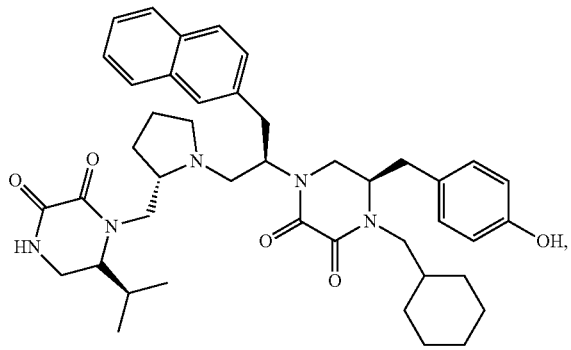

-continued

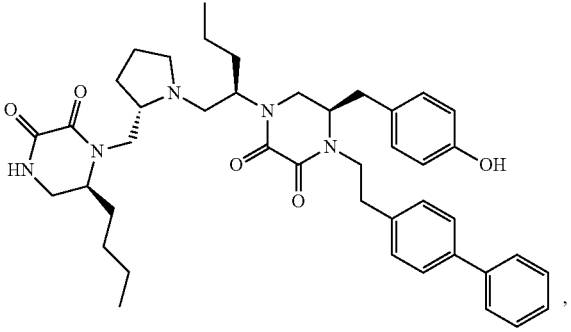

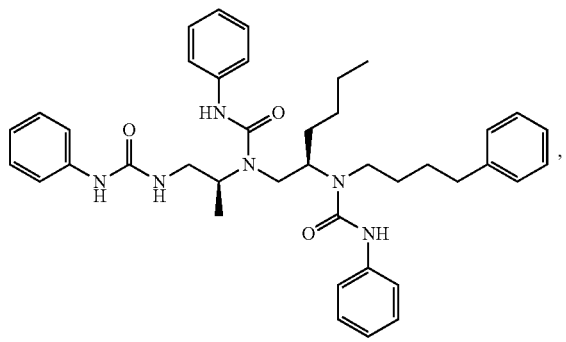

or a pharmaceutically acceptable salt thereof.

7. The method according to claim 2 wherein said subject suffers from cancer.

8. The method according to claim 7 wherein said cancer is selected from the group consisting of squamous-cell carcinomas, adenocarcinomas, hepatocellular carcinomas, renal cell carcinomas, leukemias; lymphomas, melanomas; myeloproliferative diseases; sarcomas, tumors of the central nervous system and germ-line tumors.

9. The method according to claim 7 wherein said cancer is selected from the group consisting of bladder cancer, bowel cancer, breast cancer, cervical cancer, colon cancer, esophageal cancer, head cancer, kidney cancer, liver cancer, lung cancer, neck cancer, ovarian cancer, pancreatic cancer, prostate cancer, stomach cancer, uterine cancer, testicular cancer, thyroid cancer, Burkitt's lymphoma, Non-Hodgkin's lymphoma; Ewing's sarcoma, hemangiosarcoma, Kaposi's sarcoma, liposarcoma, myosarcoma, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, Schwannomas, thyroid cancer, astrocytoma, melanoma, carcinosarcoma, Hodgkin's disease, Wilms' tumor and teratocarcinomas.

10. The method according to claim 5 wherein said compound is

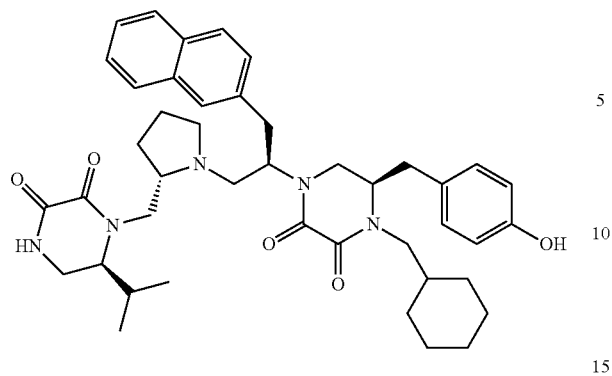
or a pharmaceutically acceptable salt or stereoisomer thereof.
* * * * *